(12) United States Patent
Demopulos et al.

(10) Patent No.: US 12,133,842 B2
(45) Date of Patent: *Nov. 5, 2024

(54) STABLE PRESERVATIVE-FREE MYDRIATIC AND ANTI-INFLAMMATORY SOLUTIONS FOR INJECTION

(71) Applicant: RAYNE INTRAOCULAR LENSES LIMITED, Worthing (GB)

(72) Inventors: Gregory A. Demopulos, Mercer Island, WA (US); Hui-rong Shen, Bothell, WA (US); Clark E. Tedford, Poulsbo, WA (US)

(73) Assignee: Rayner Intraocular Lenses Limited, Worthing (GB)

( * ) Notice: Subject to any disclaimer, the term of this patent is extended or adjusted under 35 U.S.C. 154(b) by 70 days.

This patent is subject to a terminal disclaimer.

(21) Appl. No.: 17/552,872

(22) Filed: Dec. 16, 2021

(65) Prior Publication Data

US 2022/0175726 A1 Jun. 9, 2022

Related U.S. Application Data

(63) Continuation of application No. 17/405,269, filed on Aug. 18, 2021, now abandoned, which is a continuation of application No. 17/171,373, filed on Feb. 9, 2021, now abandoned, which is a continuation of application No. 16/944,609, filed on Jul. 31, 2020, now abandoned, which is a continuation of application No. 16/738,546, filed on Jan. 9, 2020, now abandoned, which is a continuation of application No. 16/454,775, filed on Jun. 27, 2019, now abandoned, which is a continuation of application No. 16/213,758, filed on Dec. 7, 2018, now abandoned, which is a continuation of application No. 15/823,282, filed on Nov. 27, 2017, now abandoned, which is a continuation of application No. 15/278,514, filed on Sep. 28, 2016, now Pat. No. 9,855,246, which is a continuation of application No. 14/721,151, filed on May 26, 2015, now Pat. No. 9,486,406, which is a continuation of application No. 14/061,039, filed on Oct. 23, 2013, now Pat. No. 9,066,856.

(60) Provisional application No. 61/736,179, filed on Dec. 12, 2012, provisional application No. 61/718,026, filed on Oct. 24, 2012.

(51) Int. Cl.
| | | |
|---|---|---|
| *A61K 31/407* | (2006.01) | |
| *A61K 9/00* | (2006.01) | |
| *A61K 31/137* | (2006.01) | |
| *A61K 31/138* | (2006.01) | |

(52) U.S. Cl.
CPC .......... *A61K 31/407* (2013.01); *A61K 9/0048* (2013.01); *A61K 31/137* (2013.01); *A61K 31/138* (2013.01)

(58) Field of Classification Search
CPC .. A61K 31/407; A61K 31/137; A61K 31/138; A61K 9/0048
See application file for complete search history.

(56) References Cited

U.S. PATENT DOCUMENTS

| | | |
|---|---|---|
| 4,402,949 A | 9/1983 | Hartmann |
| 4,474,751 A | 10/1984 | Haslam |
| 4,474,811 A | 10/1984 | Masuda |
| 4,550,022 A | 10/1985 | Garabedian |
| 4,876,250 A | 10/1989 | Clark |
| 4,938,970 A | 7/1990 | Hustead |
| 5,051,433 A | 9/1991 | Stoltefuss |
| 5,051,443 A | 9/1991 | Neufeld |
| 5,110,493 A | 5/1992 | Cherng-Chyi |
| 5,212,196 A | 5/1993 | House |
| 5,298,487 A | 3/1994 | Chen |
| 5,371,078 A | 12/1994 | Clark |
| 5,523,316 A | 6/1996 | Gan |
| 5,587,175 A | 12/1996 | Viegas |
| 5,612,027 A | 3/1997 | Galin |
| 5,624,893 A | 4/1997 | Yanni |
| 5,696,091 A | 12/1997 | York |
| 5,759,532 A | 6/1998 | Galin |
| 5,767,105 A | 6/1998 | Peyman |
| 5,798,356 A | 8/1998 | Doshi |
| 5,800,385 A | 9/1998 | Demopulos |
| 5,811,446 A | 9/1998 | Thomas |
| 5,820,583 A | 10/1998 | Demopulos |
| 5,858,017 A | 1/1999 | Demopulos |
| 5,860,950 A | 1/1999 | Demopulos |
| 5,972,326 A | 10/1999 | Galin |
| 6,030,974 A | 2/2000 | Schwartz |

(Continued)

FOREIGN PATENT DOCUMENTS

| | | |
|---|---|---|
| CN | 101327325 | 12/2008 |
| EP | 0364266 | 4/1990 |

(Continued)

OTHER PUBLICATIONS

Oxtoby, D. W. N., Norman H., "Chapter 6—Acid-Base Equilibria," Principles of Modern Chemistry, 3rd Edition, Saunders College Publishing, Chapter 6: 209-250, (1996).

(Continued)

*Primary Examiner* — Kevin E Weddington

(74) *Attorney, Agent, or Firm* — Christensen O'Connor Johnson Kindness PLLC

(57) ABSTRACT

The present invention relates to stable, preservative- and antioxidant-free liquid formulations of phenylephrine and ketorolac for injection.

10 Claims, 29 Drawing Sheets

(56) References Cited

U.S. PATENT DOCUMENTS

Figure 20A:
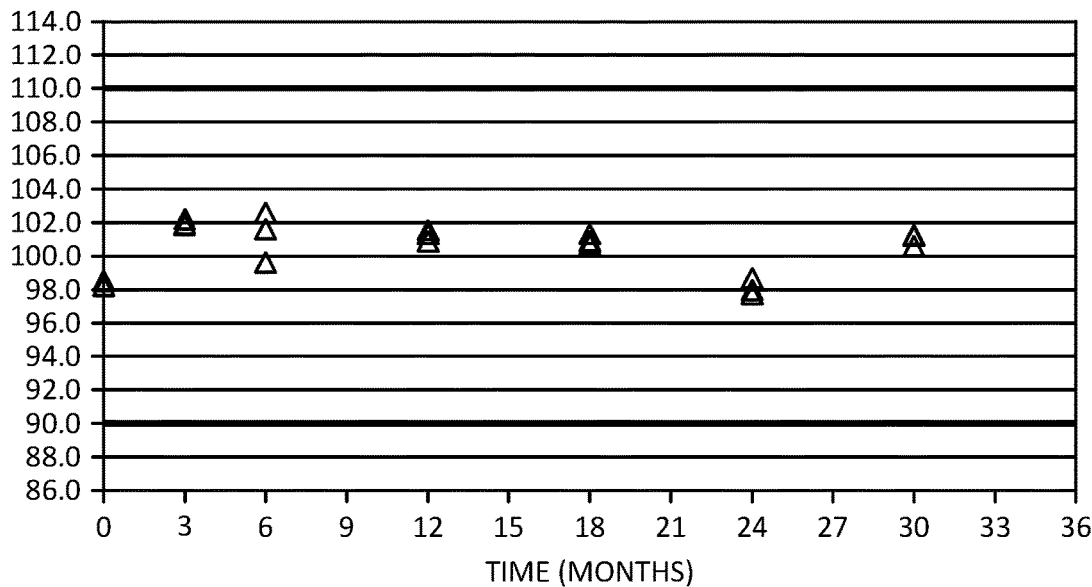

| | | | |
|---|---|---|---|
| 6,056,715 A | 5/2000 | Demopulos | |
| 6,117,907 A | 9/2000 | Sher | |
| 6,210,394 B1 | 4/2001 | Demopulos | |
| 6,218,428 B1 | 4/2001 | Chynn | |
| 6,242,447 B1 | 6/2001 | Demopulos | |
| 6,254,585 B1 | 7/2001 | Demopulos | |
| 6,261,279 B1 | 7/2001 | Demopulos | |
| 6,280,745 B1 | 8/2001 | Flore | |
| 6,350,781 B1 | 2/2002 | Shahinian, Jr. | |
| 6,395,746 B1 | 5/2002 | Cagle | |
| 6,413,961 B1 | 7/2002 | Demopulos | |
| 6,420,432 B2 | 7/2002 | Demopulos | |
| 6,492,332 B1 | 12/2002 | Demopulos | |
| 6,495,598 B1 | 12/2002 | Yoneda | |
| 6,562,873 B2 | 5/2003 | Olejnik | |
| 6,645,168 B2 | 11/2003 | Demopulos | |
| 7,091,181 B2 | 8/2006 | Demopulos | |
| 7,842,714 B2 | 11/2010 | Farnes | |
| 7,973,068 B2 | 7/2011 | Demopulos | |
| 8,173,707 B2 | 5/2012 | Demopulos | |
| 8,586,633 B2 | 11/2013 | Demopulos | |
| 9,066,856 B2 * | 6/2015 | Demopulos | A61K 31/138 |
| 9,278,101 B2 | 3/2016 | Demopulos | |
| 9,399,040 B2 | 7/2016 | Demopulos | |
| 9,486,406 B2 * | 11/2016 | Demopulos | A61P 41/00 |
| 9,585,895 B2 | 3/2017 | Demopulos | |
| 9,855,246 B2 * | 1/2018 | Demopulos | A61K 31/407 |
| 2002/0071874 A1 | 6/2002 | Olejnik | |
| 2002/0128267 A1 | 9/2002 | Bandyopadhyay | |
| 2002/0183279 A1 | 12/2002 | Tanaka | |
| 2003/0017199 A1 | 1/2003 | Woodward | |
| 2003/0087962 A1 | 5/2003 | Demopulos | |
| 2003/0096807 A1 | 5/2003 | Demopulos | |
| 2003/0191187 A1 | 10/2003 | Lee | |
| 2004/0072809 A1 | 4/2004 | Demopulos | |
| 2004/0242588 A1 | 12/2004 | Dejovin | |
| 2008/0194649 A1 | 8/2008 | Khatib | |
| 2009/0042968 A1 | 2/2009 | Whiting | |
| 2009/0258850 A1 | 10/2009 | Frincke | |
| 2010/0087503 A1 | 4/2010 | Farnes | |
| 2010/0311688 A1 | 12/2010 | Chapin | |
| 2010/0311705 A1 | 12/2010 | Demopulos | |
| 2011/0105450 A1 | 5/2011 | Chapin | |
| 2012/0022094 A1 | 1/2012 | Harris | |
| 2013/0065869 A1 | 3/2013 | Demopulos | |
| 2013/0079344 A1 | 3/2013 | Demopulos | |
| 2014/0221326 A1 | 8/2014 | Demopulos | |
| 2014/0235597 A1 | 8/2014 | Demopulos | |
| 2014/0235691 A1 | 8/2014 | Demopulos | |
| 2015/0342928 A1 | 12/2015 | Demopulos | |
| 2016/0279099 A1 | 9/2016 | Demopulos | |
| 2017/0100412 A1 | 4/2017 | Demopulos | |
| 2017/0196838 A1 | 7/2017 | Demopulos | |
| 2017/0312295 A1 | 11/2017 | Demopulos | |

FOREIGN PATENT DOCUMENTS

| | | |
|---|---|---|
| EP | 0364266 A2 | 4/1990 |
| EP | 0550921 | 7/1993 |
| EP | 0903151 | 3/1999 |
| JP | 2001516258 | 9/2001 |
| JP | 2002161032 | 6/2002 |
| JP | 2002161032 A2 | 6/2002 |
| JP | 2002523513 | 7/2002 |
| JP | 6017053 | 10/2016 |
| WO | 8707141 | 12/1987 |
| WO | 9102527 | 3/1991 |
| WO | 9204008 | 3/1992 |
| WO | 9408602 | 4/1994 |
| WO | 9509003 | 4/1995 |
| WO | 9516435 | 6/1995 |
| WO | 9516435 A2 | 6/1995 |
| WO | 9534298 | 12/1995 |
| WO | 9600055 | 1/1996 |
| WO | 9619233 | 6/1996 |
| WO | 9709973 | 3/1997 |
| WO | 9721445 | 6/1997 |
| WO | 9804171 | 2/1998 |
| WO | 9838996 | 9/1998 |
| WO | 9841171 | 9/1998 |
| WO | 9847366 | 10/1998 |
| WO | 9847890 | 10/1998 |
| WO | 0001379 | 1/2000 |
| WO | 0003705 | 1/2000 |
| WO | 0023061 | 4/2000 |
| WO | 0023062 | 4/2000 |
| WO | 0023066 | 4/2000 |
| WO | 0023072 | 4/2000 |
| WO | 0025745 | 5/2000 |
| WO | 0035433 | 6/2000 |
| WO | 0069255 | 11/2000 |
| WO | 0107050 | 2/2001 |
| WO | 0141550 | 6/2001 |
| WO | 0182914 | 11/2001 |
| WO | 0205815 | 1/2002 |
| WO | 0209702 | 2/2002 |
| WO | 0224191 | 3/2002 |
| WO | 2004010894 | 2/2004 |
| WO | 2009061431 | 5/2009 |
| WO | 2009074853 | 6/2009 |
| WO | 2010105042 | 9/2010 |
| WO | 2012016000 | 2/2012 |
| WO | 2014066485 | 5/2014 |

OTHER PUBLICATIONS

Parikh, C. H., et al., "Ocular surgical pharmacology: corneal endothelial safety and toxicity," Curr Opin Ophthalmol, 14(4): 178-185, (2003).

Peyman, G. A., et al., "Combination therapies in ophthalmology: implications for intravitreal delivery," J Ophthalmic Vis Res, 6(1): 36-46, (2011).

Pflugfelder, S. C., et al., "Corneal toxicity with an antibiotic/steroidsoaked collagen shield," Arch Ophthalmol, 110(1): 20, (1992).

Prasher, P., "Acute corneal melt associated with topical bromfenac use," Eye Contact Lens, 38(4): 260-262, (2012).

Robinson, J. C., "Chapter 2—Ocular Anatomy and Physiology Relevant to Ocular Drug Delivery," In: Ophthalmic Drug Delivery Systems, I st edition, Mitra A. K., editor, New York, Marcel Dekker, Inc., pp. 29-57, (1993).

Storr-Paulsen, A., et al., "Antibiotics in irrigation solution for cataract surgery. A laboratory investigation of the pharmacological stability and bacteriological susceptibility," Acta Ophthalmol Scand, 76(2): 180-183, (1998).

Teal, P., et al., "Corneal subepithelial infiltrates following excimer laser photorefractive keratectomy," J Cataract Refract Surg, 21(5): 516-518, (1995).

Trommer, H., et al., "Investigating the degradation of the sympathomimetic drug phenylephrine by electrospray ionisation-mass spectrometry," J Pharm Biomed Anal, 52(2): 203-209, (2010).

Troup, A. E., et al., "Degradation of Phenylephrine Hydrochloride in Tablet Formulations Containing Aspirin," J Pharm Sci, 53: 375-379, (1964).

Urtti, A., "Challenges and obstacles of ocular pharmacokinetics and drug delivery," Adv Drug Deliv Rev, 58(11): 1131-1135, (2006).

Walters, T., et al., "In vivo pharmacokinetics and in vitro pharmacodynamics of nepafenac, amfenac, ketorolac, and bromfenac," J Cataract Refract Surg, 33(9): 1539-1545, (2007).

Waterbury, L. D., et al., "Comparison of cyclooxygenase inhibitory activity and ocular anti-inflammatory effects of ketorolac tromethamine and bromfenac sodium," Curr Med Res Opin, 22(6): 1133-1140, (2006).

Yee, R. W., "Analgesic efficacy and safety of nonpreserved ketorolac tromethamine ophthalmic solution following radial keratotomy. Ketorolac Radial Keratotomy Study Group," Am J Ophthalmol, 125(4):4 72-480, (1998).

Zhu, Y.-H. Z., Zhi-ling; Zhao, Wei; Pang, Dai-wen, "Voltammetric behavior and determination of phenylephrine at a glassy carbon electrode modified with multi-wall carbon nanotubes," Sensors and Actuators B Chemical, 119: 306-314, (2006).

(56) References Cited

OTHER PUBLICATIONS

Alcon Laboratories, I., "BBS Sterile Irrigating Solution (balanced salt solution)—Package Insert," (2012).
Alcon Laboratories, I., "BSS Plus—500 mg—Package Insert," (2003).
Allergan Inc., "ACULAR (ketorolac tromethamine ophthalmic solution) 0.5%, Package Insert," (2005).
Allergan Inc., "Allergan Annual Report," (2001).
American Regent, Inc., "Epinephrine—epinephrine injection, solution—Package Insert," (2011).
Baxter Healthcare Corporation, "Balanced Salt Solution (Sterile Irrigating Solution)—Package Insert," (1995).
American Academy of Ophthalmology, "Chapter 8—Surgery for Cataract," Basic and Clinical Science Course (BCSC)—Section 11:Lens and Cataract, pp. 81-159, (2001).
Center for Drug Evaluation and Research, "Approval Package for Acular" Application No. 19-700/S-OI 9 20-811/S-003, Approval Date: Feb. 8, 2002, (2002).
Center for Drug Evaluation and Research, "Chemistry Review(s) for Acuvail" Application No. 21-132, Review Date: Jul. 14, 2009, (2009).
European Medicines Agency, "ICH Topic Q 1 A (R2), Stability Testin of new Drug Substances and Products, Note for Guidance on Stability Testing: Stability Testing of New Drug Substances and Products," Application No. CPMP/ICH/2736/99,(2003).
Food and Drug Administration, "Draft—Guidance for Industry—Stability Testing of Drug Substances and Drug Products," (1998).
Food and Drug Administration, "Guidance for Industry QIA (R2) Stability Testing of New Drug Substances of New Drug Substances and Products," (2003).
Hercules, "Aqualon—Sodium Carboxymethylcellulose Physical and Chemical Properties," (1999).
ICH Expert Working Group, "ICH Harmonised Tripartite Guideline—Stability Testing of New Drug Substances and Products QIA (R2)," International Conference on Harmonisation of Technical Requirement for Registration of Pharmaceuticals for Human Use, (2003).
JHP Pharmaceuticals, LLC., "Adrenalin Chloride Solution—Package Insert," (2008).
Beacon Pharmaceuticals, Ltd., "MHRA Public Assessment Report for Beacon's Ketorolac Trometamol 30mg/ml Solution for Injection Ketorolac Trometamol," MHRA, (2007).
Thornton & Ross, "Thornton and Ross Cold & Flu Formula Oral Solution PL 00240/0144," MHRA (2008).
Omeros Corporation, "SEC Form 10-Q," (2010).
Omeros Corporation, "SEC Form 10-Q," (2009).
Omeros Corporation, "SEC Form 10-K - Annual Report," (2010).
US Pharmacopeial Convention, Inc., "The United States Pharmacopeia 24—The National Formulary 19 (USP 24-NF 19)," pp. 946-950, (2000).
US Pharmacopeial Convention, Inc.,"The United States Pharmacopeia 35 (USP 35)," pp. 3623-3624, (2011).
Physician's Desk Reference, (53rd ed.) p. 493-94, (1999).
Physician's Desk Reference, (62nd ed.) p. 538-39, (2008).
"Phenylephrine Hydrochloride—phenylephrine hydrochloride injection," West-Ward Pharmaceutical Corporation, p. 1-7, (2011).
Arshinoff, S. et al., "The Pharmacotherapy of Cataract Surgery," In: Ophthalmology, 1st edition, YanoffM. D., JS, editor, Chapter 20: 4:20.21-24:20.24, (1999).
Amdipharm UK Limited, "Summary of Product Characteristics—Phenylephrine 10 mg/ml Injection," Sep. 14, 2016.
Avalere Health, "Medicare Payment Differentials Across Outpatient Settings of Care," pp. 1-43, (2016).
Devgan, U., "Cataract surgery can be performed in pseudoexfoliation cases without expansion devices," Ocular Surgery News, pp. 1-4, (2015).
Food and Drug Administration, "Recall—Firm Press Release: American Regent Initiates Nationwide Voluntary Recall of Phenylephrine HCl Injection, USP, 1 % 5 mL Vial, Lot #0693 Due to Visible Particles," (2012).
Vantage Specialty Ingredients, "CMC 7LF USP FCC Pharmaceutical," Accessed at <http://www.rugerchemical.com/products/cmc-7lf-usp-fcc-pharmaceutical>.
Sentiss, "Irifrin BK Eye Drop 0.4 ml—Package Insert," (2015).
Sentiss, "Irifrin Eye Drops—Package Insert," (2015).
Alcon Laboratories, Inc., "Cyclomydril—cyclopentolate hydrochloride and phenylephrine hydrochloride solution/drops—Package Insert," (2013).
Misgen, R., "Compatibilities and Incompatibilities of Some Intravenous Solution Admixures," Am J Hosp Pharm, 22(2): 92-94, (1965).
Moroi, S.E., et al. (2001). Ocular pharmacology. In Goodman & Gilman's The Pharmacological Basis of Therapeutics (J.G. Hardman and L.E. Limbird, Eds.) Tenth Edition. (pp. 1821-1848). McGraw-Hill.
Nakamura, S., et al., "Evaluation of a1-adrenoceptors in the rabbit iris: pharmacological characterization and expression of mRNA," Br J Pharmacol 127:1367-1374 (1999).
Narendran, N., et al., "The cataract national dataset electronic multicenter audit of 55 567 operations: risk stratification for posterior capsule mpture and vitreous loss," Eye 23:31-37 (2009).
Neuhann, T.F. et al. (2009). Capsulorrhexis. In Cataract Surgery: Expert Consult (R. Steinert, Ed.) Third Edition. (pp. 163-171 ). Elsevier.
Radi, Z.A., et al., "The pathophysiologic role of cyclooxygenases in the eye," J Ocular Pharmacol Ther 24(2): 141-151 (2008).
Rutar, T., et al., "Risk factors for intraoperative complications in resident-performed phasoemulsificatin surgery," Ophthalmology 116:431-436 (2009).
Schalnus, R. "Topical nonsteroidal anti-inflammatory therapy in ophthalmology," Ophthalmologica 217:89-98 (2003).
Waitzman, M.B. "Prostaglandins and the eye," Afetabolic, Pediatric and Systemic Ophthalmology 6: 17-26 (1982).
Menapace, R. (2005). Prevention of posterior capsule opacification. In Cataract and Refractive Surgery (T. Kohnen and D. Koch, Eds.) (pp. 101-122). Springer.
ACULAR [package insert]. Allergan, Inc., Irvine, CA; 2004.
Srinivasan, M., et al., "Sodium bicarbonate—an alternative to hyaluronidase in ocular anaesthesia for cataract surgery," Indian Journal of Ophthalmology 48(4):285-89 (2000).
Solomon, K.D., et al., "Topical 0.5% ketorolac vs 0.03% flurbiprofen for inhibition of miosis during cataract surgery," Arch Opthalmol 115: 1119-1122 (1997).
Gills, J.P., "Injectable Prostaglandins Inhibitors Prior to Cataract Surgery," J Cataract Refract 13:459-460 (1987).
Yuen, V.H., et al., "Comparison of three modified lidocaine solutions for use in eyelid anesthesia," Ophthalmic Plastic and Reconsturctie Surgery 15(2): 143-147 (1999).
Krohn, J., et al., "Retrobulbar anesthesia with and without hyaluronidase in extracapsular cataract surgery," Acta Opthalmologica 71 :791-795 (1993).
"Toxic Anterior Segernent Syndrome After Acataract Surgery—Maine, 2006," MMWR Weekly 56(25):629-630 (2007), retrieved from <http:/ /wwwv.cdc.gov/mmwr/preview/mmwrhtml/mm5625a2.htm> on May 12, 2014.
Slack, J.W., et al., "A Bisufitie-free Intraocular Epinephrine Solution," Am.J.Opthalmol. 110(1):77-82 (1990).
Corbett et al., "Intraocular adrenaline maintains mydriasis during cataract surgery," Br. J Ophthamol. 78:95-98 (1994) (Abstract Only).
Omeros Corporation, "Safety, Efficacy and Phamacokinetics of OMS302 in Subjects Undergoing Intraocular Lens Replacements With Phacoemulsification," Smart Patients, Inc. (2016).
Zimm, J.L, et al., "Effects of topical suprofen and flurbipmfen on the miosis produced by anterior chamber inigation with cholinergic agonists," J Cataract Refract Surg 17:790-793 (1991 ).
Flach, A.J., et al., "The Effect of Ketorolac Tromethamine in Reducing Postoperative Inflammation: Double-Mask Parallel Comparison with Dexamethasone," Annals of Ophthalmology 21:407-411 (1989).
Backstrom, G., "Behndig ARedilatation with intracameral mydriatics in phacoemulsification surgery," Acia Ophthalmol Scand 84(1):100-4 (2006).

(56) References Cited

OTHER PUBLICATIONS

Perry, R.D., et al., "An update on the use of ophthalmic ketorolac tromethamine 0.4%," Expert Opin Pharmacother. 7(1):99-107 (2006).
Stewart, R. et al., "Efficacy and Safety Profile of Ketorolac 0.5% Ophthalmic Solution in the Prevention of Surgically Induced Miosis During Cataract Surgery," Clinical Therapeutics 21(4):723-732 (1999).
DeRuiter, "Principals of Drug Action 2 at 4," (Fall, 2002). Accessed Apr. 26, 2015 at <www.auburn.edu./~deruija/nsaids_2002.pdf>.
Hardman, J.G., Eel, G-oodman and Gilman's The Pharmacologic Basis of Therapeutics, 10th Edition; New York: McGraw-Hin Medical, 2001; pp. 145-146, 216-8, 687-92.
Zanetti, F.R., et al., "Effect of preoperative use of topical prednisolone acetate, ketorolac tromethamine, nepafenac and placebo, on the maintenance of intraoperative mydriasis during cataract surgery: a randomized trial," Indian J Ophthalmol. 60(4):277-81 (2012).
Lundberg, B., et al., "Intracameral mydriatics in phacoemulsification cataract surgery," J Cataract Refract Surg 29:2366-2371 (2003).
Bandyopadhyay, P., et al. (2010). Development of ophthalmic formulation. In Pharmaceutical Dosage Forms (pp. 254-286) New York:NY: Informa Healthcare.
Brown, M.R. W ., et al., "The Preservation of Ophthalmic Preparations," J Soe, Cosmetic Chemists 16:369-393 (1965).
Das Gupta, V., et al., "Chemical Stabilities of Lignocaine Hydrochloride and Phenylephrine Hydrochloride in Aqueous Solution," Journal of Clinical and Hospital Pharmacy, 11:449-452 (1986).
Edelhauser, H.F., et al., "Corneal Edema and the Intraocular Use of Epinephrine," American Journal of Ophthalomology 93:327-333 (1982).
Ellis, P.P. (1981). Basic considerations. fn Ocular Therapeutics and Pharmacology (pp. 3-23) St. Louis:MO: The C.V. Mosby Company.
Food and Drug Administration, "Guidance for Industry Q1A(R2) Stability Testing of New Drugs Substances and Products," (2003).
Heath, P., et al., "Use of Phenylephrine Hydrochloride (Neo-Synephrine Hydrochloride@) in Ophthalmology," Archives of Ophthalmology 41(2):172-177 (1949).
Lang, J.C., et al. (2002). Design and Evalution of Ophthalmic Pharmaceutical Products. In Ivfodern Pharmaceutics (pp. 626-698) Fort Worth:TX:Marcel Decker, Inc.
Lewis, RJ. (2007). Hawley's Condensed Chemical Dictionary, 15th Edition, (pp. 188-189), Hoboken:NJ: John Wiley & Sons, Inc.
Mauger, T.F., et al. (1996). Mosby 's Ocular Drug Handbook (pp. 36-40), St Louis:MO: Mosby-Year Book, Inc.
Oztilrk, F., et al., "The efficacy of 2.5% phenylephrine and flurbiprofen combined in inducing and maintaing pupillary dilatation during cataract surgery," European Journal of Ophthalmology 10(2):144-148 (2000).
Physicians' Desk Reference for Ophthamology, 26111 Edition, (pp. 1-2, 7-8, 15, 201, 209, 221-222, 235) (1998).
Physicians' Desk Reference For Nonprescription Drugs and Dietary Supplements, 24th Edition, (pp. 620-621) (2003).
Reddy, I.K. (Ed.), (1996). Ocular Therapeutics and Drug Delivery, (pp. 3-29, 171-193, 204, 377-404, 529-540).
Lang, J.C., et al., (2005). Ophthalmic Preparations. In Remington—The Science and Practice of Pharmacy, 21st Edition (pp. 850-870).
The United States Pharmacopeia, 23rd Edition, (pp. 10-14, 1211-1217, 1940-1947, 1959-1963) (1995).
Brandl, M., et al., "Approaches for Improving the Stability of Ketorolac in Powder Blends," Journal of Pharmaceutical Sciences 84(10): 1151-1153 (1995).
Brandl, M., et al., "Racemization of Ketorolac in Aqueous Solution," Journal of Pharmaceutical Sciences 84(9): 1045-1048 (1995).
Center for Drug Evaluation and Research, "Application No. 21-132 Chemistry, Review(s)," 2009.
Center for Drug Evaluation and Research, "Application No. 2079260rigls000 Chemistry Review(s)," 2014.
Center for Drug Evaluation and Research, "Application No. 2079260rigls000 Summary Review," 2015.

Das Gupta, V., et al., "Stability of Phenylephrine Hydrochloride Nasal Drops," American Journal of Hospital Pharmacy 29:870-873 ( 1972).
Gu, L, et al., "Kinetics and mechanisms of the autoxidation of ketorolac tromethamine in aqueous solution," International Journal of Pharmaceutics 41:95-104 (1988).
Gu, L., et al., "Light degradation of ketorolac tromethamine." International Journal of Pharmaceutics 41: 105-113 (1988).
Millard, B.J., et al., "The stability of aqueous solutions of phenylephrine at elevated temperatures: identification of the decomposition products," J Phann. Pharmac. 25(Suppl.):24p-3 lp (1973).
Neo-Synephrine—phenylephrine hydrochloride injection, solution [Package Insert]. Lake Forest, IL:Hospira, Inc., 2010.
Phenylephrine IOMG/ML Solution for Injection of Infusion [Package Insert] Kent, UK: Beacon Pharmaceuticals (2011 ).
Omeros Corporation, Response to Communication Pursuant to Article 94(3), European Patent Application No. 03 772122.2. Sep. 15, 2011.
Code of Federal Regulation, 21 CFR Suhchapter C:Drugs: General: Part 200—General, (pp. 5-8). Updated Apr. 1, 2015.
ACULAR (ketorolac tromethamine ophthalmic solution) 0.5% [Package Insert]. Irvine, CA: Allergan, Inc.; 2001.
ACULAR PF (ketorolac tromethamine ophthalmic solution) 0.5% Preservative-Free [Package Insert]. Irvine, CA: Allergan, Inc.; 2002.
ACUVAIL TM (ketorolac tromethamine ophthalmic solution) 0.45% [Package Insert]. Irvine, CA: Allergan, Inc.; 2009.
BSS PLUS Sterile Intraocular Irrigating Solution [Package Insert]. Fort Worth, TX: Alcon Lahatories, Inc., 2003.
OCUFEN (flurbiprofen sodium ophthalmic solution, USP) 0.03% [Package Insert]. Irvine, CA: Allergan, Inc., 2001.
Phenylephrine Hydrochoride Ophthalmic Solution, USP 2.5%—Sterile [Package Insert]. Lake Forset, IL: Akom, Inc., 2011.
Physicians' Desk Reference, 50th Edition, (pp. 2325-2326) (1996).
Adamczyk, D.T .; Jaanus, S.D., Antiallergy Drugs and Decongestants. In Clinical Ocular Pharmacology; Bartlett. J.D., Ed.; 5th Edition; Butterworth, Heinemaru1, Elsevier: St. Louis, 2008; pp. 247.
Belmonte C., et al., "Neural basis of sensation in intact and injured corneas," Exp Eye Res. 78(3):513-25 (2004).
Coman, O.A., et al., "Particularities of vascular reactivity of the conjunctiva and iris in rats," Romanian journal of morphology and embryology = Revue roumaine de morphologie et embryologie, 49(1):53-56 (2008).
Floman, N ., et al., "Mechanism of steroid action in ocular inflammation: Inhibition of prosiaglandin production," Invest Ophthalmol Vis Sci. 16(1):69-73 (1977).
Grosser, T. et al., Anti-Inflammatory, Antipyretic, and Analgesic Agents; Pharmatiotherapy of Gout in Goodman and Gilman's Pharmacological Basis of Therapeutics, 12th Edition; Brunton, L, Ed .; New York: Mc Graw Hill Medical, 2011; pp. 962-963.
Hashimoto, Y., et al., "Effects of ciliary ganglionectomy on contractile responses in the dilator muscle of the rat iris," Exp Eye Res. 56(2):135-41 (1993).
Hoffman, B., Catecholamine, Sympathomimetic Drugs, and Adrenergic Receptor Antagonists. In Goodman and Gilman's Pharmacological Basis of Therapeutics, 10th Edition. Hardman, J.G., Ed.; New York; McGraw Hill Medical, 2001, p. 232.
Loux J, Yankell S., Ocular vasocongestion assay in rabbits. Federation Proceedings 1973, 32:3(1).
Miyake, K., et al., "Prevention of cystoid macular ederna after lens extraction by topical indomethacin. III. Radioimmunoassay measurements of prostaglandins in the aqueous during and after lens extraction procedures," Graejes Arch Clin Exp Ophthalmol 209: 83-88, (1978).
Novack, G.D., "Ophthalmic drug development: procedural considerations," J Glaucoma 7(3):202-9 (1998).
Perkins, E.S., "Prostaglandins and ocular trauma," Adv Ophthalmol. 34:149-52 (1977).
Portello, J.K. Mydriatics and Mydriolytics. In Clinical Ocular Pharmacology; Bartlett, J.D., Ed.; St Louis: Butterworth, Heinemann, Elsevier, 2008; pp. 114, 117.
Rao, K.N., et al., "Role of aspirin in cataract surgery," Indian J Ophthalmol. 33(2):89-90 (1985).

(56) References Cited

OTHER PUBLICATIONS

Toris, C.B., et al., "The biology, pathology and therapeutic use of prostaglandins in the eye," Clinical Lipidology 6(5):577-591 (2011).
Zschauer, A., et al., "Role of endothelium and hyperpolarization in CG RP-induced vasodilation of rabbit ophthalmic artery," American Journal of Physiology—Heart and Circulatory Physiology 263(2):32-2(H359-H365) (1992).
Gamache, D.A., et al., "Nepafenac, a unique nonsteroidal prodrug with potential utility in the treatment of trauma-induced ocular inflammation: I. Assessment of anti-inflammatory efficacy" Inflammation 24(4):357-70 (2000).
Whitaker, J.S., Declaration under 37 CFR 1.132 dated Feb. 14, 2012.
Database WPI Week 200239; Der1-vent Publications Ltd, London, GB; AN 2002-362397 XP002478749 & WO02/2419 J A, Yong Guang Pharm Co Ltd, Mar. 28, 2002. Abstract Only.
Gillart et al., "Effects of Local Clonidine for Prolongation of Akinesia After Peribulbar Block," Anesthesiology 31(3A): A941-A.. 942 (1994).
Grond, S., et al., "Inhibition of Synovial Plasma Extravasation by Preemptive Administration of an Antiinfiarnmatory Irrigation Solution in the Rat Knee," Anesth Analg 92; 1301-6 (200 I ).
Malhotra et al., "Comparison of the cardiovasculare effects of 2.5% phenylephrine and 10% phenylephrine during ophthalmic surgery," Eye 12:973-975 (1998).
Keates, R.H., et al., "Clinical trial of flurbiprofen to maintain pupillary dilation during cataract surgery," Ann. Ophthalmol. 16(10):919-921 (1984).
Keates, RH., et al., "The effect of topical indornethacin ophthalmic solution in maintaining mydriasis during cataract surgery," Ann. Ophthalmol. 16(12) 1116-1121 (1984).
Gills, J.P., et al., "Pharmacodynamics of Cataract Surgery" & "Strategies for Applying State of the Art Techniques," Cataract Surgery the State of the Art Chapters 3 & 18:19-26, 229-240 (1998).
McDermott, M.L., et al., "Ophthalmic inigants: a current review and update," Ophthalmic Surg. 19(10):724-733 (1988).
Duffin, R.M., et al., "2.5% v 10% phenylepluine in maintaining mydriasis during cataract surgery," Arch. Ophthalmol. 101(12):1903-1906 (1983).
Falcon Pharmaceuticals, Ltd., et al. (2004) Phenylephrine Hydrochloride Ophthalmic Solution, 2.5%. Fort Worth, TX. (Package Insert).
DeMarinis, Robert, M., et al., (1987) "Structure-Activity Relationships for alpha-1 Adrenergic Receptor Agonists and Antagonists," The alpha-1 Adrenergic Receptors, Chapter 6, pp. 211-265.
U.S. National Institutes of Health, "Safety, Efficacy and Pharmacokinectics of OMS302 in Subjects Undergoing Intraocular Lens Replacement With Phacoemulsification," Clinical Trials Identifier:NCT01579565, May 1, 2012, Accessed at <https://clinicaltrials.gov/archive/NCTO 1579565/2012_05_01>.
Timmerman, Luke, "Omeros Combo Drug Passes Cataract Surgery Study," Mar. 23, 2011, Accessed at <http://www.kconomy.com/seattle/2011 /03/23/omeros-combo-drug-passes-cataract-surgery-study/>.
Omeros Corporation, "Omeros' Ophthalmology Product OMS302 Achieves Co-Primary Endpoints in Phase 2b Clinical Study—OMS302 Maintains Pupil Dilation During Cataract Surgery and Reduces Postoperative Pain," Mar. 23, 2011, Accessed at <http://investor.omeros.com/_phoenix.zhtml?c=219263&p=irolnewsArticle_Print&ID=1541955>.
Lowry, Fran, "New Drug Maintains Mydriasis During Lens Replacement," Oct. 28, 2011, Accessed at <http:medscape,com/viewarticle/7 52489>.
PR Newswire, "Omeros' Ophthalmology Product OMS302 Achieves Primary and Secondary Endpoint in Phase 3 Clinical Trial," Omeros Corporation Press Release, Mar. 13, 2012, Accessed at <http://www.virtualizationconference.com/node/2202855>.
Rosenblatt, Mark, et al., "A Phase 3 clinical trial of the drug product OMS302 delivered intracamerally in BSS during Intraocular lens replacement surgery," American Academy of Ophthalmology Annual Meeting, Nov. 10, 2012 (Conference Poster).
PR Newswire, "Omeros to Present Data from Successful OMS302 Phase 3 Clinical Trial at the American Academy of Ophthalmology Annual Meeting," Omeros Corporation Press Release, Nov. 8, 2012, Accessed at <http://www.pnewswire.com/newsrd~ascs/cnrwros-H)-present-data-from-successful-oms302-phase-3-clinical-triai-at-the-american-academy-of-opthamology-annual-meeting-17783605 I .html>.
PR Newswire, "Omeros Announces Positive OMS302 Safety Data in Phase 3 Clinical Trial," Omeros Corporation Press Release, Jan. 22, 2013, Accessed at <http://www.prnewswire.com/news-releases/omeros-announces-positive-oms302-safety-data-in-phase-3-clinical-trial-187854311.html>.
Hirowatari, T., et al., "Availability of TPD ophthalmic Solution (Mixture of Mydria-P Solution, Neosynesin Kowa Solution, and Diclod Solution)," New Ophthalmology 19(1):107-109 (2002). Japanese Language.
Hirowatari, T., et al., "Availability of TPD ophthalmic Solution (Mixture of Mydria-P Solution, Neosynesin Kowa Solution, and Diclod Solution)," New Ophthamology 19(1): 107-109 (2002). English Translation.
Ogawa, T., et al., "Effects of Pre-installed Mydriatics on the Intraocular Concentration and Anti-inflammatory Action of Topical 0.1 % Pranoprofen (3)—Study on Permeability Factor," Journal of Japanese Ophthalmological Society 96(11): 1379-1386 (1992). Japanese Language.
Ogawa, T., et al., "Effects of Pre-installed Mydriatics on the Intraocular Concentration and Anti-inflammatory Action of Topical 0.1% Pranoprofen (3)—Study on Permeability Factor," Journal of Japanese Ophthalmnological Society 96(H): 1379-1386 (1992). English Translation.
Crandall, A., et al. (Oct. 2011). OMS302 Maintains Mydriasis and Decrease Postoperative Pain in Cataract Surgery. Poster Session presented at the meeting of the American Academy of Ophthalmology, Orlando, FL.
Toxic Anterior Segment Syndromne After Cataract Surgery—ivfaine, 2006 (Jun. 27, 2007). In A1AffVR Weekly. Retrieved from <http:/cdc.gov/mmwr/preview/mmwrhtm1/mm5625a2.htm>.
Allergan. (2011 ). Acuvail (ketorolac tromethamine ophthabnic solution) 0.45%. Irvine, CA. (Package Insert).
Loyd, A. (2001 ). Phenlephrine 0.25%Ophthalmic Solution, Preservative Free. In Sterile Product Compounding. Retrieved from <http://www.ijpc.com/Abstracts/Abstractcfm?ABS=544> (Abstract Only).
Phenylephrine Hydrochloride Injection, USP 1%. (Package Insert).
Allergan. (2011 ). Acular—ketorolac tromethamine solution/drops. Irvine, CA. (Package Insert).
Akorn, Inc. (2005). A K-DilateTM Phenyiephrine Hydrochloride Ophthalmic Solution, USP 2. 5%—Sterile. Buffalo Grove, IL. (Package Insert).
Allergan. (2001 ). Acular® (ketorolac tromatharnine ophthalmic solution) 0.5% Sterile. Irvine, CA. (Package Insert).
Bedford Laboratories. (2008) Ketorolac fromethamine (ketorolac tromethamine) Injection, Solution Retrieved from <http://dailymed.nlm.nih.gov/dailymed/archives/fdaDruginfo.cfm?archivedid=8730>, (Package Insert).
Falcon Pharmaceuticals, Ltd., et aL Phenylephrine Hydrochloride Ophthalmic Solution, 2.5%. Fort Worth, TX. (Package Insert).
Phenylephrme Hydrochlonde. I2012 .L in Meazcmes Support Unit for Optometrists. Retrieved from <http://www.medsupport.org.uk/IntegratedCRD.nsf/b73d388be6b449968025768c0053I3>. (Package Insert).
InterMed Medical Ltd. (2005). Neo-Synephrine Phenylephrine Hydrochloride 1% Injection. In Information for Health Professionals Data Sheet.
Database WPI Week 200256, Derwent Publications Ltd., London, GB: AN 2002-523513 & JP 2002 161032 A, Tasisho Phann Co. Ltd, Jun. 4, 2002. Abstract Only.
Goodman & Gilman's the Phannacological Basis of Therapeutics, Tenth Edition, McGraw-Hill, Eds., 2001, pp. 145-146, 687.
Grond, S., et al., "Inhibition of Synovial Plasma Extravasation by Preemptive Administration of an Antiinflammatory Irrigation Solution in the Rat Knee," Anesth Analg 92: 1301-6 (2001).

(56) References Cited

OTHER PUBLICATIONS

Malhotra et al., "Comparison of the cardiovasculare effects of 2.5% phenylephrine and 10% phenyk'Pln ine during ophthalmic surgery," Eye 12:973-975 (1998).
Antcliff et al., "The maintenance of per-operative mydriasis in phacoemulsification with topical diclofenac sodium," Eye 11:389-391 (1997).
Liou, Shiow-Wen, et al., "The Effects ofintracameral Adrenaline Infusion on Pupil Size, Pulse Rate, and Blood Pressure During Phacoemulsification," J Ocular Pharmacol Ther 14(4):357-361 (1998).
Gimbel, "The effect of treatment with topical nonsteroidal antiinflammatory drugs with and without intraoperative epinephrine on the maintenance of mydriasis during cataract surgery," Ophthalmology 96(5):585-588 (1989) (Abstract Only).
Shimada, H., et al., "Effects ofFlubiprofen on Extracapsular Cataract Extraction," Journal of the Eye 4(5):719-722 (1987). Japanese language.
Shimada, H., et al., "Effects ofFlubiprofen on Extracapsular Cataract Extraction," Journal of the Eye 4(5):719-722 (1987). English translation.
Titcomb, "Revision of Pharmacology," www.optometry.co.uk 25-34 (2002).
Zimm, Jeffrey L., et al., "Effects of topical suprofen and flurbiprofen on the miosis produced by anterior chamber irrigation with cholinergic agonists," J Cataract Refract Surg 17:790-793 (1991).
Snyder, R.W., et al., "Acular as a single agent for use an an antimiotic and anti-inflammatory in cataract surgery," J Cataract Refract Surg 26(8):1225-1227 (2000).
Shimada, H., et aL, "Effects of an Anti-prostaglandin Agent Added to the Irrigation Solution on Damage to the Anterior Segment in Monkey Eyes Induced by Pars Plana Vitrectomy," Acta Soc Ophthalmol Jpn 93:823-829 (1989).
Miyake et al., "Latanoprost Accelerates Disruption of the BloodAqueous Barrier and the Incidence of Agiographic Cystoid Macular Edema in Early Postoperative Pseudophakias," Arch Ophthalmol 117:34-40 (1999).
Miyake et al., "Enhanced Disruption of the Blood-Aqueous Barrier and the Incidence of Angiographic Cystoid Maciuar Edema by Topical Timolol and Its Preservative in Early Postoperative Pseudophakia," Arch Ophthalmol 119:387-394 (2001).
Fichman, "Anesthesia and preoperative and postoperative medications," Current Opinion in Ophthalmology 7: 17-20 (1996).
Alcon Laboratories, "The Worldwide Winner TobraDex," Internet Publication, <http://www.alconlabs.com/us/ aj/products/RxTher/TobraDexPro.jhtml> (Jun. 3, 2003).
Heier, J., et al., "Ketorolac tromethamine 0.5% ophthalmic solution in the treatment of moderate to severe ocular Inflammation after cataract surgery: a randomized, vehicle-controlled clinical trial," Am J Ophthalmol 127(3):253-9 (1999).
Alcon Laboratories, "Sterile Intraocular Irrigating Solution," Internet Publication, <http://www.alconlabs.comJca_en/aj/products/bss-pm 1.jhtml>(Jun. 26, 2003).
Wang, R.F., et al., "Effect of Oxymetazoline on Aqueous Flumor Dynamics and Ocular Blood Flow in Monkeys and Rabbits," Arch Ophthalmol 111:535-8 (1993) (Abstract only).
Chu, Teh-Ching, et al., "Oxymetazoline: Potential Mechanisms of Inhibitory Effects on Aqueous Humor Dynamics," Pharmacology 53:259-270 (1996).
Patil, Popat N., et al., "Antimuscarinic Action of Oxymetazoline on Human Intraocular Muscles," Journal of Ocular Pharmacology and Therapeutics 20(4):328-332 (2004).
Flach, A.J., et al., "Effectiveness of ketorolac tromethamine 0.5% ophthalmic solution for chronic aphakic and pseudophakic cystoid macular edema," Am J Ophthalmol 103(4):479-86 (1987).
Anderson, Janet A., et al., "Multiple Dosing Increases the Ocular Bioavailability of Topically Administered Flurbiprofen," Arch Ophthalmol 106: 1107-1109 (1988).
Ishikawa, H., et al., "Comparison of post-junctionai alpha-adrenoceptors in iris dilator muscle of humans, and albino and pigmented rabbits," Naunyn Schmeidebergs Arch Pharmacol 354(6):765-72 (1996).
Liou, Shiow-Wen, et al., "Maintenance of Mydriasis with One Bolus of Epinephrine Injection During Phacoemulsification," J Ocular Pharmacol Ther 17(3):249-253 (2001).
Lundberg, Bjorn, M.D., et al., "Intracameral mydriatics in phacoemulsification cataract surgery," J Cataract Refract Surg 29:2366-2371 (2003).
Flach, Allan J., "Cyclo-oxygenase Inhibitors in Ophthalmology," Survey of Ophthalmology 36(4):259-284 (1992).
Flach, A.J., et al., "The effect of ketorolac tromethamine solution 0.5% in reducing postoperative inflammation after cataract extraction and intraocular lens implantation," Ophthalmology 95(9): 1279-84 (1988).
Flach, Allan, J., "Corneal Meits Associated with Topically Applied Nonsteroidal Anti-Inflammatory Drugs," Tr Am Opth 99:205-212 (2001).
"The Pocket Oxford American Dictionary of Current English," Oxford University Press, New York, p. 418 (2002).
"The Bantam Medical Dictionary," Laurence Urdang Associates Ltd., Bantam Books, New York, p. 17 (1981).
Gills, J.P., "Intraocular irrigating solutions with cataract surgery," Atlas of Cataract Surgery, Masket, Samuel MD and Crandall, Alan S MD, eds. Chapter 3, Martin Dunitz Publisher (1999).
Gills, J.P., et al., Comment on "Bacterial endophthalmitis prophylaxis," Ophthalmology 110(8): 1668 (2003).
Gills, J.P., et al., "Effect of intracameral triamcinolene to control inflmmnation following cataract surgery," J Cataract Refract Surg 31(8):1670-1 (2005).
Gills, J.P., "My Method of Extracapsuiar Cataract Extraction With Implantation of a Posterior Chamber Intraocular Lens," Ophthalmic Surgery 16(6):386-392 (1985).
Hirowatari, Takeo, et al., "Evaluation of a New Preoperative Opthalmic Solution," Can J Ophthalmol 40:58-62 (2005).
Snyder, R.W., et al., "Acular as a single agent for use an an antimiotic and anti-inflammatory in cataract surgery," J. Cataract Refract Surg 26:1225-127 (2000).
Srinivasan, M.S., et al., "Topical ketorolac tromethamine 0.5% versus diclofenac sodium 0.1 % to inhibit miosis during cataract surgery," J Cataract Refract Surg 28:517-520 (2002).
Taber's Cyclopedic Medical Dictionary, 19th Edition, F.A. Davis Company, Philadelphia, pp. 1131-1132 (2003).
Eleftheriadis, H., et al., "Corneal toxicity secondary to inadvertent use of benzalkonium chloride preserved viscoelastic material in cataract surgery," British Journal of Ophthalmology 86:299-305 (2002).
Zaczek, A., et al., "The effect of phenylephrine on pain and flare intensity in eyes with uvitis," Acta Ophthalmologfca Scandinavica 78:516-518 (2000).
Online Merck Manual Home Edition articles entitled, "Inflammation," "Blepharitis," "Dacrocystitis," "Infections," "Gout," "Pseudogout," "Sinusitis," "Pharyngitis," "Reiter's Syndrome," "Tongue Disorders," "Meningitis," "Viral Infections," "Hemroids," "Urethritis," "Episcleritis," "Conjunctivitis," and "Rheumatoid Arthritis," <www.merck.com/mmhe/print/sec20/ch236/ch23 6d.html>, 51 pages, accessed Mar. 2007 (2003).
Medline Plus, Medical Encyclopedia: Neuroretinitis, Definition of "Neuroretinitis", <www.nlm.nih.gov/medlineplus/ency/article/002268.htm, accessed Mar. 2007>, (2005).
Kuby, J., "Immunology," Third Edition, W.H. Freeman and Company, New York, pp. 67 and 365-378, (1997).
Chaudhary, K.P., et al., "Preoperative Topical Flubiprofen-Na in Extracapsular Lens Extraction Role in Maintaining Intraoperative Pupillary Dilation," Ind. J Opthal. 40(4): 109-114 (1992).
Arshinoff, S.A., et aL, "Pharmacotherapy of Photorefractive Keratectomy," J Cataract Refract Surg 22:1037-1044 (1996).
Volpe, N, et al., "Single Dose Ondansetron for Prevention of Postoperative Nausea and Vomiting," Drug Invest 8(2):67-72 (1994).
Cherry, P.M.H., et al., "The Treatment of Pain Following Excimer Laser Photorefractive Keratectomy: Additive Effect of Local Anes-

(56) References Cited

OTHER PUBLICATIONS thetic Drops, Topical Diclofenac, and Bandage Soft Contact," Opthalmic Surg Lasers 27:S477-S480 (1996).
Gurbaxani, A., et al., "Intracameral phenylephrine to prevent floppy iris syndrome during cataract surgery in patients on tamsulosin," Eye 21:331-332 (2007).
Goyal, R., et al., "Randomised Controlled Trial of Ketorolac in the Management of Corneal Abrasions," Acta Ophthalmol. Scand. 79: 177-179 (2001).
Arshinoff, S., et al., "Use of Topical Nonsteroidal Anti-InfammatoryDrugs in Excimer Laser Photorefractive Keratectomy," J Cataract Refract Surg 20:216-222 (1994).
Busse, W., et al., "A Multicenter, Double-Blind; Randomized, PlaceboControlled Trial Comparing the Efficacy and Tolerability of Levocabastine-Oxymetazoline Nasal Spray with Levocabastine and Oxymetazoline Alone in the Symptomatic Treatment of Seasonal Allergic Rhinitis," American Journal of Rhinology 10(2): 105-111 (1996).
Quiroz, C., et al., "N.F. 12: A New Topical Solution for External Eye Disease," American Journal of Ophthalmology 41(6): 1020-1024 (1956).
Grahn, B., et al., "Diagnostic Ophthalmology," Can Vet J35:730-731 (1994).
Angra, S.K., et al., "Safe and Effective Management of Vernal Keratoconjunctivitis (VKC): A Double Blind Clinical Study," Ann Natl Acad Med Sci (India) 25(1):9-12 (1989).
Batra, D., et al., "Patterns of Responses to Alternative Medicines in Controlling Allergic Conjunctivitis," Ind. J. Ophthal 36(1): 17-21 (1988).
Matsuda, M., et al., "The Addition of Oxidized Glutathione to Intraocular Irrigating Solutions to Prevent Corneal Endothelial Damage During Intraocular Surgery," Folia Ophthalmol Jpn 41:1093-1098 (1990) Japanese language.
Matsuda, M., et al., "The Addition of Oxidized Glutathione to Intraocular Irrigating Solutions to Prevent Corneal Endothelial Damage During Intraocular Surgery," Folia Ophthalmol Jpn 41:1093-1098 (1990) English translation.
Nishide, T., et al., "Topical Anesthesia with Additional Intracameral Irrigation of 0.2% Lidocaine during Cataract Surgery in High Myopic Eyes," Jpn J Clin Ophthalmol 53(5):921-922 (1999) Japanese language.
Nishide, T., et al., "Topical Anesthesia with Additional Intracameral Irrigation of 0.2% Lidocaine during Cataract Surgery in High Myopic Eyes," Jpn J Clin Ophthalmol 53(5):921-922 (1999) English translation.
Kinoshita, A., "Mydriatic Efficacy of Irrigated Phenylephrine during Extracapsular Cataract Surgery," Folia Ophthalmol Jpn 40: 1730-1733 ( 1989) Japanese language.
Kinoshita, A., "Mydriatic Efficacy of Irrigated Phenylephrine during Extracapsular Cataract Surgery," Folia Ophthalmol Jpn 40: 1730-1733 (1989) English translation.
Tsuchisaka, H., "How to Use Surgical Adjuvents and Drugs in IOL Implantation," Journal of the Eye 4(6):755-759 (1987) Japanese language.
Tsuchisaka, H., "How to Use Surgical Adjuvents and Drugs in IOL Implantation," Journal of the Eye 4(6):755-759 (1987) English translation.
Lacy, C et al., "Drug Information Handbook," Lexi-Comp, Inc., Cleveland, Ohio, pp. 497 and 717-719, (1993).
Katsura, Hiroshi, "How to Use Local Anesthetic," Eye Clinic 27: I 055-1060 (1985). Japanese language.
Katsura, Hiroshi, "How to Use Local Anesthetic," Eye Clinic 27:1055-1060 (1985). English translation.
Sandoval, H.P., et al., "A review of the use of ketorolac tromethamine 0.4% in the treatment of post-surgical Inflammation following cataract and refractive surgery," Clin Ophthalmol 1(4):367-71 (2007).
Suleiman, Y.M., et aL, "Comparison of ketorolac tromethamine and prednisolone acetate in preventing surgically induced miosis during cataract surgery," Sultan Qaboos Univ Aled J 10(1):57-63 (2010).

Adrenalin [package insert]. JPH Pharmaceuticals, LLC, Rochester, MI; 2004.
Arshinoff: S.A., et al. (2009). The pharmacotherapy of cataract surgery. In Ophthalmology (M. Yanoff and J.S. Duker, Eds.) Third Edition. (pp. 434-440). Elsevier.
Batenburg, W., et al., "Carvedilol-induced antagonism of angiotensin II: a matter of a 1-adrenoceptor blockade," Journal of Hypertension, 24:1355-1363 (2006).
Behndig, A., et al., "Mydriatic response to different concentrations of intercameral phenylephrine in humans," J Cataract Reji-act 36: 1682-1686 (2010).
Bhattacharjee, AK., et al., "MMP-9 and EBA immunoreactivity after papaverine mediated opening of the blood-brain barrier," NeuroReport 13:2217-2221 (2002).
Fine, I.H., et al. (2009). Phacoemulsification in the presence of a small pupil. In Cataract Surgery: Axpert Consult (R. Steinert, Ed.) Third Edition (pp. 245-258). Elsevier.
Flach, A.J., et al., "Improvement in visual acuity in chronic aphakic and pseudophakic cystoid macuiar edema after treatment with topical 0.5% ketorolac tromethamine," Am J Ophthalmol 112:514-519 (1991).
Guzek, J.P., et al., "Risk factors for intraoperative complications in 1000 extracapsular cataract cases," Ophthalmology 94:461-466 (1987).
Ho, T., et al., "Maximal mydriasis evaluation in cataract surgery," J Cataract Refract Surg 18:375-379 (1992).
Hollo, G., "The side effects of the prostaglandin analogues," Expert Opin Drug Saf 6(1):45-52 (2007).
Kozlowska, H., et al., "Ligands at P2-, p3-, and the low-affinity state of P1-adrenoceptors block the a1-adrenoceptor-mediated constriction in human pulmonary and rat mesenteric arteries," J Cardiovasc Pharmacol 46(1):76-82 (2005).
Mamalis, N. (2009). Toxic anterior segment syndrome. In Cataract Surgery: Expert Consult (R. Steinert, Ed.) Third Edition. (pp. 589-594), Elsevier.
Demarinis, R.M., et al., "Structure-Activity Relationships for alpha-I Adrenergic Receptor Agonists and Antagonists," The alpha-I Adrenergic Receptors, Chapter 6, The Humana Press. 211-265 (1989).
Brown, M.R.W., et al., "The Preservation of Ophthalmic Preparations," J. Soc. Cosmetic Chemists 16:369-393 (1965).
Ellis, P.P. (1981). Basic considerations. In Ocular Therapeutics and Pharmacology (pp. 3-23) St. Louis:MO:The C.V. Mosby Company.
Physicians' Desk Reference for Ophthamology, 26th Edition, (pp. 1-2, 7-8, 15, 201, 209, 221-222, 235) (1998).
Reddy, LK. (Ed.), (1996). Ocular Therapeutics and Drug Delivery, (pp. 3-29, 171-193, 204, 377-404, 529-540.).
Millard, B.J., et al., "The stability of aqueous solutions of phenylephrine at elevated temperatures: identification of the decomposition products," J. Pharm. Pharmac. 25(Suppl.):24p-3 Ip (1973).
Omeros Corporation, "Safety, Efficacy and Pharmacokinetics of OMS302 in Subjects Undergoing Intraocular Lens Replacements With Phacoemulsification," Smart Patients, Inc. (2016).
Cochener, B., et al., "Intracameral Mydriasis: The New Standard Route for Cataract Surgery," Laboratoires Thea Satellite Symposium Barcelona Spain—XXXIII Congress of the ESCRS, Sep. 6, 2015.
Gupta, S.K., et al., "Phacoemulsification without preoperative topical mydriatics: induction and sustainability of mydriasis with intracameral mydriatic solution," Indian J Ophthalmol 62(3):333-336 (2014).
Shugar, J.K., "Lidocaine with bicarbonate lessens burning sensation on injection," Ocular Surgery News 16(1):13 (Jan. 1, 1998).
U.S. National Institute of Health, "Safety, Efficacy and Pharmacokinetics of OMS302 in Subjects Undergoing Intraocular Lens Replacement With Phacoemulsification," Clinical Trials Identifier NCT0157956. Oct. 10, 2012. Accessed at http://clinicaltrials.gov/archive/NCTI) 1579565/2012_10_10.
Sandoz, Inc., "Tropicamide—tropicamide solution/drops," Drug Label. Updated Jan. 5, 2016. Accessed at <https://dailvmed.nlm.nih. gov/dailymed/dmgInfo.cfrn?setid=52 I 592d1~53al-43 I 4-8b3f-d808f3hccfcd>.

(56) References Cited

OTHER PUBLICATIONS

Yoshitomi, T., et al. "Functional innervation and contractile properties of the human iris sphincter muscle," Exp. Eye Res. 46(6):979-986 (1988).
Yoshitomi, T., et al., "Adrenergic excitatory and cholinergic inhibitory innervations in the human iris dilator," Exp. Eye Res. 40(3):453-459 (1985).
Osher, R.H., et al., "OMS302 (phenylephrine and ketorolac injection) 1 %/0.3% to maintain intraoperative pupil size and to prevent postoperative ocular pain in cataract surgery with intraocular lens replacement," Expert Rev. Ophthalmol. 10(2):91-103 (2015).
Kumar, V., et al., "Systemic Absorption and Cardiovascular Effects of Phenylephrine Eyedrops," American Journal of Ophthalmology 99(2): 180-184 (1985).
Roberts, C.W., "Comparison of diclofenac sodium and flurbiprofen for inhibition of surgically induced miosis," J. Cataract Refract Surg 22(Supplement):780-787 (1996).
U.S. National Institute of Health, "Safety and Efficacy of OMS302 in Subjects Undergoing Intraocular Lens Replacement With Phacoemulsification (OMS302-ILR-003)," Clinical Trials Identifier: NCT01454063, Oct. 13, 2011. Accessed at <http://clinicaltrials.gov/ct2/shmv/study/NC TO 1454063?view=record>.
Food & Drug Administration, "Drug Standards Manual," Jan. 5, 2017. Accessed at http://www.fda.gov/Drugs/DevelopmentApprovalProcess/FormsSubmissionRequirements/ElectronicSubmissions/DataStandards.
Behndig, A., et al., "Evaluation of surgical performance with intracameral mydriatics in phacoemulsification surgery," Acta Ophthalmol Scand82(2):I44-I47 (2004).
Perry, H.D., et al., "An update on the use of ophthalmic ketorolac tromethamine 0.4%," Expert Opin Pharmacother. 7(1):99-107 (2006).
Lundberg, B., et al., "Separate and additive mydriatic effects of lidocaine hydrochloride, phenylephrine, and cyclopentolate after intracameral injection," J Cataract Refract Surg 32(2):280-283 (2008).
Akorn, Inc. (2005). AK-Dilate™ Phenylephrine Hydrochloride Ophthalmic Solution, USP 2.5%—Sterile. Buffalo Grove, IL. (Package Insert).
Allergan. (2001). Acular® (ketorolac tromethamine ophthalmic solution) 0.5% Sterile. Irvine, CA (Package Insert).
Phenylephrine Hydrochloride. (2012). In Medicines Support Unit for Optometrists. Retrieved from http://www.medsupport.org.uk/IntegratedCRD.nsf/b73d388be6b449968025768c0053 I3. (Package Insert).
Kim, S.J., et al., "Nonsteroidal anti-inflammatory drugs in ophthalmology," Surv. Ophthalmol. 55(2):108-133 (2010).
Raimann, M.H., et al., "Prophylactic timolol for the prevention of high intraocular pressure after cataract extraction. A randomized, prospective, double-blind trial," Ophthalmology 88(3):233-238 (1981).
Crandall, A.S., et al., "A comparison of patient comfort during cataract surgery with topical anesthesia versus topical anesthesia and intracameral lidocaine," Ophthalmology 106(1): 60-66 (1999).
Stewart, R., et al., "Efficacy and safety profile of ketorolac 0.5% ophthalmic solution in the prevention of surgically Induced miosis during cataract surgery," Clin. Ther. 21( 4):723-732 (1999).
Behndig, A., et al., "Aqueous humor lidocaine concentrations in topical and intracameral anesthesia," J Cataract Refract Surg 24(12): 1598-1601(1998).
Substantive Examination Adverse Report, issued Nov. 3, 2022 in corresponding Malaysian Application No. PI2020001054, filed on Oct. 23, 2013, 3 pages.
Third Substantive Examination Report, issued Apr. 19, 2022 in corresponding Mexican Application No. MX/a/2020/012591, filed on Apr. 22, 2015, 14 pages.
Notice of Reasons for Rejection mailed Mar. 2, 2022, issued in corresponding Japanese Application No. 2020-104619, filed Jul. 9, 2020, 3 pages.
Final Office Action mailed Sep. 30, 2022 in corresponding Japanese Application No. 2020-104619, filed Jul. 9, 2020, 5 pages.

Office Action, issued in corresponding Egyptian Application No. 2015040613, filed Apr. 21, 2015, 12 pages.
Office Action, issued in corresponding Costa Rican Application No. 2015-0233, filed Oct. 23, 2013, 23 pages.
Office Action mailed May 17, 2022, issued in corresponding Application No. AR 20130103855, filed Oct. 23, 2013, 11 pages.
U.S. National Institutes of Health, "Safety and Efficacy of OMS302 in Subjects Undergoing Intraocular Lens Replacement With Phacoemulsification," Clinical Trials Identifier: NCTO 1454063, May 1, 2012, Accessed at <https://clinicaltrials.gov/archive/NCT01454063/2012_05_01>.
Ling, T. L., et al., "Ocular bioavailability and tissue distribution of [14C]ketorolac tromethamine in rabbits," J Pharm Sci, 76(4): 289-294, (1987).
Donnenfeld, E. D., et al., "Preoperative ketorolac tromethamine 0.4% in phacoemulsification outcomes pharmacokinetic-response curve," J Cataract Refract Surg, 32(9): 1474-1482, (2006).
Andersen, L. J., et al., "Postoperative analgesia in total hip arthroplasty: a randomized double-blinded, placebo-controlled study on peroperative and postoperative ropivacaine, ketorolac, and adrenaline wound infiltration," Acta Orthop, 78(2): 187-192, (2007).
Ansel, H., et al., Pharmaceutical Dosage Forms and Drug Delivery Systems, 7th Ed. ed. Baltimore, Maryland: ippincott Williams & Wilkins (1999).
Attar, M., et al., "Ocular pharmacokinetics of 0.45% ketorolac tromethamine," Clin Ophthalmol, 4: 1403-1408, (2010).
Brocks, D.R., et al., "Clinical pharmacokinetics of ketorolac tromethamine," Clin Pharmacokinet, 23(6): 415-427, (1992).
Burstein, N. L., et al., "Corneal penetration and ocular bioavailability of drugs," J Ocul Pharmacol, 1(3): 309-326, (1985).
Davit, B. M., et al., "Comparing generic and innovator drugs: a review of 12 years ofbioequivalence data from the United States Food and Drug Administration," Ann Pharmacother, 43(10): 1583-1597, (2009).
Dousa, M., et al., "Drug-excipient compatibility testing-Identification and characterization of degradation products of phenylephrine in several pharmaceutical formulations against the common cold," J Pharm Biomed Anal, 55(5): 949-956, (2011).
El-Shibini, H., "The Stability of Phenylephrine" Arzneimittel-Forschung Drug Research, 19(4): 676-678, (1969).
El-Shibini, H., "The Stability of Phenylephrine," Arzneimittel-Forschung—Drug Research, 19(5): 828-831, (1969).
Fiscella, R. G., "Physical incompatibility of vancomycin and ceftazidime for intravitreal injection," Arch Ophthalmol, 111(6): 730, (1993).
Flach, A. J., et al., "Comparative effects of ketorolac 0.5% or diclofenac 0.1 % ophthalmic solutions on inflammation after cataract surgery," Ophthalmology, 105(9): 1775-1779, (1998).
Flynn, G. L., "Buffers—pH Control Within Pharmaceutical Systems," Journal of Parenteral Drug Association, 34(2): 139-163, (1980).
Fraunfelder, F. T. F., F.W., "Chapter 13—Drugs Used Primarily in Ophthalmology," Drug-Induced Ocular Side Effects, 5th Edition ed., 13: 531-628, (2001).
Frost, B. A., et al., "Safe preparation and administration of intravitreal bevacizumab injections," N Engl J Med, 365(23): 2238, (2011).
Gaglia, Jr., C., "Phenylephrine Hydrochloride," Analytical Profiles of Drug Substances, 3:483-512, (1974).
Gimbel, H., et al., "Intraocular availability and pupillary effect of flurbiprofen and indomethacin during cataract surgery," J Cataract Refract Surg, 22(4): 474-479, (1996).
Gorovoy, M., et al., "Recognizing and Treating Corneal Endothelial Disease," Ophthalmology Management, 4 pgs., (Jun. 2010).
Granero, G. E., et al., "Biowaiver monographs for immediate release solid oral dosage forms: furosemide," J Pharm Sci, 99(6): 2544-2556, (2010).
Guideline for Industry: Dose Response Information to Support Drug Registration, International Council for Harmonization of Technical Requirements for Pharmaceuticals for Human Use, pp. 1-15.
Lewis, R. J., Hawley's Condensed Chemical Dictionary, 15th Edition, ed. New York: John Wiley & Sons, Inc.; (2007).
Ho, T. T., et al., "Retinal complications of cataract surgery," Compr Ophthalmol Update, 7(1): 1-10, (2006).

(56) References Cited

OTHER PUBLICATIONS

Holland, S. P., et al., "Update on toxic anterior segment syndrome," Curr Opin Ophthalmol, 18(1): 4-8, (2007).
Van Hoonacker, A. E., Patrick, "Revisiting Silver Nanoparticle Chemical Synthesis and Stability by Optical Spectroscopy," Current Nanoscience, 2(3): 359-371, (2006).
Hughes, P. M. M., Ashim, K., "Chapter 1: Overview of Ocular Drug Delivery and Iatrogenic Ocular Cytopathologies," In: Ophthalmic Drug Delivery Systems 1st Edition Chapter 1: 1-28, (1993).
Jarvinen, K. J., T .; Urtti, A, "Ocular absorption following topical delivery," Advanced Drug Delivery Reviews, 16: 3-19, (1995).
Jensen, M. K., et al., "Crystallization on intraocular lens surfaces associated with the use of Healon GV," Arch Ophthalmol, 112(8): 1037-1042, (1994).
Killer, H. E., et al., "Corneal penetration of diclofenac from a fixed combination of diclofenac-gentamicin eyedrops," J Cataract Refract Surg, 24(10): 1365-1370, (1998).
Kim, E. K., et al., "Corneal endothelial damage by air bubbles during phacoemulsification," Arch Ophthalmol, 115(1 ): 81-88, (1997).
Knapp, A. J., et al., "Incompatibility of ketorolac tromethamine with selected postoperative drugs," Am J Hosp Pharm, 49(12): 2960-2962, (1992).
Komarowska, I., et al., "Retinal toxicity of commercially available intravitreal ketorolac in albino rabbits," Retina, 29(1): 98-105, (2009).
Lachman, L. L., Herbert A.; Kanig, Joseph, L., "Chapter 22: The Theory and Practice of Industrial Pharmacy," The Theory and Practice of Industrial Pharmacy, Philadelphia, Lea & Febiger, Chapter 22: p. 639-677, (1986).
Laughrea, P. A., et al., "Iatrogenic ocular silver nitrate burn," Cornea, 4(1): 47-50, (1985).
Lee, B. L., et al., "The solubility of antibiotic and corticosteroid combinations," Am J Ophthalmol, 114(2): 212-215, (1992).
Lee, V. H., et al., "Topical ocular drug delivery: recent developments and future challenges," J Ocul Pharmacol, 2(1): 67-108, (1986).
Macha, S. M., A.K., "Chapter 1: Overview of Ocular Drug Delivery," In: Ophthalmic Drug Delivery Systems, 2nd Edition, Chapter 1: 1-12, (2003).
Mahlberg, K., et al., "Compatibility of corticosteroids and antibiotics in combination," J Cataract Refract Surg, 23(6): 878-882, (1997).
Margalit, E., et al., "The safety of intraocular ketorolac in rabbits," Invest Ophthalmol Vis Sci, 47(5): 2093-2099, (2006).
Margalit, E., et al., "Use of intraocular ketorolac tromethamine for the treatment of chronic cystoid macular edema," Can J Ophthalmol, 45(4): 409-410, (2010).
Mian, S. I., et al., "Corneal ulceration and perforation with ketorolac tromethamine (Acular) use after PRK," Cornea, 25(2): 232-234, (2006).
Moses, G. S. K., M.S .; Ramachandraiah, A; Rao, K.M., "Spectral and Electrochemical Investigations of Ketorolac Tromethamine," Indian Journal of Chemistry, 42B: 159-165, (2003).
Naor, J., et al., "Anesthesia modalities for cataract surgery," Curr Opin Ophthalmol, 11(1): 7-11, (2000).
Nevyas, A S., et al., "Acute band keratopathy following intracameral Viscoat," Arch Ophthalmol, 105(7): 958-964, (1987).
Newton, D. W., "Drug incompatibility chemistry," Am J Health Syst Pharm, 66(4): 348-357, (2009).
Newton, D. W., "Physicochemical determinants of incompatibility and instability in injectable drug solutions and admixtures," Am J Hosp Pharm, 35(10): 1213-1222, (1978).
Newton, D. W., "Physicochemical Determinants of Incompatibility and Instability of Drugs for Injection and Infusion," In: Handbook on Injectable Drugs, 3rd Edition,, American Society of Hospital Pharmacists' Special Projects Division, (1983).
Ogut, M. S., et al., "Effects and side effects of mydriatic eyedrops in neonates," Eur J Ophthalmol, 6(2): 192-196, (1996).

Olejnik, O., "Chapter 9-Conventional Systems in Ophthalmic Drug Delivery," In: Ophthalmic Drug Delivery Systems, Chapter 9: 177-198, (1993).
Allergan Inc., "Acular LS (ketorolac tromethamine ophthalmic solution) 0.4% for topical use -Package Insert," 1-7, (2016).
Resume of Achim Hans-Peter Krauss, Ph.D., (2016).
Omeros Corporation, "Amendment After Non-Final Rejection filed Mar. 3, 2008," U.S. Appl. No. 10/630,626, pp. 1-14 (2008).
Lorente, R., et al., "Prevention of tamsulosin-associated IFIS with intracameral phenylephrine 1.5% in 250 eyes," J Emmetropia, 2: 59-63, (2011).
Omeros SEC Form S-1 (2008) (uploaded in three separate parts).
Physician's Desk Reference for OTC Products. p. 2, 7-8, 15, 209; 221-222, 235 (2003).
Papa, V., et al., "Topical naproxen sodium for inhibition of miosis during cataract surgery. Prospective, randomized clinical trials," Eye 16(3):292-296 (2002).
Gills, J.P., "Effect of lidocaine on lens epithelial cells," J Cataract Refract Surg 30: 1153-1154 (2004).
Gills, J.P., et al., "Unpreserved lidocaine to control discomfort during cataract surgery using topical anesthesia," J Cataract Refract Surg 23(4):545-550 (1997).
Zaczek, A, et al., "The effect of phenylephrine on pain and flare intensity in eyes with uvitis," Acta Ophthalmologica Scandinavica 78:516-518 (2000).
Shugar, J.K., "Intracameral Epinephrine for IFIS Prophylaxis," Cataract Refractive Surgery Today 72-74 (Sep. 2006).
Matsuda, M., et al., "The Addition of Oxidized Glutathione to Intraocular Irrigating Solutions to Prevent Corneal Endothelial Damage During Intraocular Surgery," Folia Ophthalmol Jpn 41:1093-1098 (1990). Japanese Language (Original).
Matsuda, M., et al., "The Addition of Oxidized Glutathione to Intraocular Irrigating Solutions to Prevent Corneal Endothelial Damage During Intraocular Surgery," Folia Ophthalmol Jpn 41:1093-1098 (1990). English translated copy.
Lundberg, B. et al., "Intracameral Mydriatics in Phacoemulsification Surgery Obviate the Need for Epinephrine Irrigation," Acta Ophthalmol. Scand 85:546-550 (2007).
Suleiman, Y.M., et al., "Comparison of ketorolac tromethamine and prednisolone acetate in preventing surgically Induced miosis during cataract surgery," Sultan Qaboos Univ Med J 10(1):57-63 (2010).
Behndig, A, et al., "Mydriatic response to different concentrations of intercameral phenylephrine in humans," J Cataract Refract 36: 1682-1686 (2010).
Nakamura, S., et al., "Evaluation of u1-adrenoceptors in the rabbit iris: pharmacological characterization and expression of mRNA," Br J Pharmacol 127:1367-1374 (1999).
Waitzman, M.B. "Prostaglandins and the eye," Metabolic, Pediatric and Systemic Ophthalmology 6: 17-26 (1982).
"Toxic Anterior Segement Syndrome After Acataract Surgery—Maine, 2006," A1A1WR Weekly 56(25):629-630 (2007), retrieved from <http://www.cdc.gov/mmwr/preview/mmwrhtml/mm5625a2. htm> on May 12, 2014.
Slack, J.W., et al., "A bisulfite-free intraocular epinephrine solution," Am. J. Ophthalmol. 110(1):77-82 (1990).
Allergan. (2011). Acuvail (ketorolac tromethamine ophthalmic solution) 0.45%. Irvine, CA. (Package Insert).
InterMed Medical Ltd. (2005) Neo-Synephrine® Phenylephrine Hydrochloride I% Injection. In Information for Helath Professionals Data Sheet.
Goodman & Gilman's the Pharmacological Basis of Therapeutics, Tenth Edition, McGraw-Hill, Eds., 2001. pp. 145-146, 687.
Lindstrom, R.L., et al., "Intracameral phenylephrine and ketorolac injection (OMS302) for maintenance of intraoperative pupil diameter and reduction of postoperative pain in intraocular lens replacement with phacoemulsification," Clin. Ophthalmol. 8: 1735-1744 (2014).
DeRuiter, Principals of Drug Action 2 at 4 (Fall, 2002), accessed Apr. 26, 2015 at www.auhum.eduF-derutja/nsaids2002.pdf.
Goodman & Gilman's, The Pharmacologic Basis of Therapeutics, 10th edition, pp. 145-146, 216-218, 687-692 (2001).
Ansari, H.R., et al., "Effects of prostaglandin F2al pha, latanoprost and carbachol on phosphoinositide turnover, MAP kinases, myosin

(56) References Cited

OTHER PUBLICATIONS light chain phosphorylation and contraction and functional existence and expression of FP receptors in bovine iris sphincter," Exp. Eye Res. 78(2):285-296 (2004).

Zanetti, F.R., "Effect of preoperative use of topical prednisolone acetate, ketorolac tromethamine, nepafenac and placebo, on the maintenance of intraoperative mydriasis during cataract surgery: a randomized trial," Indian J. Ophthalmol. 60(4):277-281 (2012).

Keulen-de Vos, H.C., et al., "Effect of indomethacin in preventing surgically induced miosis," Br. J. Ophthalmol. 67(2):94-96 (1983).

Guzinska, M., et al., "The effect of diclofenac sodium and indomethacin used locally for maintenance of pupillary dilatation during cataract surgery," Klin.Oczna 100(1):19-22 (1998). English Language, Abstract Included.

Guimaraes-Filho, S.R., et al., "Comparison of the anti-inflammatory effects of topically applied aspirin and Indomethacin following photocoagulation of the rabbit iris," Braz.I.Med.Biol.Res. 25(1):67-73 (1992).

Ahlquist, RP, "Present State of Alpha- and Beta-Adrenergic Drugs I The Adrenergic Receptor," Am Heart J. 92(5):661-4 (1976).

Gupta, V.P., et al., "Ketorolac tromethamine in the maintenance of intraoperative mydriasis," Ophthalmic Surg.Lasers 28(9):731-738 (1997).

Cutler Peck, C.M., et al., "Toxic anterior segment syndrome: Common causes," J Cataract Refract Surg 36: 1073-1080 (2010).

Gills, James, "Cataract Surgery Pharmacology—A leading surgeon shares several ways he's improved his medication protocol and raised his standard of care," Opthalmology Management, Sep. 2001. http://www.ophthalmologymanagement.com/articleviewer.aspx?articleid=8521 I.

Keates, R.H., et al., "The effect of topical indomethacin ophthalmic solution in maintaining mydriasis during cataract surgery," Ann. Ophthalmol. 16(12)1116-1121 (1984).

Notice of Reasons for Refusal dated Dec. 15, 2023, issued in corresponding Japanese Application No. 2023-012804, filed Oct. 23, 2013, 4 pages.

* cited by examiner

F1, G1
5mM Ketor/5mM Phen
NaPhosphate, pH 7.4
No Excipients or Additives

Related Substance Assay Results for F1, G1 pH7.4

| Time (months) | Phenylephrine % Related Substances | | | |
|---|---|---|---|---|
| | 2-8° C | 25° C | 40° C | 60° C |
| Pre Filtered | | 0.00 | | |
| Post Filtered | | 0.00 | | |
| 0 | | 0.00 | | |
| 0.5 | 0.00 | 0.00 | 0.00 | 0.00 |
| 1 | 0.00 | 0.00 | 0.00 | 0.21 |
| 2 | 0.00 | 0.00 | 0.00 | 2.26 |
| 3 | 0.00 | 0.00 | 0.25 | 1.74 |
| 4 | 0.00 | 0.00 | 0.40 | 2.68 |
| 6 | 0.00 | 0.21 | 1.22 | 5.64 |
| 9 | 0.00 | 0.00 | 0.29 | 8.85 |
| 12 | 2.09 | 1.36 | 1.90 | 16.97 |

Related Substance Assay Results for F1, G1 pH7.4

| Time (months) | Ketorolac % Related Substances | | | |
|---|---|---|---|---|
| | 2-8° C | 25° C | 40° C | 60° C |
| Pre Filtered | | 0.09 | | |
| Post Filtered | | 0.00 | | |
| 0 | | 0.09 | | |
| 0.5 | 0.08 | 0.08 | 0.00 | 0.00 |
| 1 | 0.00 | 0.00 | 0.00 | 0.09 |
| 2 | 0.00 | 0.00 | 0.00 | 0.67 |
| 3 | 0.00 | 0.00 | 0.00 | 0.74 |
| 4 | 0.00 | 0.00 | 0.23 | 1.12 |
| 6 | 0.00 | 0.21 | 0.66 | 3.51 |
| 9 | 0.00 | 0.05 | 0.36 | 2.65 |
| 12 | 0.00 | 0.00 | 0.64 | 3.30 |

FIG. 1

| F1, G2 |
| --- |
| 5mM Ketor/5mM Phen |
| NaPhosphate, pH 7.4 |
| EDTA |

Related Substance Assay Results for F1, G2 pH7.4

| Time (months) | Phenylephrine % Related Substances | | | |
| --- | --- | --- | --- | --- |
| | 2-8° C | 25° C | 40° C | 60° C |
| 0 |  | 0.00 |  |  |
| 0.5 | 0.00 | 0.00 | 0.00 | 0.00 |
| 1 | 0.00 | 0.00 | 0.00 | 0.00 |
| 2 | 0.00 | 0.00 | 0.00 | 0.36 |
| 3 | 0.00 | 0.00 | 0.00 | 1.17 |
| 4 | 0.00 | 0.00 | 0.50 | 1.82 |
| 6 | 0.00 | 0.00 | 0.77 | 2.85 |
| 9 | 0.00 | 0.00 | 0.47 | 2.70 |
| 12 | 0.99 | 1.01 | 1.38 | 5.19 |

Related Substance Assay Results for F1, G2 pH7.4

| Time (months) | Ketorolac % Related Substances | | | |
| --- | --- | --- | --- | --- |
| | 2-8° C | 25° C | 40° C | 60° C |
| 0 |  | 0.07 |  |  |
| 0.5 | 0.07 | 0.00 | 0.00 | 0.00 |
| 1 | 0.11 | 0.00 | 0.00 | 0.00 |
| 2 | 0.00 | 0.00 | 0.00 | 0.00 |
| 3 | 0.00 | 0.00 | 0.28 | 0.51 |
| 4 | 0.00 | 0.00 | 0.13 | 1.07 |
| 6 | 0.10 | 0.00 | 0.43 | 3.05 |
| 9 | 0.00 | 0.00 | 0.13 | 1.47 |
| 12 | 0.00 | 0.00 | 0.33 | 1.78 |

FIG. 2

F1, G3
5 mM Ketor/5 mM Phen
NaPhosphate, pH 7.4
EDTA + Na metabisulfite

Related Substance Assay Results for F1, G3 pH7.4

| Time (months) | Phenylephrine % Related Substances | | | |
|---|---|---|---|---|
| | 2-8° C | 25° C | 40° C | 60° C |
| 0 |  | 0.00 |  |  |
| 0.5 | 0.00 | 0.12 | 0.29 | 0.32 |
| 1 | 0.00 | 0.27 | 0.46 | 1.20 |
| 2 | 0.34 | 0.22 | 0.44 | 0.90 |
| 3 | 0.40 | 0.82 | 1.77 | 2.90 |

Related Substance Assay Results for F1, G3 pH7.4

| Time (months) | Ketorolac % Related Substances | | | |
|---|---|---|---|---|
| | 2-8° C | 25° C | 40° C | 60° C |
| 0 |  | 0.56 |  |  |
| 0.5 | 1.65 | 1.71 | 2.74 | 1.31 |
| 1 | 2.91 | 3.38 | 3.84 | 4.72 |
| 2 | 2.60 | 2.64 | 3.22 | 4.33 |
| 3 | 4.03 | 4.97 | 4.76 | 5.37 |

FIG. 3

F2, G1
5 mM Ketor/5mMPhen
NaCitrate, pH 6.5
No Excipients or
Additives

Related Substance Assay Results for F2 G1 pH6.5

| Time (months) | Phenylephrine % Related Substances | | | |
|---|---|---|---|---|
| | 2-8° C | 25° C | 40° C | 60° C |
| Pre Filtered | | 0.00 | | |
| Post Filtered | | 0.00 | | |
| 0 | | 0.00 | | |
| 0.5 | 0.00 | 0.00 | 0.00 | 0.00 |
| 1 | 0.00 | 0.00 | 0.00 | 0.44 |
| 2 | 0.00 | 0.00 | 0.00 | 0.00 |
| 3 | 0.00 | 0.00 | 0.00 | 0.15 |
| 4 | 0.22 | 0.00 | 0.33 | 0.32 |
| 6 | 0.00 | 0.00 | 0.87 | 3.24 |
| 9 | 0.00 | 0.00 | 0.48 | 1.97 |
| 12 | 0.27 | 0.00 | 0.93 | 5.53 |

Related Substance Assay Results for F2, G1 pH6.5

| Time (months) | Ketorolac % Related Substances | | | |
|---|---|---|---|---|
| | 2-8° C | 25° C | 40° C | 60° C |
| Pre Filtered | | 0.00 | | |
| Post Filtered | | 0.05 | | |
| 0 | | 0.00 | | |
| 0.5 | 0.09 | 0.00 | 0.00 | 0.00 |
| 1 | 0.00 | 0.00 | 0.00 | 0.20 |
| 2 | 0.00 | 0.00 | 0.00 | 0.49 |
| 3 | 0.00 | 0.00 | 0.00 | 0.61 |
| 4 | 0.17 | 0.33 | 0.00 | 1.72 |
| 6 | 0.00 | 0.00 | 0.41 | 1.99 |
| 9 | 0.00 | 0.00 | 0.18 | 1.99 |
| 12 | 0.00 | 0.00 | 0.25 | 2.32 |

FIG. 4

| F2, G2 |
| --- |
| 5mM Ketor/5 mM Phen |
| NaCitrate, pH 6.5 |
| EDTA |

Related Substance Assay Results for F2, G2 pH6.5

| Time (months) | Phenylephrine % Related Substances | | | |
| --- | --- | --- | --- | --- |
| | 2-8° C | 25° C | 40° C | 60° C |
| 0 | | 0.00 | | |
| 0.5 | 0.00 | 0.00 | 0.00 | 0.00 |
| 1 | 0.00 | 0.00 | 0.00 | 0.00 |
| 2 | 0.00 | 0.00 | 0.00 | 0.53 |
| 3 | 0.00 | 0.00 | 0.00 | 0.09 |
| 4 | 0.00 | 0.00 | 0.32 | 1.26 |
| 6 | 0.16 | 0.16 | 0.40 | 1.58 |
| 9 | 0.00 | 0.00 | 0.48 | 1.97 |
| 12 | 0.00 | 0.00 | 0.76 | 2.83 |

Related Substance Assay Results for F2, G2 pH6.5

| Time (months) | Ketorolac % Related Substances | | | |
| --- | --- | --- | --- | --- |
| | 2-8° C | 25° C | 40° C | 60° C |
| 0 | | 0.08 | | |
| 0.5 | 0.00 | 0.17 | 0.00 | 0.00 |
| 1 | 0.00 | 0.00 | 0.04 | 0.00 |
| 2 | 0.00 | 0.00 | 0.00 | 0.51 |
| 3 | 0.00 | 0.00 | 0.10 | 0.09 |
| 4 | 0.37 | 0.23 | 0.24 | 0.97 |
| 6 | 0.00 | 0.00 | 0.12 | 1.62 |
| 9 | 0.00 | 0.00 | 0.19 | 0.70 |
| 12 | 0.00 | 0.00 | 0.44 | 0.94 |

FIG. 5

F2, G3
5 mM Ketor/5 mM Phen
NaCitrate, pH 6.5
EDTA + Na metabisulfite

Related Substance Assay Results for F2. G3 pH6.5

| Time (months) | Phenylephrine % Related Substances | | | |
|---|---|---|---|---|
| | 2-8° C | 25° C | 40° C | 60° C |
| 0 | | 0.00 | | |
| 0.5 | 0.00 | 0.00 | 0.08 | 0.38 |
| 1 | 0.00 | 0.00 | 0.71 | 0.73 |
| 2 | 0.00 | 0.18 | 1.30 | 1.76 |

Related Substance Assay Results for F2G3 pH6.5

| Time (months) | Ketorolac % Related Substances | | | |
|---|---|---|---|---|
| | 2-8° C | 25° C | 40° C | 60° C |
| 0 | | 0.00 | | |
| 0.5 | 0.31 | 0.62 | 0.60 | 0.94 |
| 1 | 0.74 | 1.35 | 3.02 | 4.55 |
| 2 | 1.64 | 1.93 | 3.97 | 4.32 |

FIG. 6

F3, G1
5 mM Ketor/5 mM Phen
NaCitrate, pH 5.5
No Excipients or
Additives

Related Substance Assay Results for F3, G1 pH5.5

| Time (months) | Phenylephrine % Related Substances | | | |
|---|---|---|---|---|
| | 2-8° C | 25° C | 40° C | 60° C |
| Pre Filtered | | 0.00 | | |
| Post Filtered | | 0.00 | | |
| 0 | | 0.00 | | |
| 0.5 | 0.00 | 0.00 | 0.00 | 0.65 |
| 1 | 0.00 | 0.00 | 0.00 | 0.00 |
| 2 | 0.00 | 0.00 | 0.00 | 0.00 |
| 3 | 0.00 | 0.00 | 0.00 | 0.00 |
| 4 | 0.00 | 0.00 | 0.00 | 0.74 |
| 6 | 0.00 | 0.00 | 0.44 | 1.73 |
| 9 | 0.00 | 0.00 | 0.09 | 0.63 |
| 12 | 0.20 | 0.00 | 1.25 | 4.39 |

Related Substance Assay Results for F3, G1 pH5.5

| Time (months) | Ketorolac % Related Substances | | | |
|---|---|---|---|---|
| | 2-8° C | 25° C | 40° C | 60° C |
| Pre Filtered | | 0.00 | | |
| Post Filtered | | 0.00 | | |
| 0 | | 0.20 | | |
| 0.5 | 0.18 | 0.00 | 0.00 | 0.00 |
| 1 | 0.00 | 0.08 | 0.00 | 0.22 |
| 2 | 0.00 | 0.00 | 0.00 | 0.00 |
| 3 | 0.00 | 0.00 | 0.00 | 0.52 |
| 4 | 0.07 | 0.00 | 0.50 | 3.43 |
| 6 | 0.00 | 0.00 | 0.47 | 3.37 |
| 9 | 0.17 | 0.15 | 0.33 | 0.32 |
| 12 | 0.00 | 0.00 | 0.98 | 3.74 |

FIG. 7

F3, G2
5 mM Ketor/5 mM Phen
NaCitrate, pH 5.5
EDTA

Related Substance Assay Results for F3, G2 pH5.5

| Time (months) | Phenylephrine % Related Substances | | | |
|---|---|---|---|---|
| | 2-8° C | 25° C | 40° C | 60° C |
| 0 | | 0.00 | | |
| 0.5 | 0.00 | 0.00 | 0.00 | 0.00 |
| 1 | 0.00 | 0.00 | 0.00 | 0.00 |
| 2 | 0.00 | 0.00 | 0.00 | 0.52 |
| 3 | 0.00 | 0.00 | 0.00 | 0.00 |
| 4 | 0.00 | 0.00 | 0.00 | 1.04 |
| 6 | 0.00 | 0.00 | 0.13 | 1.74 |
| 9 | 0.00 | 0.05 | 0.35 | 2.17 |
| 12 | 0.00 | 0.14 | 0.45 | 4.28 |

Related Substance Assay Results for F3, G2 pH5.5

| Time (months) | Ketorolac % Related Substances | | | |
|---|---|---|---|---|
| | 2-8° C | 25° C | 40° C | 60° C |
| 0 | | 0.00 | | |
| 0.5 | 0.00 | 0.18 | 0.00 | 0.00 |
| 1 | 0.21 | 0.00 | 0.00 | 0.15 |
| 2 | 0.00 | 0.00 | 0.00 | 0.30 |
| 3 | 0.00 | 0.00 | 0.00 | 0.00 |
| 4 | 0.16 | 0.10 | 0.16 | 0.75 |
| 6 | 0.00 | 0.00 | 0.00 | 3.45 |
| 9 | 0.00 | 0.00 | 0.35 | 1.42 |
| 12 | 0.00 | 0.00 | 0.52 | 3.59 |

FIG. 8

F3, G3
5 mM Ketor/5 mM Phen
NaCitrate, pH 5.5
EDTA + Na metabisulfite

Related Substance Assay Results for F3, G3 pH5.5

| Time (months) | Phenylephrine % Related Substances | | | |
|---|---|---|---|---|
| | 2-8° C | 25° C | 40° C | 60° C |
| 0 | | 0.00 | | |
| 0.5 | 0.00 | 0.00 | 0.27 | 0.00 |
| 1 | 0.00 | 0.00 | 0.00 | 0.00 |
| 2 | 0.00 | 0.00 | 0.00 | 1.02 |

Related Substance Assay Results for F3, G3 pH5.5

| Time (months) | Ketorolac % Related Substances | | | |
|---|---|---|---|---|
| | 2-8° C | 25° C | 40° C | 60° C |
| 0 | | 0.00 | | |
| 0.5 | 0.00 | 0.04 | 0.26 | 1.03 |
| 1 | 0.12 | 0.15 | 0.67 | 3.44 |
| 2 | 0.00 | 0.64 | 2.48 | 3.59 |

FIG. 9

F4, G1
1 mM Ketor/1 mM Phen
NaCitrate, pH 4.5
No Excipients or
Additives

Related Substance Assay Results for F4, G1 pH4.5

| Time (months) | Phenylephrine % Related Substances | | | |
|---|---|---|---|---|
| | 2-8° C | 25° C | 40° C | 60° C |
| Pre Filtered | | 0.00 | | |
| Post Filtered | | 0.00 | | |
| 0 | | 0.00 | | |
| 0.5 | 0.00 | 0.00 | 0.16 | 0.70 |
| 1 | 0.00 | 0.00 | 0.00 | 1.06 |
| 2 | 0.15 | 0.13 | 0.82 | 3.09 |

Related Substance Assay Results for F4, G1 pH4.5

| Time (months) | Ketorolac % Related Substances | | | |
|---|---|---|---|---|
| | 2-8° C | 25° C | 40° C | 60° C |
| Pre Filtered | | 0.18 | | |
| Post Filtered | | 0.09 | | |
| 0 | | 0.00 | | |
| 0.5 | 0.13 | 0.00 | 0.00 | 0.00 |
| 1 | 0.00 | 0.00 | 0.00 | 0.00 |
| 2 | 0.00 | 0.00 | 0.11 | 1.03 |

FIG. 10

F4, G2
1 mM Ketor/1 mM Phen
NaCitrate, pH 4.5
EDTA

Related Substance Assay Results for F4, G2 pH4.5

| Time (months) | Phenylephrine % Related Substances | | | |
|---|---|---|---|---|
| | 2-8° C | 25° C | 40° C | 60° C |
| 0 |  | 0.00 |  |  |
| 0.5 | 0.00 | 0.09 | 0.00 | 0.42 |
| 1 | 0.00 | 0.00 | 0.00 | 0.52 |
| 2 | 0.14 | 0.00 | 0.68 | 2.34 |

Related Substance Assay Results for F4, G2 pH4.5

| Time (months) | Ketorolac % Related Substances | | | |
|---|---|---|---|---|
| | 2-8° C | 25° C | 40° C | 60° C |
| 0 |  | 0.07 |  |  |
| 0.5 | 0.00 | 0.00 | 0.00 | 0.00 |
| 1 | 0.00 | 0.00 | 0.00 | 0.15 |
| 2 | 0.00 | 0.00 | 0.00 | 0.40 |

FIG. 11

F4, G3
1 mM Ketor/1 mM Phen
NaCitrate, pH 4.5
EDTA + Na metabisulfite

Related Substance Assay Results for F4, G3 pH4.5

| Time (months) | Phenylephrine % Related Substances | | | |
|---|---|---|---|---|
| | 2-8° C | 25° C | 40° C | 60° C |
| 0 |  | 0.00 |  |  |
| 0.5 | 0.00 | 0.00 | 0.00 | 0.00 |
| 1 | 0.00 | 0.00 | 0.24 | 0.17 |
| 2 | 0.00 | 0.00 | 0.00 | 0.89 |

Related Substance Assay Results for F4, G3 pH4.5

| Time (months) | Ketorolac % Related Substances | | | |
|---|---|---|---|---|
| | 2-8° C | 25° C | 40° C | 60° C |
| 0 |  | 0.00 |  |  |
| 0.5 | 0.19 | 0.38 | 0.56 | 1.12 |
| 1 | 0.15 | 0.67 | 1.12 | 2.52 |
| 2 | 0.88 | 3.61 | 5.07 | 10.08 |

FIG. 12

| F2, G1 |
|---|
| 5 mM Ketor/5 mM Phen |
| NaCitrate, pH 6.5 |
| No Excipients or Additives |

| F2, G2 |
|---|
| 5 mM Ketor/5 mM Phen |
| NaCitrate, pH 6.5 |
| EDTA |

| Time Point | F2, G1 w/O2 Phenylephrine | | | | F2, G1 w/O2 Ketorolac | | | |
|---|---|---|---|---|---|---|---|---|
| | 4° C | 25° C | 40° C | 60° C | 4° C | 25° C | 40° C | 60° C |
| Day 0 | | 0.00 | | | | 0.00 | | |
| Day 14 | 0.00 | 0.00 | 0.00 | 0.00 | 0.00 | 0.00 | 0.00 | 0.00 |
| Day 28 | 0.00 | 0.00 | 0.00 | 0.00 | 0.00 | 0.00 | 0.00 | 0.12 |
| Day 60 | 0.00 | 0.00 | 0.00 | 1.46 | 0.00 | 0.00 | 0.06 | 1.79 |
| Day 90 | 0.47 | 0.36 | 0.25 | 0.60 | 0.77 | 0.64 | 0.53 | 0.80 |
| Day 120 | 0.00 | 0.00 | 0.18 | 3.20 | 0.11 | 0.07 | 0.14 | 2.18 |
| Day 180 | 0.00 | 0.00 | 0.58 | 6.38 | 0.00 | 0.00 | 0.25 | 2.84 |
| Day 270 | 0.15 | 0.16 | 0.63 | 9.60 | 0.00 | 0.00 | 0.19 | 3.43 |
| Day 365 | 2.61 | 0.70 | 1.71 | 15.85 | 0.00 | 0.03 | 0.34 | 4.17 |

| Time Point | F2, G2 w/O2 Phenylephrine | | | | F2, G2 w/O2 Ketorolac | | | |
|---|---|---|---|---|---|---|---|---|
| | 4° C | 25° C | 40° C | 60° C | 4° C | 25° C | 40° C | 60° C |
| Day 0 | | 0.00 | | | | 0.00 | | |
| Day 14 | 0.00 | 0.00 | 0.00 | 0.00 | 0.00 | 0.00 | 0.00 | 0.00 |
| Day 28 | 0.00 | 0.00 | 0.00 | 0.00 | 0.00 | 0.00 | 0.00 | 0.23 |
| Day 60 | 0.42 | 0.23 | 0.59 | 1.41 | 0.15 | 0.00 | 0.30 | 2.33 |
| Day 90 | 0.33 | 0.37 | 0.36 | 0.62 | 0.41 | 0.21 | 0.27 | 1.38 |
| Day 120 | 0.00 | 0.00 | 0.77 | 3.20 | 0.04 | 0.04 | 0.54 | 3.63 |
| Day 180 | 0.00 | 0.13 | 1.09 | 4.97 | 0.00 | 0.00 | 0.52 | 5.52 |
| Day 270 | 0.00 | 0.14 | 2.21 | 6.55 | 0.00 | 0.06 | 0.59 | 6.36 |
| Day 365 | 0.47 | 2.47 | 7.61 | 10.34 | 0.00 | 0.16 | 2.35 | 6.77 |

FIG. 13

| F2, G1 | F2, G2 |
|---|---|
| 5 mM Ketor/5 mM Phen<br>NaCitrate, pH 6.5<br>No Excipients or Additives | 5 mM Ketor/5 mM Phen<br>NaCitrate, pH 6.5<br>EDTA |

|  | F2, G1 w/N2 Phenylephrine | | | | F2, G1 w/N2 Ketorolac | | | |
|---|---|---|---|---|---|---|---|---|
| Time Point | 4° C | 25° C | 40° C | 60° C | 4° C | 25° C | 40° C | 60° C |
| Day 0 |  | 0.00 |  |  |  | 0.00 |  |  |
| Day 14 | 0.00 | 0.00 | 0.00 | 0.00 | 0.09 | 0.00 | 0.00 | 0.00 |
| Day 28 | 0.00 | 0.00 | 0.00 | 0.44 | 0.00 | 0.00 | 0.00 | 0.20 |
| Day 60 | 0.00 | 0.00 | 0.00 | 0.00 | 0.00 | 0.00 | 0.00 | 0.49 |
| Day 90 | 0.00 | 0.00 | 0.00 | 0.15 | 0.00 | 0.00 | 0.00 | 0.61 |
| Day 120 | 0.22 | 0.00 | 0.33 | 0.32 | 0.17 | 0.33 | 0.00 | 1.72 |
| Day 180 | 0.00 | 0.00 | 0.87 | 3.24 | 0.16 | 0.16 | 0.40 | 1.58 |
| Day 270 | 0.00 | 0.00 | 0.09 | 4.68 | 0.00 | 0.00 | 0.18 | 1.99 |
| Day 365 | 1.13 | 0.89 | 2.14 | 7.10 | 0.00 | 0.00 | 0.27 | 2.74 |

|  | F2, G2 w/N2 Phenylephrine | | | | F2, G2 w/N2 Ketorolac | | | |
|---|---|---|---|---|---|---|---|---|
| Time Point | 4° C | 25° C | 40° C | 60° C | 4° C | 25° C | 40° C | 60° C |
| Day 0 |  | 0.00 |  |  |  | 0.10 |  |  |
| Day 14 | 0.00 | 0.00 | 0.00 | 0.00 | 0.00 | 0.22 | 0.00 | 0.00 |
| Day 28 | 0.00 | 0.00 | 0.00 | 0.53 | 0.00 | 0.00 | 0.04 | 0.00 |
| Day 60 | 0.00 | 0.00 | 0.00 | 0.00 | 0.00 | 0.00 | 0.00 | 0.51 |
| Day 90 | 0.00 | 0.00 | 0.00 | 0.09 | 0.00 | 0.00 | 0.10 | 0.09 |
| Day 120 | 0.00 | 0.00 | 0.32 | 1.26 | 0.37 | 0.23 | 0.24 | 0.97 |
| Day 180 | 0.00 | 0.00 | 0.41 | 1.99 | 0.13 | 0.07 | 0.12 | 1.62 |
| Day 270 | 0.00 | 0.00 | 0.48 | 1.97 | 0.00 | 0.00 | 0.19 | 0.70 |
| Day 365 | 0.00 | 0.66 | 2.29 | 4.43 | 0.00 | 0.00 | 0.47 | 0.94 |

FIG. 14

F2, G2, A1
5 mM Ketor/5 mM Phen
NaCitrate, pH 6.5
EDTA+Ascorbic acid; no N2 overlay Related Substance Assay Results for f5/5_F2, G2, A1

| Time (months) | Phenylephrine % Related Substances | | | |
|---|---|---|---|---|
| | 2-8° C | 25° C | 40° C | 60° C |
| 0 | | 1.71 | | |
| 0.5 | 6.45 | 6.20 | 6.03 | 12.73 |
| 1 | 5.87 | 4.30 | 11.59 | 15.72 |

Related Substance Assay Results for f5/5_F2, G2, A1

| Time (months) | Ketorolac % Related Substances | | | |
|---|---|---|---|---|
| | 2-8° C | 25° C | 40° C | 60° C |
| 0 | | 0.74 | | |
| 0.5 | 20.69 | 27.61 | 24.13 | 43.65 |
| 1 | 20.54 | 23.31 | 26.53 | 37.17 |

FIG. 15

F2, G2, A2
5 mM Ketor/5 mM Phen
NaCitrate, pH 6.5
EDTA+Cysteine; no N2
overlay Related Substance Assay Results for f5/5_F2, G2, A2

| Time (months) | Phenylephrine % Related Substances | | | |
|---|---|---|---|---|
| | 2-8° C | 25° C | 40° C | 60° C |
| 0 |  | 0.00 |  |  |
| 0.5 | 0.00 | 0.00 | 0.57 | 24.16 |
| 1 | 0.00 | 0.00 | 3.85 | 25.24 |

Related Substance Assay Results for f5/5_F2, G2, A2

| Time (months) | Ketorolac % Related Substances | | | |
|---|---|---|---|---|
| | 2-8° C | 25° C | 40° C | 60° C |
| 0 |  | 0.00 |  |  |
| 0.5 | 0.00 | 0.00 | 9.78 | 38.77 |
| 1 | 0.00 | 2.05 | 20.47 | 56.81 |

FIG. 16

F2, G2, A3
5 mM Ketor/5 mM Phen
NaCitrate, pH 6.5
EDTA+Glutathione; no N2
overlay Related Substance Assay Results for f5/5_F2, G2, A3

| Time (months) | Phenylephrine % Related Substances | | | |
|---|---|---|---|---|
| | 2-8° C | 25° C | 40° C | 60° C |
| 0 | | 0.00 | | |
| 0.5 | 0.00 | 0.00 | 0.08 | 3.31 |
| 1 | 0.00 | 0.00 | 0.71 | 10.05 |

Related Substance Assay Results for f5/5_F2, G2, A3

| Time (months) | Ketorolac % Related Substances | | | |
|---|---|---|---|---|
| | 2-8° C | 25° C | 40° C | 60° C |
| 0 | | 0.00 | | |
| 0.5 | 0.00 | 0.00 | 1.90 | 16.08 |
| 1 | 0.72 | 1.20 | 8.21 | 34.62 |

FIG. 17

F2, G2, A4
5 mM Ketor/5 mM Phen
NaCitrate, pH 6.5
EDTA+Monothioglycerate; noN2 overlay Related Substance Assay Results for f5/5_F2, G2, A4

| Time (months) | Phenylephrine % Related Substances | | | |
|---|---|---|---|---|
| | 2-8° C | 25° C | 40° C | 60° C |
| 0 | | 0.00 | | |
| 0.5 | 0.00 | 0.00 | 1.72 | 9.50 |
| 1 | 0.00 | 0.51 | 2.76 | 5.77 |

Related Substance Assay Results for f5/5_F2, G2, A4

| Time (months) | Ketorolac % Related Substances | | | |
|---|---|---|---|---|
| | 2-8° C | 25° C | 40° C | 60° C |
| 0 | | 0.00 | | |
| 0.5 | 0.00 | 0.42 | 10.84 | 29.94 |
| 1 | 0.31 | 10.23 | 20.00 | 29.06 |

FIG. 18

Related Substance Assay Results for PE-f450; Lot 1050193

450 mM PE
NaCitrate, pH 6.5
No Excipients or Additives

| Time (months) | Phenylephrine Related Substances | | | | Total Related Substances | | | |
|---|---|---|---|---|---|---|---|---|
| | 4° C | 25° C | 30°C | 40°C | 4° C | 25° C | 30°C | 40°C |
| 0 | | 0.00 | | | | 0.00 | | |
| 0.5 | | | | | | | | |
| 1 | 0.00 | 0.00 | 0.00 | 0.00 | 0.00 | 0.00 | 0.00 | 0.00 |
| 2 | 0.00 | 0.00 | 0.00 | 0.00 | 0.00 | 0.00 | 0.00 | 0.00 |
| 3 | 0.00 | 0.00 | 0.00 | 0.01 | 0.00 | 0.00 | 0.00 | 0.01 |
| 4 | 0.01 | 0.00 | 0.00 | 0.06 | 0.01 | 0.00 | 0.00 | 0.06 |

FIG. 19

STABLE PRESERVATIVE-FREE MYDRIATIC AND ANTI-INFLAMMATORY SOLUTIONS FOR INJECTION

CROSS REFERENCE TO RELATED APPLICATIONS

The present application is a continuation of U.S. patent application Ser. No. 17/405,269, filed Aug. 18, 2021, which is a continuation of U.S. patent application Ser. No. 17/171,373, filed Feb. 9, 2021, now abandoned, which is a continuation of U.S. patent application Ser. No. 16/944,609, filed Jul. 31, 2020, now abandoned, which is a continuation of U.S. patent application Ser. No. 16/738,546, filed Jan. 9, 2020, now abandoned, which is a continuation of U.S. patent application Ser. No. 16/454,775, filed Jun. 27, 2019, now abandoned, which is a continuation of U.S. patent application Ser. No. 16/213,758, filed Dec. 7, 2018, now abandoned, which is a continuation of U.S. patent application Ser. No. 15/823,282, filed Nov. 27, 2017, now abandoned, which is a continuation of U.S. patent application Ser. No. 15/278,514, filed Sep. 28, 2016, now issued as U.S. Pat. No. 9,855,246, which is a continuation of U.S. patent application Ser. No. 14/721,151 filed May 26, 2015, now issued as U.S. Pat. No. 9,486,406, which is a continuation of U.S. patent application Ser. No. 14/061,039, filed Oct. 23, 2013, now issued as U.S. Pat. No. 9,066,856, which claims the benefit of U.S. Provisional Application No. 61/736,179 filed Dec. 12, 2012, and U.S. provisional Application No. 61/718,026, filed Oct. 24, 2012, priority from the filing dates of which are hereby claimed under 35 U.S.C. § 120.

I. FIELD OF THE INVENTION

The present invention relates to stable, preservative-free and antioxidant-free liquid pharmaceutical formulations of ketorolac and phenylephrine for injection into intraocular ophthalmologic irrigation solutions.

II. BACKGROUND OF THE INVENTION

Ophthalmologic surgery often requires the use of a physiologic irrigation solution to protect and maintain the physiological integrity of intraocular tissues. Examples of ophthalmologic surgical procedures typically requiring irrigation solutions include cataract extraction and lens replacement and refractive lens exchange procedures, corneal transplant procedures and vitreoretinal operations and trabeculectomy procedures for glaucoma. Throughout the intraocular surgery, a patient's pupil must be sufficiently dilated to permit a clear operative field and to limit the trauma that can be associated with the procedure.

Pupil dilation (mydriasis) is typically achieved by dilating the eye preoperatively by topical administration of a mydriatic agent. Preoperatively applied mydriatic agents that may typically be administered include sympathomimetics, such as alpha-1 adrenergic receptor agonists, and anticholinergic agents, such as anti-muscarinics. Anticholinergic agents may be selected when longer action is desired, because they provide both cycloplegia (paralysis of the ciliary muscle) and mydriasis, e.g., tropicamide exhibits a half-life of approximately 4-6 hours. However, for many procedures, alpha-1 adrenergics will be preferred because they provide mydriasis but not cycloplegia. Alpha-1 adrenergics are thus shorter acting, causing mydriasis during a surgical procedure and allowing the pupil to return to its normal state shortly after completion of the procedure.

During the surgery, as the tips of surgical tools are inserted into the anterior chamber of the eye, the iris sphincter muscle tends to constrict (miosis), reducing the window defined by the pupil. If pupil diameter is not maintained adequately throughout the procedure, the risk of injuring structures within the eye increases and the required operating time is often prolonged. Clinically significant reductions in pupil diameter are associated with an increase in procedure-related complications, including posterior capsule tears, retained lens fragments and vitreous leaks.

Many ophthalmologic surgeons may incorporate epinephrine into the intraocular irrigation solution to assist in the maintenance of pupil dilation. Toxic anterior segment syndrome (TASS) is an acute, noninfectious inflammation of the anterior segment of the eye. TASS is a serious complication that can be associated with anterior segment eye surgery, most commonly cataract surgery. Various contaminants have been implicated as causes of TASS. The use of epinephrine including preservatives in intraocular irrigation solutions is one of a number of factors that has been associated with incidences of TASS after cataract surgery. See, e.g., http://www.cdc.gov/mmwr/preview/mmwrhtml/mm5625a2.htm, accessed Jul. 9, 2012. Even "preservative-free" epinephrine, meaning epinephrine that does not include an antimicrobial agent, still includes sodium metabisulfite as an antioxidant, which has also been implicated by ophthalmologists as associated with potential toxicity to the corneal endothelium (Slack, et al., *A bisulfate free intraocular epinephrine solution*, Am J Ophthalmol.; 110(1):77-82 (1990)).

Phenylephrine is another alpha-1 adrenergic agent that is sometimes administered topically prior to surgery to promote mydriasis, but is not approved in the United States in a preservative- and antioxidant-free form for single-use injection. Examples of approved phenylephrine HCL solutions include either 0.01% benzalkonium chloride (AK-DILATE™ from Akorn, available in 2 ml and 5 ml plastic dropper bottles; from Falcon Pharmaceuticals and Alcon Laboratories in multi-use 3 ml and 5 ml dropper bottles) and a "preservative-free" formulation that does not include an antimicrobial preservative but that still includes 2 mg of sodium metabisulfite as an antioxidant (Neo-Synephrine® from InterMed Medical Ltd., available in a spray bottle).

It is also desirable to reduce postoperative pain and irritation for patient comfort. Because of this, patients may be treated preoperatively or postoperatively with a non-steroidal anti-inflammatory drug (NSAID). Although cataract surgery (for example) is typically not associated with a high degree of post-operative pain, there is a need to minimize the number of those patients in the minority who do experience more severe post-operative pain. This is significant both because such patients experience discomfort and may have concern that their procedure did not go well, and because patients may need to reexamined as a precaution to ensure that there is not a serious complication leading to the pain.

Various methods of delivery of ocular drugs, such as NSAIDs, are conventionally employed, each of which has limitations. These limitations may include corneal and conjunctival toxicity, tissue injury, globe perforation, optic nerve trauma, central retinal artery and/or vein occlusion, direct retinal drug toxicity, and systemic side effects. For example, topical medications applied drop-wise are frequently impeded in reaching a targeted ocular site due to the eye's natural protective surface. In many situations, a rather small percentage of the medication applied to the surface of the eye will actually reach the desired therapeutic site of action.

To achieve sufficient concentration of drug delivered to the back of the eye, drugs such as NSAIDs are frequently administered systemically at very high doses. These levels are necessary to overcome the blood-retina barrier that protects the back of the eye from selected drug molecules coming from the blood stream. For surgical procedures, injectable drug solutions are sometimes injected directly into the back of the eye. Subconjunctival and peribulbar periocular injections are used when higher local concentrations are needed and when drugs with poor penetration characteristics need to be delivered. Intracameral injections directly into the anterior chamber are used in cataract surgery.

Ketorolac is an NSAID that is commercially available in preserved form for ocular use. Acular® from Allergan is a ketorolac tromethamine solution that includes benzalkonium chloride 0.01% as a preservative, available in 3 ml and 6 ml dropper bottles. Bedford Laboratories also supplies ketorolac tromethamine in a concentrated form (15 mg or 30 mg in 1 mL or 60 mg or 300 mg in 10 mL) for injection for intravascular or intramuscular administration. Allergan supplies a preservative-free 0.45% ketorolac tromethamine ophthalmic solution, which is formulated with carboxymethylcellulose sodium, sodium chloride, sodium citrate dehydrate, in individual use vials under the tradename Acuvail®.

While intracameral injection provides a prompt method of achieving a concentration, it can be associated with corneal toxicity. However, this method suffers from the fact that these drugs are quickly removed by the eye's natural circulatory process. Thus, injectable solutions rapidly lose their therapeutic benefit, often necessitating frequent, large dose injections that can carry toxicity risks. Sustained release formulations, such as viscoelastic gels containing microcapsules, may be injected intraocularly for a longer duration of action. However, there may be some delay in reaching a local therapeutic concentration of drug. Hence, there exists a need for controlled methods of ocular delivery during ophthalmologic procedures.

Solutions that have been used in ophthalmologic surgical irrigation include normal saline, lactated Ringer's solution and Hartmann's lactated Ringer's solution, but these are not optimal due to potential unfavorable corneal and endothelial effects. Other aqueous solutions that include agents such as electrolytes, buffering agents for pH adjustment, glutathione and/or energy sources such as dextrose, better protect the tissues of the eye, but do not address other physiologic processes associated with surgery. One commonly used solution for ophthalmologic irrigation is a two part buffered electrolyte and glutathione solution disclosed in U.S. Pat. No. 4,550,022 to Garabedian et al., the disclosure of which is hereby expressly incorporated by reference. The two parts of this solution are mixed just prior to administration to ensure stability. These solutions are formulated with a goal of maintaining the health of ocular tissues during surgery.

Another example of a modified solution is disclosed in International PCT Application WO 94/08602 in the name of inventors Gan et al., the disclosure of which is hereby incorporated by reference. This application discloses the inclusion of a mydriatic agent, such as epinephrine, in ocular irrigation solutions. Still another example is provided by International PCT Application WO 95/16435 in the name of inventors Cagle et al., which discloses the inclusion of non-steroidal anti-inflammatory drugs (NSAIDs) in an ophthalmologic irrigation solution.

III. SUMMARY OF THE INVENTION

The present invention provides a sterile, preservative-free and antioxidant-free liquid formulation of a mydriatic agent, phenylephrine, and an anti-inflammatory agent, ketorolac, for injection. The formulation can be suitably injected into an intraocular irrigation carrier and used to irrigate ocular tissues during surgery. The formulation avoids the potential toxicity that may be associated with preservatives and antioxidants yet has adequate stability.

One embodiment of the invention provides a preservative-free and antioxidant-free sterile liquid pharmaceutical formulation including phenylephrine, ketorolac and a buffer system in an aqueous carrier, that is stable for at least six months when stored at a temperature of from 5+/−3° C. to 25+/−2° C. Preferably, the formulation is stable for a period of at least 24 months when stored at a temperature of from 5+/−3° C. to 25+/−2° C.

In one aspect of the invention, the buffer system is selected from a sodium phosphate buffer system and a sodium citrate buffer system. Preferably the buffer system is a sodium citrate buffer system, such as an about 20 mM sodium citrate buffer system. In another aspect of the invention, the formulation has a pH of from 5.8 to 6.8.

In another aspect of the invention, the formulation is contained within a single-use container, such as a vial that is closed with a closure through which an injection can be drawn and a pre-filled syringe.

A suitable formulation of the present invention includes from 46 to 76 mM phenylephrine and from 8.5 to 14 mM ketorolac, and as one example may contain about 60.75 mM phenylephrine and about 11.25 mM ketorolac. The formulations of the present invention may include phenylephrine and ketorolac at a molar ratio of from 1:1 to 13:1 phenylephrine to ketorolac, and suitably may include these agents at a molar ratio of from 3:1 to 10:1 phenylephrine to ketorolac.

Another embodiment of the invention provides a preservative-free and antioxidant-free sterile liquid pharmaceutical formulation including phenylephrine, ketorolac and a buffer system in an aqueous carrier, and an intraocular irrigation carrier into which the formulation is injected, such that after injection the phenylephrine is present at a concentration of from 30 to 720 μM and the ketorolac is present at a concentration of from 44 to 134 μM. In another aspect of the invention, after injection into an intraocular irrigation carrier the phenylephrine is present at a concentration of from 240 to 720 μM and the ketorolac is present at a concentration of from 10 to 270 μM.

Another embodiment of the invention provides a sterile liquid pharmaceutical formulation that consists essentially of phenylephrine, ketorolac and a buffer system in an aqueous carrier, wherein the formulation is stable for at least six months when stored at a temperature of from 5+/−3° C. to 25+/−2° C. Preferably, the formulation is stable for a period of at least 24 months when stored at a temperature of from 5+/−3° C. to 25+/−2° C.

In one aspect of the invention, the buffer system is selected from a sodium phosphate buffer system and a sodium citrate buffer system. Preferably the buffer system is a sodium citrate buffer system, such as an about 20 mM sodium citrate buffer system. In another aspect of the invention, the formulation has a pH of from 5.8 to 6.8.

In another aspect of the invention, the formulation is contained within a single-use container, such as a vial that is closed with a stopper through which an injection can be drawn and a pre-filled syringe.

Another aspect of the invention provides a sterile liquid pharmaceutical dosage form for injection, including phenylephrine, ketorolac, a buffer system and an aqueous carrier, packaged in a single-use container for injection.

In another aspect of the invention, a sterile liquid pharmaceutical formulation is provided that includes phenylephrine, ketorolac, a buffer system and an intraocular irrigation carrier, in which the phenylephrine is included at a concentration of from 30 to 720 µM and the ketorolac is included at a concentration of from 10 to 270 or preferably the phenylephrine is included at a concentration of from 90 to 720 µM and the ketorolac is included at a concentration of from 44 to 134 µM. This formulation may also be preservative-free and antioxidant-free.

Also disclosed is a method of preparing a preservative-free and antioxidant-free sterile liquid pharmaceutical formulation including phenylephrine, ketorolac and a buffer system in an aqueous carrier, that is stable for at least six months when stored at a temperature of from 5+/−3° C. to 25+/−2° C. Preferably, the formulation is stable for a period of at least 24 months when stored at a temperature of from 5+/−3° C. to 25+/−2° C.

Further disclosed is a method of preparing a sterile liquid pharmaceutical formulation including phenylephrine, ketorolac, a buffer system and an intraocular irrigation carrier, in which the phenylephrine is included at a concentration of from 30 to 720 µM and the ketorolac is included at a concentration of from 10 to 270 µM, or preferably the phenylephrine is included at a concentration of from 90 to 720 µM and the ketorolac is included at a concentration of from 44 to 134 µM. This formulation may also be preservative-free and antioxidant-free.

IV. BRIEF DESCRIPTION OF THE DRAWINGS

The present invention will now be described in greater detail, by way of example, with reference to the accompanying drawings in which:

FIGS. 1-12 provide the results of a study of the stability of phenylephrine and ketorolac combination formulations at different time points over a 12 month period when stored at controlled temperatures from 2-8° C. to 60° C., as determined by measurement of the percentage of related substances from degradation of the active pharmaceutical ingredients, with variables of concentration of the active pharmaceutical ingredient concentrations, different buffer systems, addition of the preservative EDTA and addition of the preservative EDTA plus the antioxidant sodium metabisulfite.

FIGS. 13-14 provide the results of a study evaluating the effect of a nitrogen overlay on the stability of two phenylephrine and ketorolac combination formulations, with or without the preservative EDTA, at different time points over a one year period when stored at controlled temperatures from 4° C. to 60° C.

FIGS. 15-18 provide the results of a study evaluating the effects of different antioxidants on the stability of a phenylephrine and ketorolac combination formulation at time points over a one month period after storing samples at temperatures ranging from 2-8° C. to 60° C.

FIG. 19 provides the result of a study evaluating the stability of a high concentration phenylephrine formulation over a four month time period when stored at temperatures from 4° C. to 40° C.

Figure 20B:
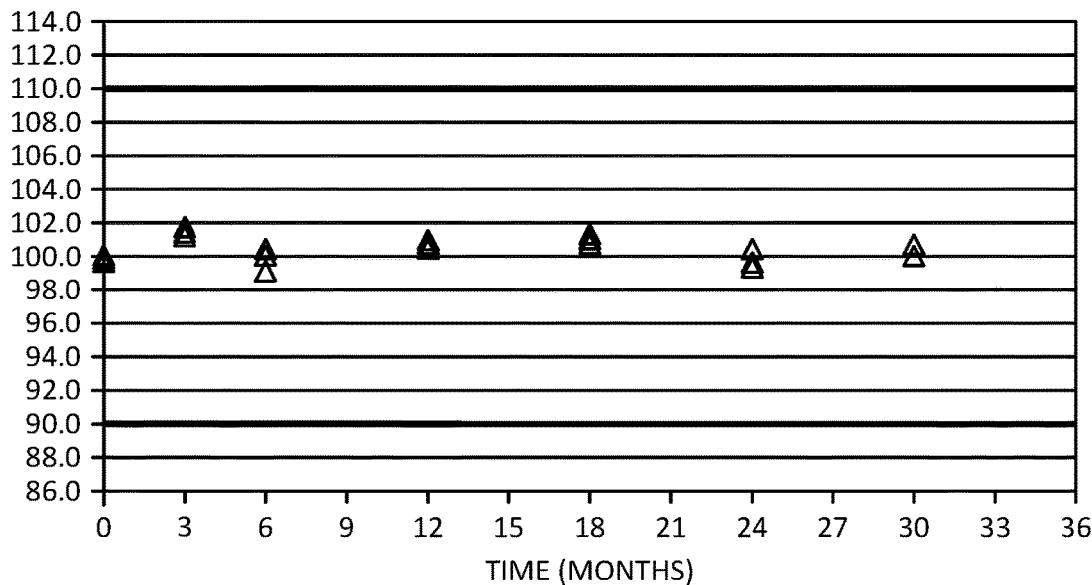

FIGS. 20A and 20B demonstrate the potency of phenylephrine and ketorolac, respectively, in phenylephrine and ketorolac combination formulation when stored for 30 months at 2-8° C.

FIGS. 21-25 illustrate the results of a non-human primate concentration-ranging efficacy study evaluating phenylephrine and ketorolac when given individually and when combined via intraocular irrigation in a balanced salt solution (BSS) during phacoemulsification lens extraction and exchange surgery, with measures of mydriasis (FIGS. 21 and 22) and flare (FIGS. 23-25) being observed.

Figure 21:
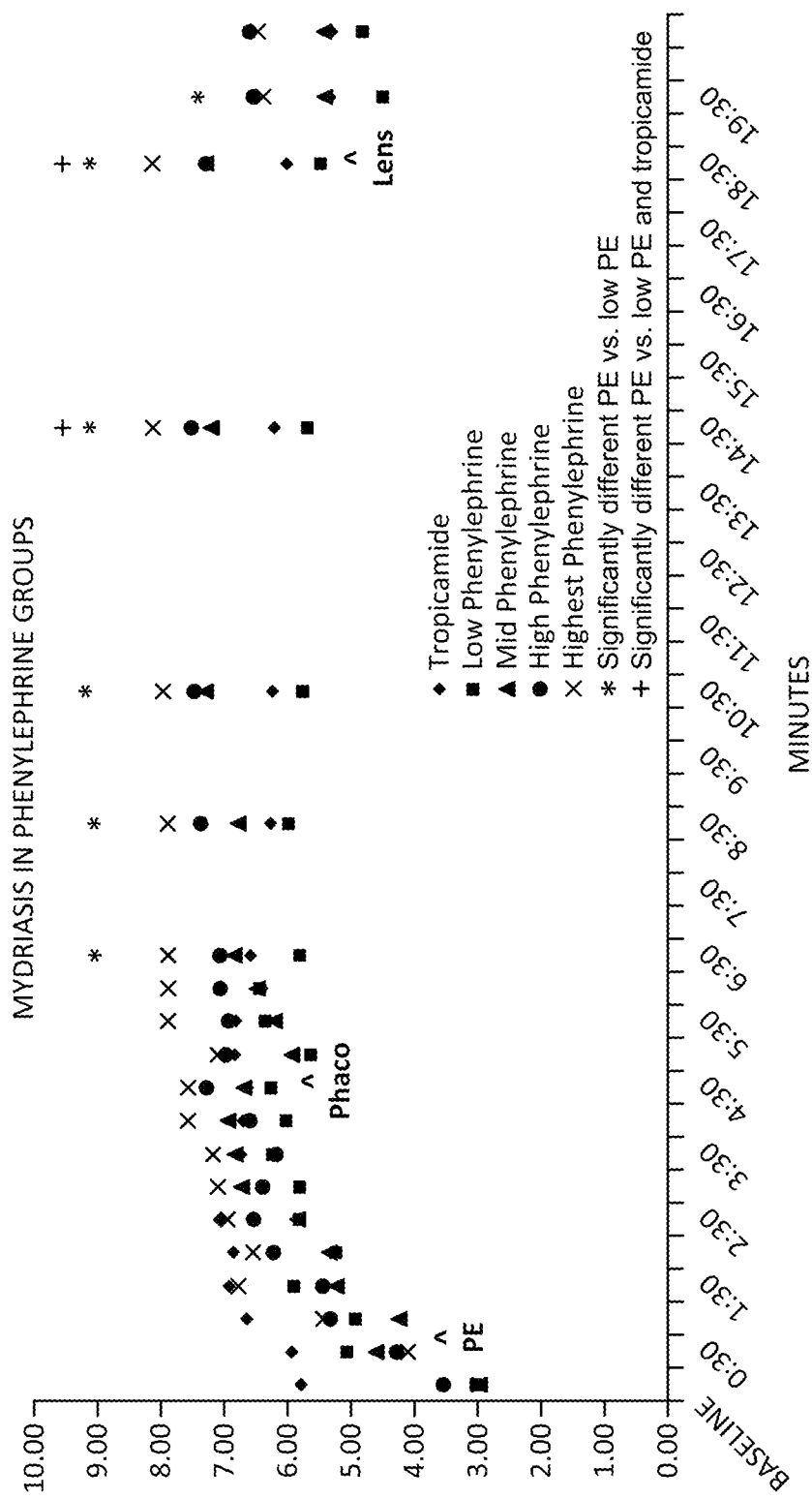

In FIG. 21, mean pupil diameter (mm) over time as measured from intraoperative video recordings are indicated for each treatment group (N=4, N=2 for the low and highest concentration phenylephrine groups). The time of initiation of anterior chamber perfusion with phenylephrine (PE), the initiation of phacoemulsification (Phaco) and placement of the posterior chamber intraocular lens (Lens) are additionally indicated. The interval during which the capsulorhexis and lens placement occurred, when irrigation was stopped, is not included on the timeline. Statistical significance was determined using a Student Newman-Keuls test, $\alpha=0.05$. df=23. N=2 for the low and highest PE groups.

Figure 22:
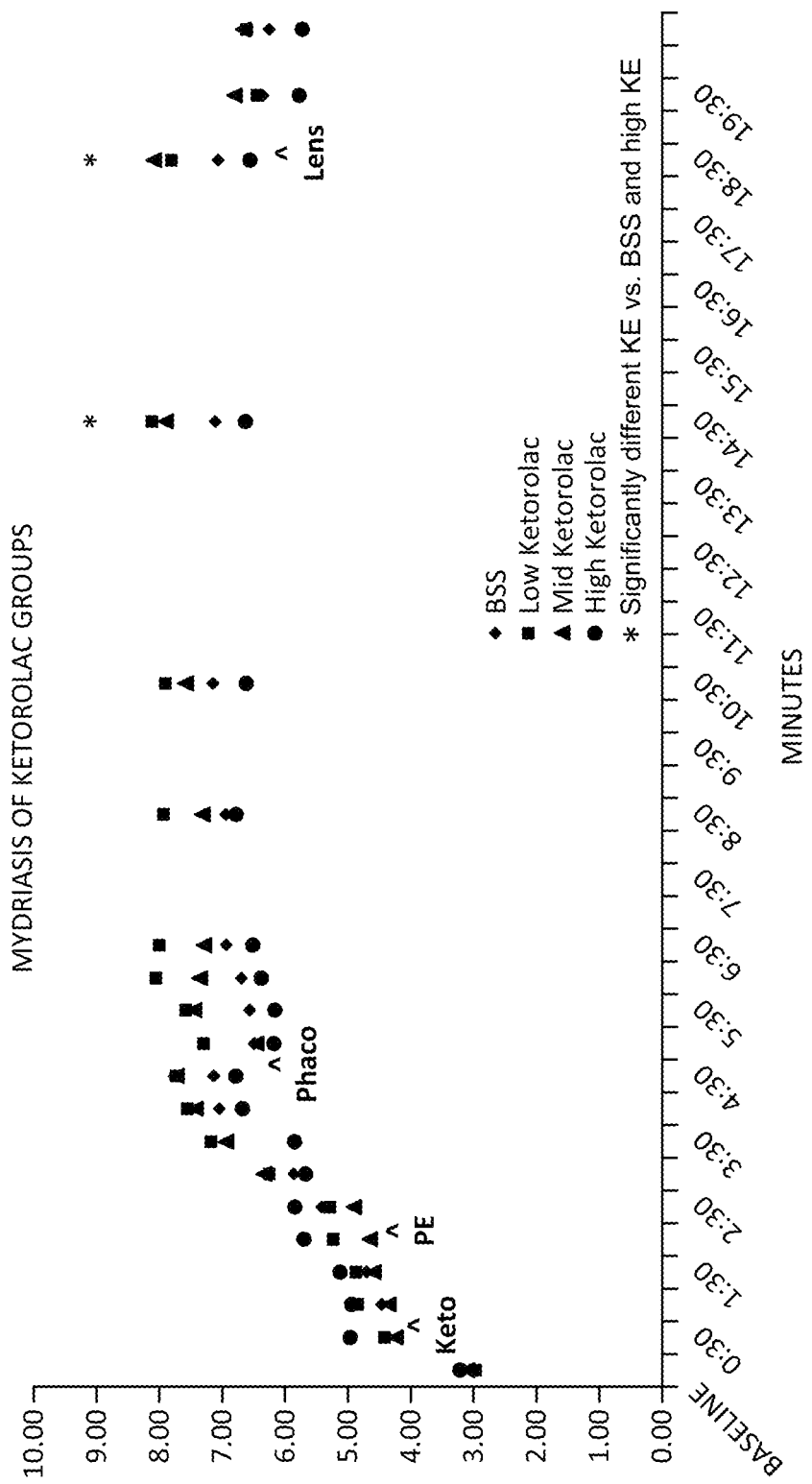

In FIG. 22, mean pupil diameter (mm) over time as measured from intraoperative video recordings are indicated for each treatment group (N=4). The time of initiation of anterior chamber perfusion with phenylephrine (PE), the initiation of phacoemulsification (Phaco) and placement of the posterior chamber intraocular lens (Lens) are additionally indicated. The interval during which the capsulorhexis and lens placement occurred, when irrigation was stopped, is not included on the timeline. Statistical significance was determined using a Student Newman-Keuls test, a=0.05=0.05, df=23), N=4 per group.

Figure 23:
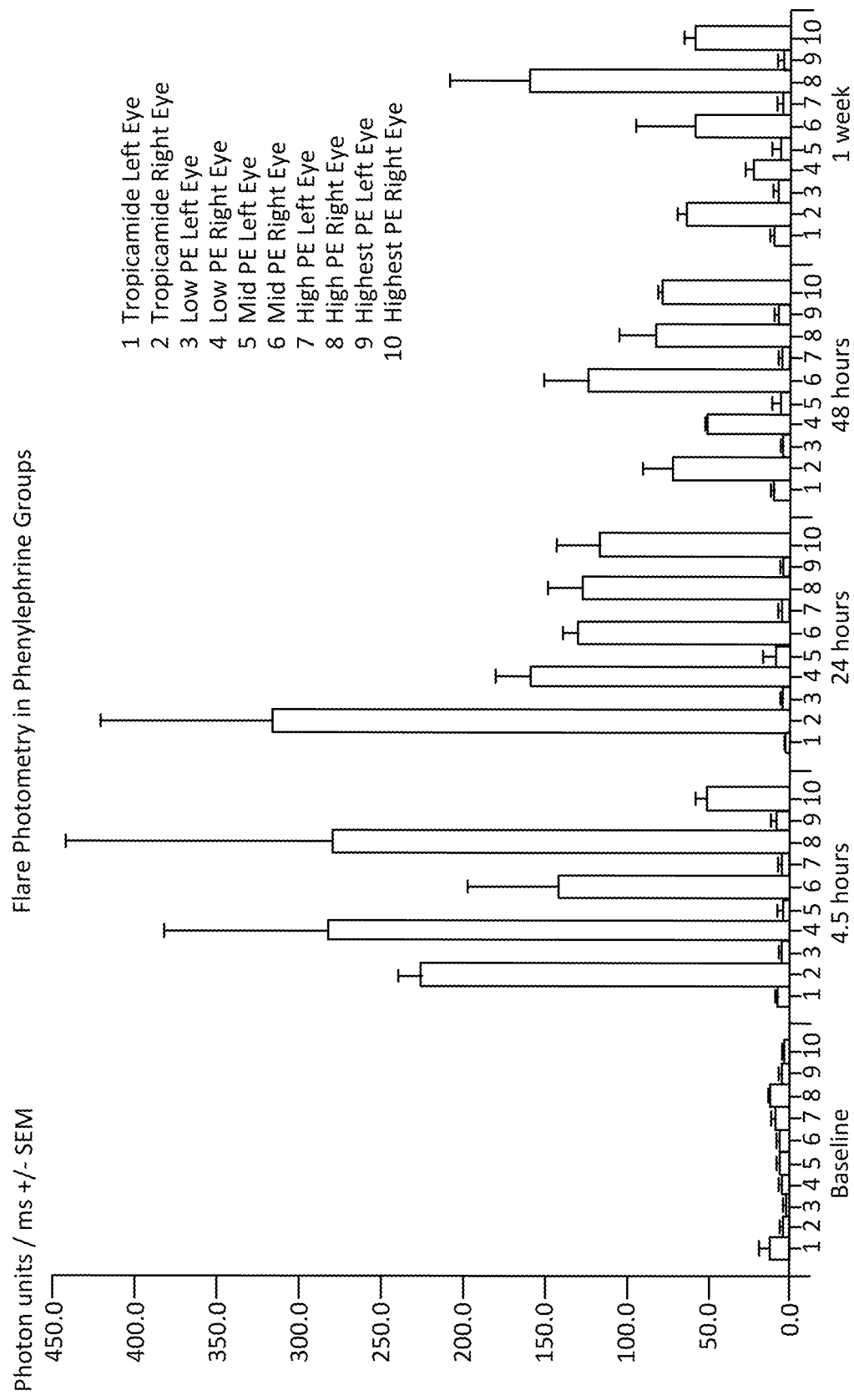

In FIG. 23, mean flare measures+/−the standard error for the control and treated eye in the phenylephrine treatment group. Means excluded the four eyes in the tropicamide control and high phenylephrine groups which received longer duration phacoemulsification (>45 secs). There was a significant effect of time on flare measures in all treatment groups (F=17.14, p<0.0001), reflecting the inflammatory response to the surgical intervention, but no significant difference between treatment groups when including or excluding the long duration phacoemulsification eyes. N=4 for tropicamide, mid and high PE groups. N=2 for the low and highest PE groups.

Figure 24:
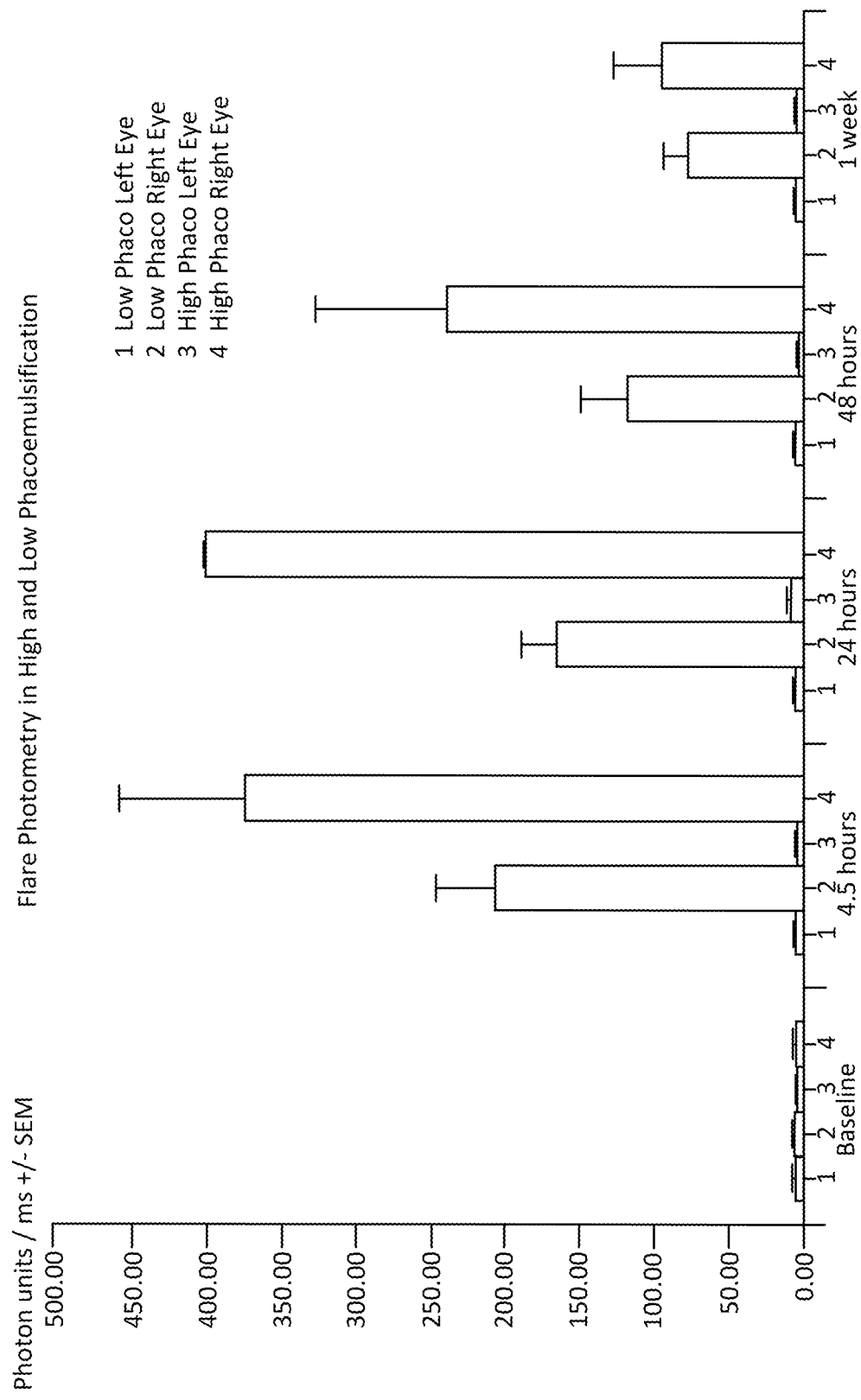

In FIG. 24, mean flare measures+/−the standard error for the phenylephrine and tropicamide treated eyes in the Phase 1 study that received either low phacoemulsification energy (<25 secs) or high phacoemulsification energy (>45 secs). Differences were significant evaluating across all time points (F=4.42, p<0.0018; Student Newman-Keuls test, $\alpha=0.05$, df=14; N=12 for the low phaco and 4 for the high phaco groups), indicating a correlation between phacoemulsification duration and flare photometer measures.

Figure 25:
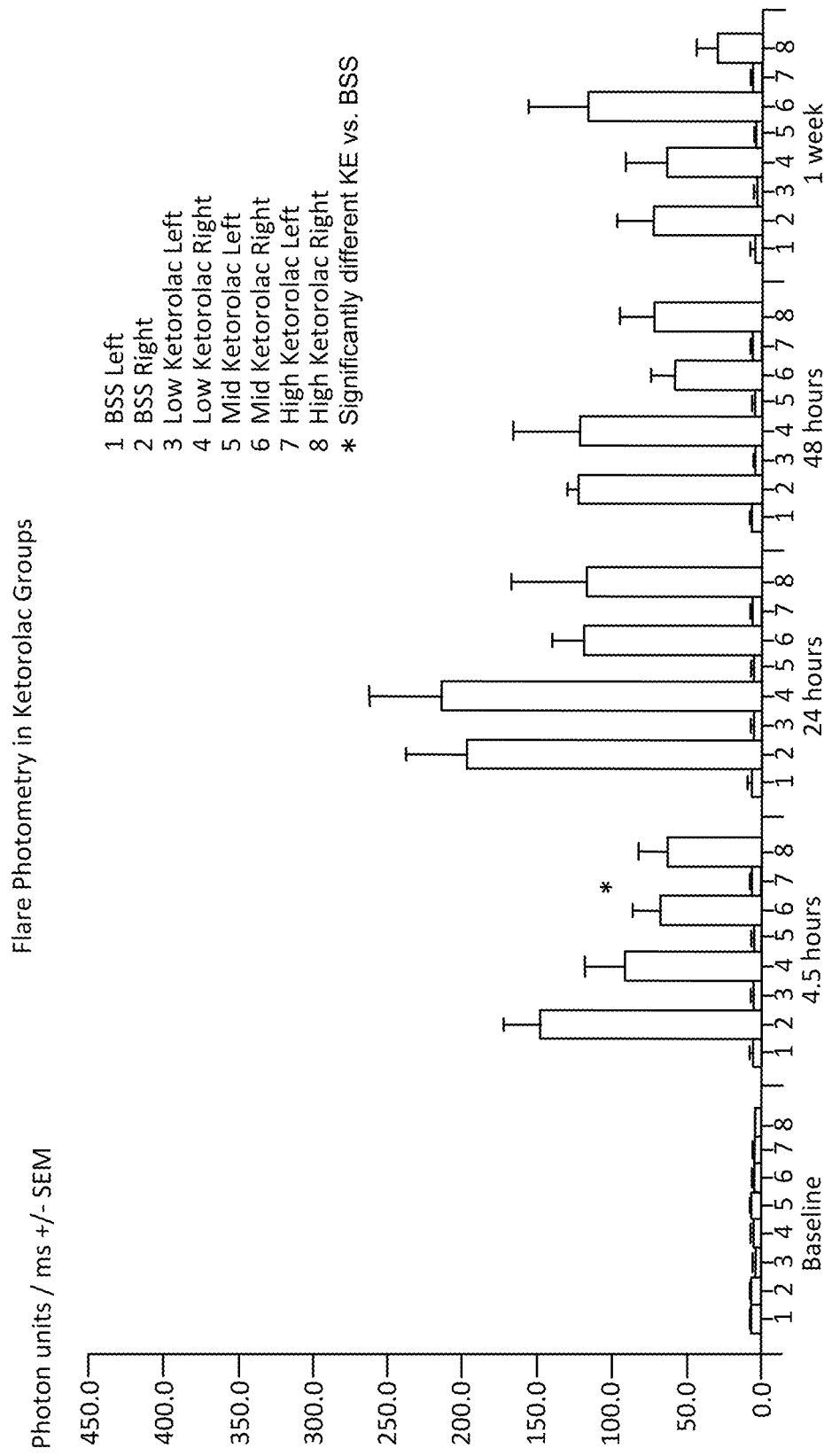

In FIG. 25, mean flare measures+/−the standard error for the control and treated eye in the ketorolac treatment group. Statistical significance was measured using a Student Newman-Keuls test, $\alpha=0.05$, df=13; N=4 per group; F=5.17, P<0.0223. The study was not sufficiently powered to reveal significance at any other time point.

Figure 26:
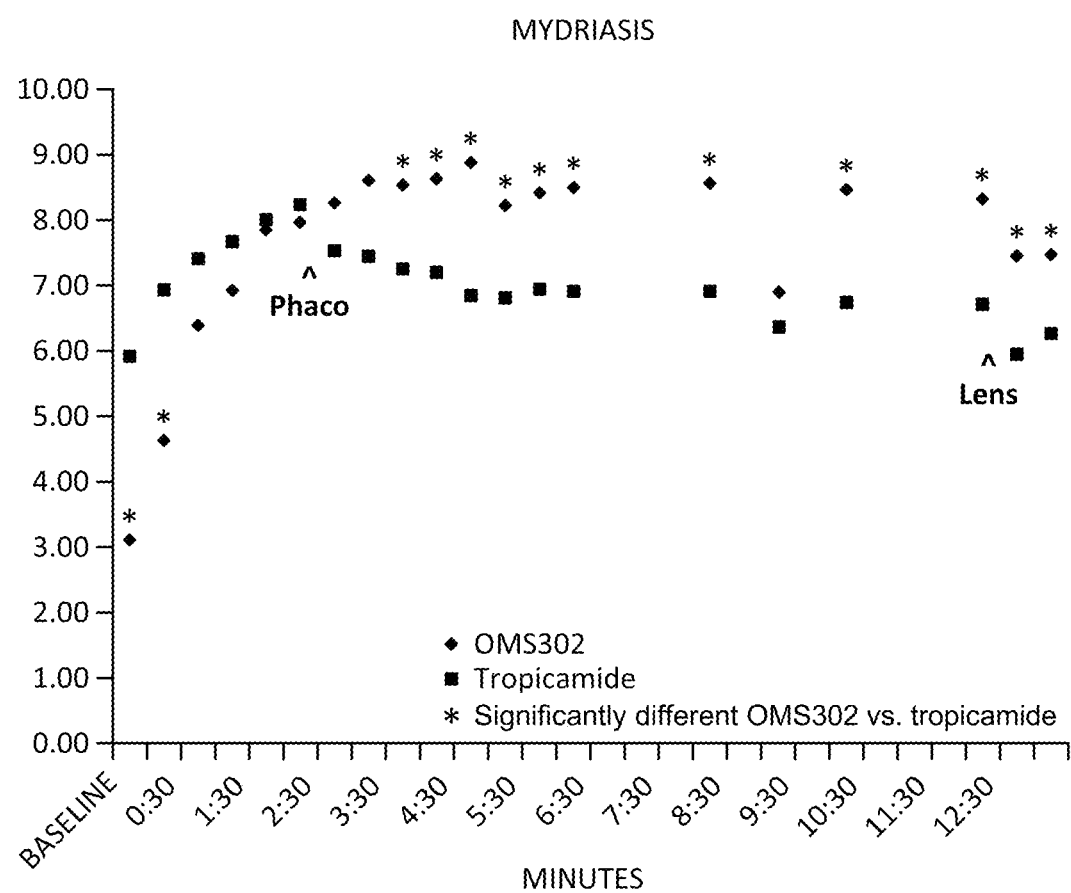
Figure 27:
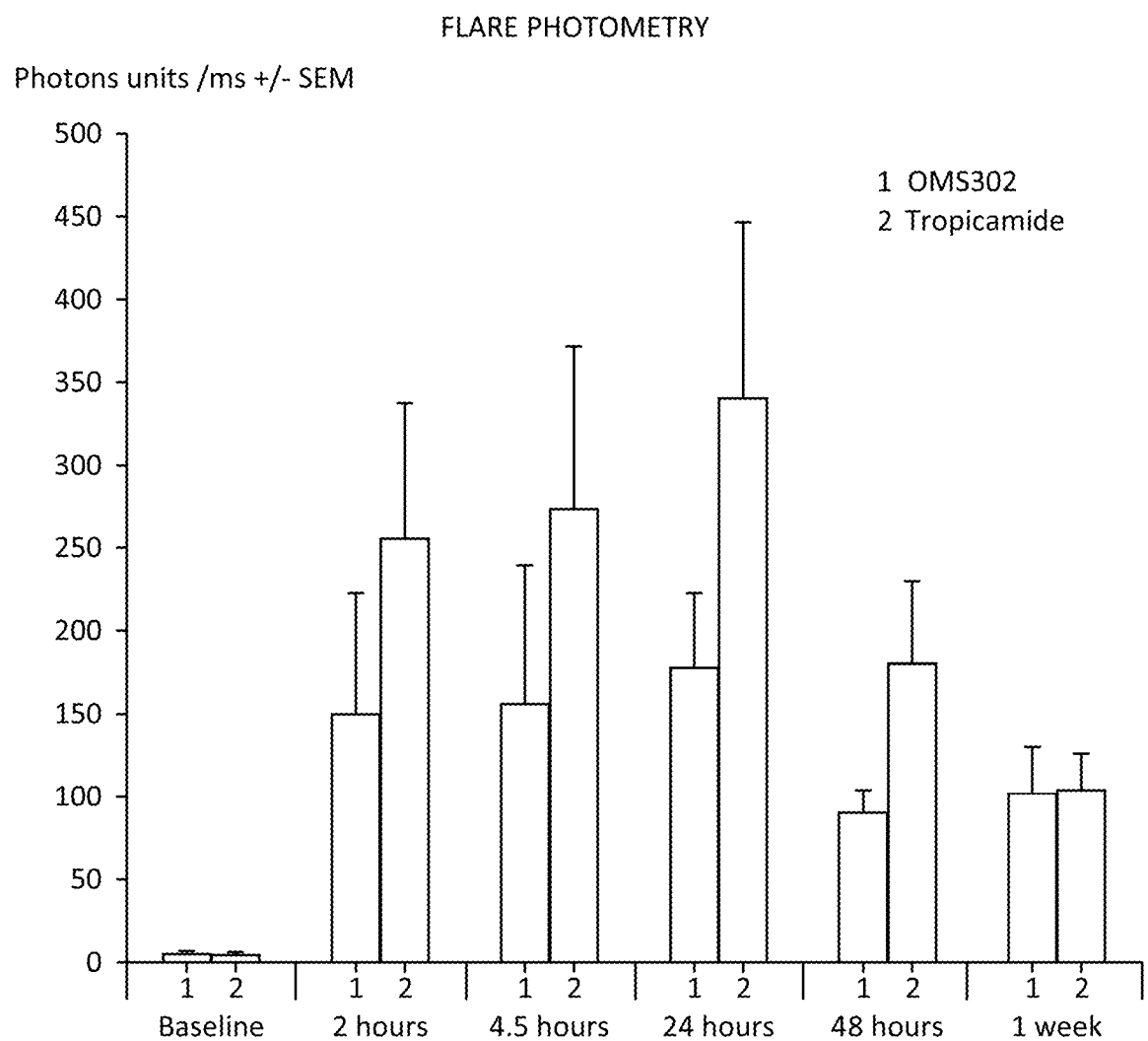
Figure 28:
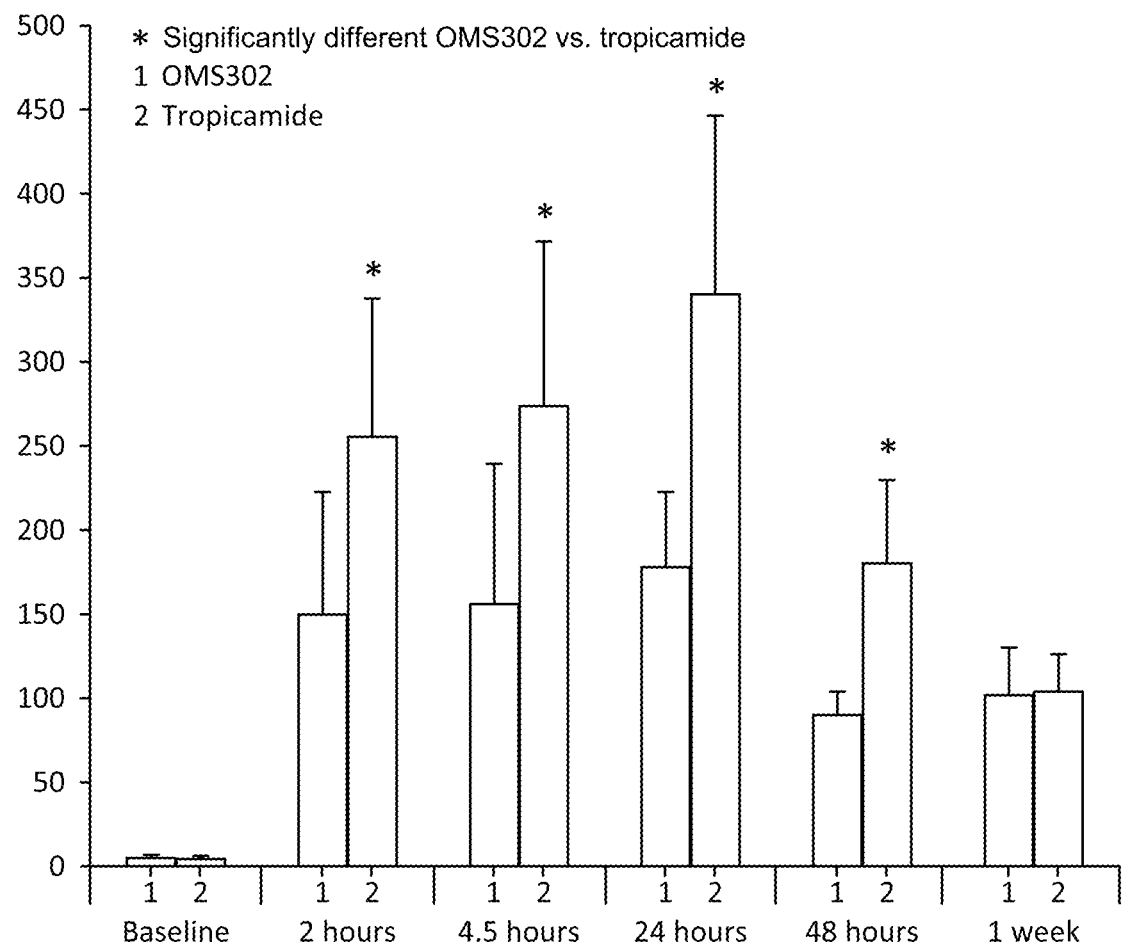

FIGS. 26-28 illustrate the results of a non-human primate study evaluating the effect of a phenylephrine and ketorolac combination formulation on mydriasis (FIG. 26) and flare (FIGS. 27-28) when delivered via intraocular irrigation in BSS during phacoemulsification lens extraction and exchange surgery.

In FIG. 26, mean pupil diameter (mm) over time as measured from intraoperative video recordings are indicated for each treatment group (N=7 per group). The time of initiation of phacoemulsification (Phaco) and placement of the posterior chamber intraocular lens (Lens) are additionally indicated. The interval during which the capsulorhexis and lens placement occurred, when irrigation was stopped, is not included on the timeline. Statistical significance was determined using a Student Newman-Keuls test, α=0.05, df=12.

In FIG. 27, mean flare measures+/−the standard error for the operative eye in the PE-KE (0M5302) and tropicamide control treatment groups. There was a significant effect of time on flare measures in both treatment groups (F=4.94, p<0.0008), reflecting the inflammatory response to the surgical intervention, but no significant difference between treatment groups at any time point when including all subjects (F=3.32, P<0.0935; Student Newman-Keuls test, α=0.05, df=12).

In FIG. 28, mean flare measures+/−the standard error for the operative eye in the PE-KE (OMS302) and tropicamide control treatment groups with the exclusion of subject X932, which exhibited limited phenylephrine induced dilation. There was a significant difference between treatment groups at 2, 4.5, 24 and 48 hours, indicated by * (F=3.32, P<0.0935 check stats p value; Student Newman-Keuls test α=0.05, df=12).

Figure 29:
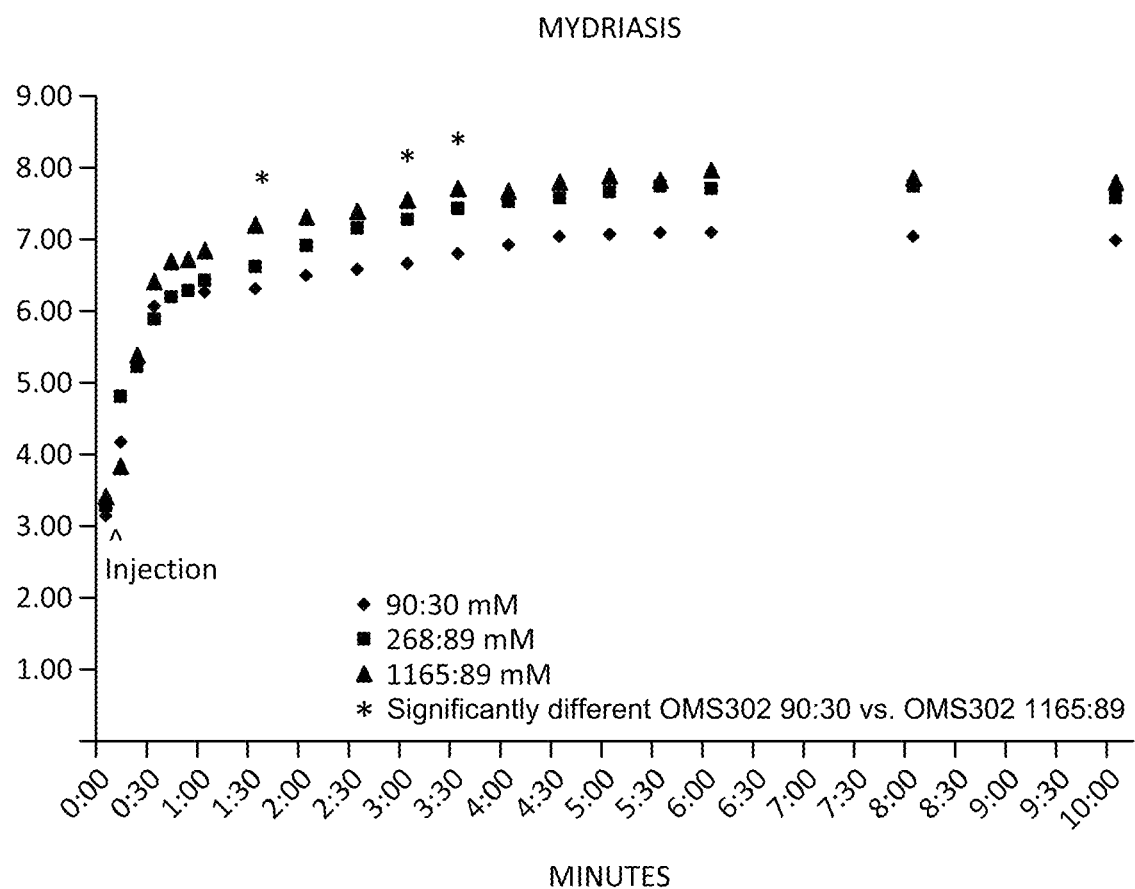

FIG. 29 illustrates the results of a dose-ranging study evaluating different concentrations of a phenylephrine and ketorolac combination formulation on mydriasis when delivered in BSS during phacoemulsification lens extraction and exchange surgery in a non-human primate. Mean pupil diameters (mm) over time as measured from intraoperative video recordings are indicated for each treatment group (N=4 per group). The time of intracameral administration (T=0:00 just after baseline measurements were obtained) is additionally indicated. Statistical significance was measured using a Student Newman-Keuls test, α=0.05, df=9. At all other time points between group differences were not significantly different by these criteria.

V. DETAILED DESCRIPTION

The present invention provides sterile formulations of irrigation solutions for perioperative local application to ocular tissues, including intraocular and topical application, that include phenylephrine as a mydriatic agent and ketorolac as an anti-inflammatory agent. These formulations are free of both preservatives and antioxidants, yet exhibit unexpectedly good stability. They are preferably packaged in single-use containers for injection and can be injected into a larger volume of an intraocular irrigation carrier prior to and used during intraocular procedures, such as cataract extraction and lens replacement and refractive lens exchange procedures.

Definitions

A "preservative" as used herein means an antimicrobial agent that is added to a pharmaceutical product to maintain stability and prevent decomposition by microbial growth. Common antimicrobial preservatives that may be included in a pharmaceutical compositions include sorbic acid and its salts, benzoic acid and its salts, calcium propionate, sodium nitrite (and sodium nitrate which converts to sodium nitrite "in situ"), sulfites (sulfur dioxide, sodium bisulfite, potassium hydrogen sulfite, etc.) and the metal chelator sodium ethylenediamine tetraacetic acid, also referred to as edetate disodium, EDTA or Nae EDTA.

An "antioxidant" as used herein refers to a substance that preferentially reacts with oxygen and thereby protects a pharmaceutical product to which it is added from degradation due to oxidation. Examples of water- or oil-soluble antioxidants that may be included in a pharmaceutical composition include sodium bisulphite, sodium sulphite, sodium metabisulphite, sodium thiosulphite, sodium formaldehyde sulphoxylate, 1- and d-ascorbic acid, acetylcysteine, cysteine, thioglycerol, thioglycollic acid, thiolactic acid, thieurea, dihithreitol, glutathione, propyl gallate, butylated hydroxyanisole, butylated hydroxytoluene, tertiary butyl hydroquinone, ascorbyl palmitate, nordihydroguaiaretic acid and alpha-tocopherol.

A "preservative-free" solution refers to a solution that does not include benzalkonium chloride or other antimicrobial agent.

An "antioxidant-free" solution refers to a solution that does not include sodium metabisulfite or other agent that has been included for the sole function or serving as an antioxidant, though an antioxidant-free solution may include a pH buffering system, one component of which may have antioxidant activity.

"Ketorolac" means ketorolac in a salt form, such as ketorolac tromethamine [(+/−)-5-Benzoyl-2,3-dihydro-1H-pyrrolizine-1-carboxylic acid:2-amino-2(hydroxymethyl)-1, 3-propanediol (1:1)].

"Phenylephrine" means phenylephrine in a salt form, such as phenylephrine HCL [(−)-m-Hydroxy-a-[(methyl amino) methyl]benzyl alcohol hydrochloride].

"Related substances" with respect to a given pharmaceutical ingredient refers to substances that result from degradation of the ingredient, expressed as a percentage of the total concentration of the pharmaceutical ingredient in the formulation. As used herein with respect to the present invention, "total related substances" refers to the total of all related substances resulting from degradation of the active pharmaceutical ingredients ketorolac and phenylephrine in the formulation, expressed as a percentage of the total concentration of the pharmaceutical ingredient in the formulation. Any related substance that is present at below the lower limit of quantitation, e.g., 0.1%, for the assay used to measure related substances is not included in the summation in determining total related substances. In the figures accompanying the examples herein, reference to a 0% related substances for an ingredient means that there were no related substances for the ingredient that were present at a level above the lower limit of quantitation, e.g., 0.1%, for the substance being assayed.

"Stable" refers to a liquid pharmaceutical formulation that, at the end of a specified storage period of time, contains less than 5% total related substances. In one embodiment, a stable liquid formulation is stable at a temperature from 5+/−3° C. (i.e., 2-8° C.) to 25+/−2° C. (i.e., 23-27° C.) for a period of at least six months. In a preferred embodiment, a stable liquid formulation is stable at a temperature from 5+/−3° C. to 25+/−2° C. for a period of at least one year. In a preferred embodiment, a stable liquid formulation is stable at a temperature from 5+/−3° C. to 25+/−2° C. for a period of at least 24 months. In a preferred embodiment, a stable liquid formulation is stable at a temperature from 5+/−3° C. to 25+/−2° C. for a period of at least 30 months. In a preferred embodiment of the invention, the stable formulations of the invention have less than 1.0% total related substances after a given storage period.

The term "about" is understood to mean that there can be variation in the concentration of a component of the described formulation that can be to 5%, 10%, 15% or up to and including 20% of the given value. For example, the phrase "a formulation having about 20 mM sodium citrate" is understood to mean that the formulation can have from 16 mM to 24 mM sodium citrate.

The term "sterile" refers to a pharmaceutical product that has been aseptically processed and that is devoid of viable bacteria, fungi or other microorganisms.

Pharmaceutical Agents

This invention provides stable, liquid preservative-free and antioxidant-free pharmaceutical formulations of a combination of two active pharmaceutical ingredients (APIs), phenylephrine as a mydriatic agent and the NSAID ketorolac as an anti-inflammatory agent.

Ketorolac

"Ketorolac" in the preferred formulation of the present invention is included as the ketorolac tromethamine salt [(+/−)-5-Benzoyl-2,3-dihydro-1H-pyrrolizine-1-carboxylic acid:2-amino-2(hydroxymethyl)-1,3-propanediol (1:1)]. Ketorolac is a member of the pyrrolo-pyrrole group of nonsteroidal anti-inflammatory drugs. Ketorolac HCL is a racemic mixture of the R-(+) and S-(−) enantiomers that may exist in three crystal forms, all of which are equally soluble in water. This agent discolors upon prolonged exposure to light, and accordingly light shielded packaging (e.g., overboxing or use of an amber vial) may be suitably utilized for packaging of formulations of the present invention.

Phenylephrine

"Phenylephrine" means phenylephrine in a salt form, such as phenylephrine HCL [(−)-m-Hydroxy-a-[(methyl amino) methyl]benzyl alcohol hydrochloride]. Phenylephrine is an alpha receptor sympathetic agonist. Phenylephrine HCl is freely soluble in water and alcohol.

Aqueous Carriers

The APIs are added to an aqueous solvent as a carrier, and the inventors have determined that no solubilizing agents are required. The aqueous carrier is suitably water for injection (WFI), which is a sterile, solute-free preparation of distilled water. Alternately, other aqueous carriers that are not harmful to intraocular tissues and which would not adversely affect the stability of the formulation may be used, such as deionized water, or, after first evaluating for potential impact on stability, saline or a balanced salt solution such as that described below.

Buffering Systems

The formulation of the present invention is adjusted to a pH from 5.8 to 6.8, and preferably to about 6.3. Sodium hydroxide and hydrochloric acid may be added as required to adjust the formulation to this pH. The desired pH is suitably maintained by use of a buffering system. One such suitable system is a citrate buffer, including citric acid monohydrate and sodium citrate dehydrate, and another suitable system is a sodium phosphate buffer, including dibasic sodium phosphate and monobasic sodium phosphate. Either buffer system may be used at an appropriate concentration in the range of 10 mM to 100 mM, and suitably may be 20 mM. As described below in Example 1, sodium citrate is a preferred buffer for use in a preservative-free formulation. The citric acid in the citrate buffer, which has the ability to chelate divalent cations and can thus also prevent oxidation, provides an antioxidant effect as well as a buffering effect. However, its presence does not degrade stability, as did other antioxidants (Example 3 below). As used herein, the term "antioxidant free" precludes the use of other antioxidants but does not preclude the use of a buffering agent, such as citric acid, that is included as part of the buffering system.

No Other Excipients

In a further aspect of the invention, in addition to being free of any preservatives or antioxidants, a formulation in accordance with the present invention also does not include any excipients other than the buffering system. For example, no solubilizing agents, such as ethanol or methanol, are used (i.e., the formulation is solubilizing-agent free.) Preferred formulations of the present invention consist essentially of the two APIs and the buffering system in water for injection, yielding a very pure formulation with reduced potential for toxicity to intraocular tissues.

Single-Use Containers

In a further aspect of the invention, the phenylephrine and ketorolac combination formulation of the present invention is contained in a quantity sufficient for a single-use during intraocular surgery in a container that facilitates such single-use and does not facilitate multi-use administration. Thus a sufficient quantity of drug composition formulated in accordance with the present invention, that is equal to or just slightly more (i.e., not more than 25% excess) than the amount of the drug composition desired to be added to a standard container of intraocular irrigation carrier, is contained within a single use container that facilitates dispensing of the drug composition by injection. For example, the desired single-use quantity of phenylephrine and ketorolac combination drug composition may be packaged in a glass vial closed with a stopper or other closure that includes a septum through which a hypodermic needle may be inserted to withdraw the drug composition, or may be packaged in a prefilled syringe. One example of a suitable container and closure system is a 5 mL USP Type 1 borosilicate flint glass vial with a West 20-mm gray butyl stopper and a 20-mm flip-off seal.

Before closing the container it may be desirable, based on the results described in Example 2 below, for the drug composition formulated in accordance with the present invention to be exposed to a nitrogen overlay (i.e., the displacement of air from the head space in the vial with nitrogen before sealing the vial). Other methods of evacuating air and displacing it with an inert gas may also be utilized, such as sparging an inert gas through the solution.

Intraocular Irrigation Carriers

The phenylephrine and ketorolac combination drug composition (i.e., combination drug product) is suitably added by injection into a bag, bottle or other container of an intraocular irrigation solution prior to administration by intraocular or topical irrigation or lavage. Suitable intraocular irrigation solutions include saline, lactated Ringer's, balanced salt solution or any other irrigation solution that is compatible with the aqueous formulation and not harmful to ocular tissues. One suitable intraocular irrigation carrier includes one or more, and preferably all, of the following adjuvants: sufficient electrolytes to provide a physiological balanced salt solution; a cellular energy source; a buffering agent; and a free-radical scavenger. One suitable solution (referred to in the examples below as a "balanced salt solution" or "BSS" includes: electrolytes of from 50 to 500 millimolar sodium ions, from 0.1 to 50 millimolar potassium ions, from 0.1 to 5 millimolar calcium ions, from 0.1 to 5 millimolar magnesium ions, from 50 to 500 millimolar chloride ions, and from 0.1 to 10 millimolar phosphate; bicarbonate as a buffer at a concentration of from 10 to 50 millimolar; a cellular energy source selected from dextrose and glucose, at a concentration of from 1 to 25 millimolar; and glutathione as a free-radical scavenger (i.e., antioxidant) at a concentration of from 0.05 to 5 millimolar.

One example of a suitable method of diluting and administering the combination drug composition of the present invention utilizes the formulation of the present invention described as Formula 2 in Table 2 below. An aliquot of 4.5 mL of this solution, including 4.0 mL as the intended quantity for single use and 0.5 mL of overfill, is contained within a sterile closed single-use vial and is intended for admixture with irrigation solution for administration during intraocular surgery. From the vial, 4 mL is withdrawn by syringe and mixed with 500 mL of BSS by injection into a 500 mL bag or bottle of BSS to provide a final concentration of 483 µM phenylephrine and 89 µM ketorolac in the irrigation solution for local delivery to the eye.

In another aspect of the invention, a sterile liquid pharmaceutical formulation for irrigation may be provided in which the phenylephrine and ketorolac is already admixed within an intraocular irrigation carrier, such that it has been diluted to the concentration of each active pharmaceutical ingredient desired for local delivery to intraocular tissues during surgery, and contained within a sterile bag, bottle or other single-use irrigation container. For example, such a formulation for irrigation may include phenylephrine at a concentration of from 30 to 720 µM and ketorolac at a concentration of from 10 to 270 µM, or preferably may include the phenylephrine at a concentration of from 90 to 720 µM and the ketorolac at a concentration of from 44 to 134 µM. In one embodiment, the phenylephrine and ketorolac combination is admixed within a balanced salt solution, such as that described above, as the intraocular irrigation carrier. This pharmaceutical formulation for irrigation may suitably be totally preservative-free and antioxidant-free, or optionally may include only an anti-oxidant that is typically included in the non-medicated intraocular irrigation carrier, such as the glutathione in the balanced salt solution described above, but no preservative.

Exemplary Formulations

As described above, the stable, liquid pharmaceutical formulations of the present invention include phenylephrine and ketorolac in a buffered aqueous carrier. Suitable concentrations of phenylephrine in the combination drug compositions of the present invention range from 10 mM to 500 mM, and preferably from 45 mM to 112 mM. Suitable concentrations of ketorolac in the combination drug compositions of the present invention range from 2 mM to 75 mM, and preferably from 8.5 mM to 24 mM. The buffer system, such as a sodium citrate buffer system, is suitably included at a concentration of from 10 to 100 mM, and preferably at about 20 mM. Two exemplary formulations in accordance with the present invention are set forth in Tables 1 and 2 below. In each case, sodium hydroxide and/or hydrochloric acid may be added when preparing the formulation if necessary to adjust the pH to about 6.3.

TABLE 1

Example Formulation 1

| Component (USP) added to water for injection | Preferred Concentration | | Suitable Concentrations | | Representative Diluted Dosing Concentration (µM) | |
|---|---|---|---|---|---|---|
| | mg/ml | mM | mg/ml | mM | Preferred | Suitable |
| Phenylephrine HCl | 18.33 | 90 | 13.7-22.9 | 68-112 | 720 | 360-1,080 |
| Ketorolac tromethamine | 4.24 | 11.25 | 3.2-5.3 | 8.5-14 | 89 | 44-134 |
| Citric acid monohydrate | 0.24* | | 0.12-1.20** | | | |
| Sodium citrate dihydrate | 5.48* | | 2.74-27.4** | | | |

*Corresponding to a 20 mM citrate buffer.
**Corresponding to a 10 mM to 100 mM citrate buffer.

TABLE 2

Example Formulation 2

| Component (USP) added to water for injection | Preferred Concentration | | Suitable Concentrations | | Representative Diluted Dosing Concentration (µM) | |
|---|---|---|---|---|---|---|
| | mg/ml | mM | mg/ml | mM | Preferred | Suitable |
| Phenylephrine HCl | 12.37 | 60.75 | 9.2-15.5 | 45-76 | 483 | 240-720 |
| Ketorolac tromethamine | 4.24 | 11.25 | 3.2-5.3 | 8.5-14 | 89 | 44-134 |
| Citric acid monohydrate | 0.24* | | 0.12-1.20** | | | |
| Sodium citrate dihydrate | 5.48* | | 2.74-27.4** | | | |

*Corresponding to a 20 mM citrate buffer.
**Corresponding to a 10 mM to 100 mM citrate buffer.

The amounts of pharmaceutically active ingredients included in the formulation can be expressed in molar ratios. The molar ratio of phenylephrine to ketorolac may range from 1:1 to 13:1, and more suitably may range from 3:1 to 10:1. An exemplary molar ratio of phenylephrine and ketorolac as represented by Formula 1 in Table 1 above is 8:1 of phenylephrine to ketorolac. Another exemplary molar ratio of phenylephrine and ketorolac as represented by Formula 2 in Table 2 above is 5.4:1 of phenylephrine to ketorolac.

Following dilution of the formulation of the present invention into an intraocular irrigation carrier for local delivery, the dosing concentration of phenylephrine may be from 3 to 7,200 µM, more suitably from 30 to 720 µM, more preferably from 90 to 720 µM, still more preferably from 240 to 720 µM, and most preferably about 483 µM. Following dilution of the formulation of the present invention into an intraocular irrigation carrier for local delivery, the dosing concentration of ketorolac may be from 3 to 900 µM, more suitably from 10 to 270 µM, more preferably from 44 to 134 µM, still more preferably from 30 to 90 µM, and most preferably about 90 µM.

Methods of Use

The stable liquid formulations of the present invention may be utilized after mixing with an intraocular irrigation carrier in a variety of ophthalmologic procedures. These include cataract extraction and lens replacement and refractive lens exchange procedures, corneal transplant procedures and vitreoretinal operations and trabeculectomy procedures for glaucoma.

One example of a suitable method of diluting and administering the combination drug composition of the present invention utilizes the formulation of the present invention described as Formula 2 in Table 2 above. A sterile, single-use 5 mL vial containing 4.5 mL of the composition in provided, from which 4 mL of the composition is withdrawn by syringe and mixed with 500 mL of BSS by injection into a 500 mL bag or bottle of BSS to provide a final concentration of 483 µM phenylephrine and 89 µM ketorolac. This solution is irrigated through the anterior chamber of the eye at a constant concentration throughout the procedure. As such, in this example, the drug product is only administered intracamerally during the procedure.

The active pharmaceutical agents are included at dilute concentrations in the intraocular irrigation carrier. The concentrations of the agents are determined in accordance with the teachings of the invention for direct, local application to ocular tissues during a surgical procedure. Application of the solution may be carried out perioperatively, i.e.: intra-operatively; pre- and intra-operatively; intra- and post-operatively; or pre-, intra- and post-operatively.

It must be noted that as used herein and in the appended claims, the singular forms "a", "and", and "the" include plural referents unless the context clearly dictates otherwise. Thus, for example, reference to "an excipient" includes a plurality of such excipients and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. All citations are incorporated herein by reference.

EXAMPLES

Examples 1-5

In the studies described in the following Examples 1-5, the presence of related substances (RS) and potency was measured by high performance liquid chromatography with UV detector (HPLC-UV) as an indication of stability, with an increase in the percentage of related substances detected indicating the presence of degradation products. In these studies, the HPLC-UV utilized a Zorbax XDB-C8, 5 µM, 4.6 mm×150 mm column with a flow rate of 1.2 ml/min. Mobile phases A and B were as follows: Mobile phase A: 650 mL of 1.1 mg/mL 1-octansulphonic acid, pH 3.0:50 mL of Milli-Q water:300 mL methanol. Milli-Q water: 300 mL methanol; Mobile phase B: 300 mL of 1.1 mg/mL 1-octansulphonic acid, pH 3.0:50 mL of Milli-Q water:650 mL methanol. The diluent used was mobile phase A. A gradient of 100% A to 100% B in 40 minutes was used. A 280 nm UV detector was used.

Example 1

Comparison of Stability of Formulations Depending on Use of a Preservative and an Antioxidant and Using Differing Buffers A study was run to compare different formulations of combinations of two active pharmaceutical ingredients (APIs), phenylephrine HCl (PE) and ketorolac tromethamine (KE), each at an equal concentration of either 5 mM or 1 mM in an aqueous solution. Two different buffering systems were utilized to maintain the solution at three different pHs: a 20 mM sodium phosphate buffer (dibasic sodium phosphate and monobasic sodium phosphate) for a pH of 7.4; a 20 mM sodium citrate buffer (citric acid monohydrate and sodium citrate dehydrate) for a pH of 6.5; and a 20 mM sodium citrate buffer for a pH of 5.5. Four preservative- and antioxidant-free formulations of these APIs were developed, each aliquoted into multiple 1 mL vials for storage and sampling, as follows:

TABLE 3

| Formulation ID | pH | Buffer | API Concentration |
|---|---|---|---|
| F1 | 7.4 | Na phosphate | 5 mM KE |
|  |  |  | 5 mM PE |
| F2 | 6.5 | Na citrate | 5 mM KE |
|  |  |  | 5 mM PE |
| F3 | 5.5 | Na citrate | 5 mM KE |
|  |  |  | 5 mM PE |
| F4 | 4.5 | Na citrate | 1 mM KE |
|  |  |  | 1 mM PE |

Additional formulations were then prepared by adding either no preservatives or antioxidants (the control group), or by adding the preservative sodium ethylenediamine tetraacetic acid (also referred to as edetate disodium or EDTA) or EDTA plus the antioxidant sodium metabisulfite, as follows:

TABLE 4

| Study Group | Study Conditions | | | |
|---|---|---|---|---|
| Group 1 (G1) | F1 | F2 | F3 | F4 |
| Group 2 (G2) | F1 + 0.05% w/v EDTA | F2 + 0.05% w/v EDTA | F3 + 0.05% w/v EDTA | F4 + 0.05% w/v EDTA |

TABLE 4-continued

| Study Group | Study Conditions | | | |
|---|---|---|---|---|
| Group 3 (G3) | F1 + 0.05% w/v EDTA + 0.05% w/v Na metabisulfite | F2 + 0.05% w/v EDTA + 0.05% w/v Na metabisulfite | F3 + 0.05% w/v EDTA + 0.05% w/v Na metabisulfite | F4 + 0.05% w/v EDTA + 0.05% w/v Na metabisulfite |

Samples of the various formulations in each of these groups were then stored under light shielded conditions at controlled temperatures of either 2-8° C., 25° C., 40° C. or 60° C. Samples of each formulation were pulled at various time points over a period of 12 months and analyzed for degradation of the APIs, as determined by measuring related substances for each API. The results from this study are set forth in the tables of FIGS. 1-12, and the following conclusions were reached.

Based on stability assessments after one month of storage:
1. The control group (G1) demonstrated that both APIs were stable in a Na Phosphate buffer at a pH of 7.4, and in a Na Citrate buffer at a pH of 6.5 and a pH of 5.5. The control group exhibited show some degradation at 60° C., with pH 4.5 (Na Citrate) showing the most.
2. The G2 group compared to the G1 group demonstrates that EDTA inhibits the degradation of PE at higher temperatures.
3. The G3 group surprisingly demonstrates that Na metabisulfite significantly increases the degradation of APIs, especially KE, at elevated temperatures. Additionally, at one month, some G3 samples stored at 40° C. and 60° C. turned yellowish.

Based on stability assessments after six months of storage:
4. EDTA surprisingly does not appear to have a significant effect on the stability of either API, especially in citrate buffer at a pH of 6.5.
5. The largest increase in the percent of related substances at 6 months occurs in the samples held at 60° C.
6. Both APIs appear stable at 4° C. and 25° C., with a small increase in percent of related substances at 40° C., especially in citrate buffer at a pH of 6.5.
7. At 6 months, samples at 40° C. and 60° C. appear bright yellow but without visible precipitation or crystallization.

Example 2

Effect of Nitrogen Overlay on Stability

A study was then run to determine the effect of a nitrogen overlay (i.e., the displacement of air from the head space in the vial with nitrogen before sealing the vial). The formula F2 from Example 1 (5 mM ketorolac, 5 mM phenylephrine in a sodium citrate buffer adjusted to pH 6.5 in an aqueous solution) was evaluated, either without any added preservative or antioxidant (group 1, G1) or with added 0.05% w/v EDTA as a preservative (group 2, G2). Related substances for each API were measured at time points over a one year period after storing samples at temperatures ranging from 4° C. to 60° C.

The results of this study are shown in FIGS. 13 and 14, and demonstrate that the use of a nitrogen overlay, as compared to the presence of oxygen containing air, significantly decreased the degradation of both APIs, especially at elevated temperatures of 40° C. and 60° C. When a nitrogen overlay was used, the presence or absence of EDTA made little difference on the stability of the APIs.

Example 3

Effect of Different Antioxidants on Stability

A study was then carried out to evaluate the effect of adding alternate antioxidant agents to the formula F2 from Example 1 (5 mM ketorolac, 5 mM phenylephrine in a sodium citrate buffer adjusted to pH 6.5 in an aqueous solution) that also included 0.05% w/v EDTA as a preservative (group 2, G2). The antioxidants evaluated were 0.1% ascorbic acid (A1), 0.1% L-cysteine HCL monohydrate (A2), 0.1% L-glutathione, reduced (A3) and 0.1% monothioglycerate (A4). Related substances for each API were measured at time points over a one month period after storing samples at temperatures ranging from 2-8° C. to 60° C.

The results of this study are shown in FIGS. 15-18, and demonstrate that, at the one month time point, these four antioxidants each surprisingly increased the degradation of each API, especially at elevated temperatures of 40° C. and 60° C.

Example 4

Evaluation of Stability of Higher Concentrations of Phenylephrine

To evaluate whether the concentration of phenylephrine in the phenylephrine HCl and ketorolac tromethamine combination formulations could be increased without deleterious effect on stability of the phenylephrine, an aqueous formulation of 450 mM phenylephrine in a calcium citrate buffer adjusted to a pH of 6.5, and no added preservatives, antioxidants or other excipients, was prepared and evaluated when samples were stored at temperatures between 4° C. and 40° C. over a period of 4 months.

The results of this study are provided in FIG. 19. This high concentration phenylephrine formulation was stable between 4° C. and 30° C. for 4 months.

Example 5

Evaluation of Extended Stability of Phenylephrine and Ketorolac Combination

An extended stability study was performed for a formulation of a fixed combination of phenylephrine HCl (12.37 mg/mL) and ketorolac tromethamine (4.24 mg/mL) in a 20 mM sodium citrate buffer adjusted to pH 6.5, without the addition of any preservatives or antioxidants. Samples of the formulation where aliquoted into 5 mL USP Type 1 glass vials, closed with Daiko D777-1 Flurotec® coated 20 mm stoppers, and stored inverted and foil wrapped for light shielding, and then were held under long term (5±3° C.) and accelerated storage conditions (25±2° C./60±5% RH). Each vial contained 4.5 mL of solution, including a 0.5 mL overfill.

There was no measurable change in product appearance, pH of solution, or potency when measured after 30 months of storage under these conditions. At this 30 month time point, storage at 5° C. and 25° C. resulted in a total of 1.17% and 1.36% related substances, respectively. A graphic display of measured potency of phenylephrine HCl and ketorolac tromethamine for this formulation held under labeled storage conditions of 2° C. to 8° C. is provided in FIG. 20A and FIG. 20B, respectively. As evidenced in these figures, there was no significant decline in potency observed through 30 months (three vials were assayed at each time point).

Examples 6-9

The following Examples 6-9 provide the results of in vivo studies of phenylephrine HCl and ketorolac tromethamine combination formulations in accordance with the present invention, which have been diluted by injections into an irrigation solution that was then used for intraocular irrigation during lens replacement and exchange surgery. The following formulations were evaluated in this series of studies: (a) phenylephrine HCL alone (PE), (b) ketorolac trometahamine alone (KE), (c) a combination of phenylephrine HCL and ketorolac trometahamine (PE-KE) or (d) no active pharmaceutical ingredients (vehicle control), in each case formulated in an aqueous solution including a 20 mM sodium citrate buffer adjusted to pH 6.5, without the addition of any preservatives or antioxidants, in each case provided in 2.5 mL aliquots. In each case an aliquot of the formulation was injected into a balanced salt solution (BSS, Baxter Healthcare, produce code 1A7233) as the irrigation vehicle carrier to a particular final dosing concentration as described below. The studies also utilized Proparacaine HCl (0.5%, Bausch & Lomb), Tropicamide (1.0%, Bausch & Lomb) and Ciprofloxacin HCl (3%, Alcon) to the extent described below.

The mydriatic and anti-inflammatory properties of the test agents were evaluated in an African green monkey model of human phacoemulsification surgery. Prior to surgery, baseline measures and assessments were performed on both eyes in each monkey to determine pupil diameter, lens and iris integrity, corneal thickness, and anterior chamber flare and cell count by qualitative scoring under biomicroscopy and quantitative flare photometry using a Kowa FM-500 instrument. A phacoemulsification surgery with lens replacement with a polymethyl methacrylate (PMMA) artificial lens was performed using a Storz Premier anterior phacoemulsification machine. The procedure was only performed on the right eye to minimize surgery position variability, allow the left to serve as control, and to minimize the consequence of any possible vision loss induced.

Test animals were placed in a prone position under ketamine/xylazine anesthesia augmented with one drop of topical proparacaine. A small incision was made in the cornea of the right eye with a MVR 20 G lance blade, through which 0.4-0.6 mL of viscoelastic (2% hydroxypropyl methylcellulose, EyeCoat, Eyekon Medical) was introduced into the anterior chamber via a viscoelastic injector. A corneal incision was made 1.0 mm anterior to the limbus using a 2.65 mm straight clear cornea bi-beveled blade. Irrigation was applied with the phacoemulsification hand piece to remove viscoelastic and introduce the test perfusate. After irrigation for a total of four minutes, irrigation was stopped and the anterior chamber refilled with viscoelastic. A capsulorhexis was performed and the phacoemulsification tip reintroduced into the anterior chamber with the application of phacoemulsification energy to disrupt the lens and allow aspiration and lens fragment removal. Irrigation was extended for a period after lens removal to standardize intraocular perfusate delivery across all treatment groups (a total of 14 minutes during this phacoemulsification segment of the irrigation). Following the phacoemulsification and irrigation procedure, a PMMA intraocular lens (IOL) was inserted and an additional two minutes of irrigation perfumed, after which the corneal incision was closed with two 12.0 nylon sutures. Irrigation with a test fluid or vehicle control, as described below, was performed for a total of 20 minutes at a flow rate of 20 mL/min, prior to, during and after phacoemulsification and lens replacement.

In these studies, laser flare photometry was performed at baseline, 4.5, 24, 48 hours and 1 week after the initiation of the surgical procedure using a Kowa FM-500 (Kowa Company, Tokyo Japan). The Kowa FM-500 measures laser light scattering to quantify anterior chamber flare. A laser is directed into the anterior chamber and protein molecules, released into the anterior chamber during an inflammatory response, pass through the focal point scattering laser light. This light scattering is quantified by a photomultiplier tube as photon counts per millisecond. At each observation point, measurements were collected until seven acceptable readings (difference between two background measurements <15%) were obtained and the lowest and highest readings were deleted and the mean value+/−the standard deviation calculated, as specified by the manufacturer.

The time course of the mydriatic effect was documented through video recording of the pupil during the perfusion procedure. Pupil diameter and the fixed width of the lid speculum (11 mm) were measured from the screen image to allow calculation of the pupil diameter in millimeters. Measurements were made at periodic intervals during the course of the infusion procedure according to the video time log for each documented procedure.

The primary efficacy variables were the pupil diameter and the laser flare photometer measures. Primary efficacy variables were analyzed in the protocol correct population (all subjects who completed the study without a major protocol deviation) using a one-way, repeated measure ANOVA method with post hoc Student Newman-Keuls tests employing SAS (SAS Institute Inc.). Terms of the ANOVA analysis included sequence (=time, confounded with carry-over effect), eye, monkey and treatment. Appropriate model-based comparisons were employed to detect treatment difference at the significance level of $p<0.05$ for pupil diameter and flare measures at all time points.

Example 6

Concentration-Ranging Study of Phenylephrine and Ketorolac Following Intraoperative Irrigation in a Phacoemulsification Surgical Model A non-GLP study was conducted as a concentration-ranging efficacy study to evaluate PE and KE when given individually and combined via intraocular irrigation in BSS during cataract surgery. The objectives were to evaluate the benefit of each agent on both mydriatic and inflammatory endpoints.

In a first series of experiments, designated Phase 1, 16 animals were divided into groups of four and studied to establish the maximally effective concentration of phenylephrine in a BSS irrigation solution in this model of phacoemulsification surgery. Four of the monkeys in the Phase 1 cohort received tropicamide, a muscarinic mydriatic, to serve as a positive control and allow determination of the endpoint measures of interest under adequate pupil dilation by the standard topical preoperative route of delivery. The phenylephrine treatment groups received a low (3 µM), intermediate (10 µM), high (30 µM) and highest (90 µM) concentration of phenylephrine-containing BSS perfusate. The low and highest treatment groups consisted of 2 animals each as the decision was made to evaluate a higher concentration of phenylephrine as the phase 1 portion was underway. The primary endpoint for phenylephrine efficacy was mydriasis. Inflammatory endpoints following the surgery were also evaluated.

BSS perfusate was delivered through the phacoemulsification needle either without phenylephrine or containing phenylephrine at a concentration of 3.0 µM, 10 µM, 30 µM or 90 µM (see Table 1). Stage 1 irrigation (0:00-2:00 minutes) was applied to remove the viscoelastic and assess the mydriatic effect of phenylephrine and continued through Stage 2 irrigation (2:00-4:00 minutes), after which viscoelastic was reintroduced into the anterior chamber and a capsulorhexis was performed. Stage 3 irrigation (4:00-18:00 minutes) was begun after the capsulorhexis and continued for a total of 14 minutes, during the early stage of which the lens was fragmented and aspirated by application of phacoemulsification energy. Stage 4 irrigation took place after the introduction of the PMMA lens to evacuate viscoelastic material introduced for that procedure and to remove any additional lens fragments. The tropicamide control animals were pre-treated with two drops of 1% tropicamide 20 minutes prior to the initiation of anterior chamber irrigation with BSS alone.

Following the first few animal surgeries, the duration of the initial pre-phacoemulsification irrigation was extended from 2 to 4 minutes to capture maximal pupil dilation.

The second series of experiments, designated Phase 2, evaluated mydriasis and inflammation following phacoemulsification surgery in which a BSS perfusate containing low, mid and high concentration of ketorolac, or no ketorolac (negative control) was employed. Anterior chamber perfusions were initiated using no mydriatic agent in the irrigation solution to assess the mydriatic effect of ketorolac and BSS alone. After 2 minutes of irrigation and assessment of mydriasis, a concentration of phenylephrine (30 µM), found to be effective in achieving mydriasis in Phase 1 experiments, was included in the perfusate solution to provide sufficient dilation for the phacoemulsification procedure to be performed. The secondary endpoint for ketorolac efficacy was mydriasis, and the primary endpoint was laser flare photometry, a validated measure of anterior chamber inflammation.

BSS perfusate was delivered through the phacoemulsification needle either without ketorolac or containing ketorolac at a concentration of 3.0 µM, 10 µM, or 30 µM (see Table 1). Stage 1 irrigation (0:00-2:00 minutes) was applied to remove the viscoelastic and assess the mydriatic effect of ketorolac. High concentration phenylephrine was then added to the perfusate bottle (to achieve a concentration of 30 µM), the lines were flushed and irrigation was continued through stage 2 (2:00-4:00 minutes), after which viscoelastic was reintroduced into the anterior chamber and a capsulorhexis was performed. Stage 3 irrigation (4:00-18:00 minutes) was begun after the capsulorhexis and continued for a total of 14 minutes, during the early stage of which phacoemulsification energy was applied. Stage 4 irrigation took place after the introduction of the PMMA lens.

Results

After an initial pupil dilation of 1-2 mm within the first minute of the start of anterior chamber perfusion, the pupil diameter asymptotically approached maximal dilation within approximately five minutes for all treatment groups (see FIGS. 21 and 22) with a significant effect of time on diameter (F=2.75, P<0.0001). In the first set of experiments, trends suggest that the presence of phenylephrine in the BSS perfusate contributed to a concentration-dependent increase in pupil diameter. The initial dilation (0-2 min) exhibited in the control group, which received topical tropicamide 20 minutes prior to irrigation with BSS alone, was likely not a pharmacologic effect and reflects a component of the dilation measured within the first 2 minutes of the onset of anterior chamber irrigation in all groups was related to clearance of the viscoelastic introduced to allow creation of the corneal incision and a possible hydrodynamic effect of irrigation/aspiration. Of note, however, the early additional dilation in the tropicamide control group started from a baseline dilation greater than all other treatment groups (F=7.73, P<0.0001) at the beginning of the procedure and resulted in a lower maximal dilation than exhibited by the mid, high and highest concentration phenylephrine groups. Differences between the highest, high and mid phenylephrine groups and the low phenylephrine group were significant at the 6:00, 8:00, 10:00, 14:00, 18:00 and 19:00 minute time points (F=2.41, p<0.043; F=2.66, p<0.0315; F=3.24, p<0.0136; F=6.62, p<0.0002; F=9.26, p<0.0001; F=3.79, p<0.005; respectively; Student Newman-Keuls test, $\alpha$=0.05, df=23, see FIG. 21), confirming a concentration-dependent effect of phenylephrine perfusate on the amplitude of intraoperative mydriasis. Differences between the highest, high and mid-concentration phenylephrine groups versus the low concentration phenylephrine and tropicamide control group were significant at the 14:00 and 18:00 minute time points (F=6.62, p<0.0002; F=9.26, p<0.0001; respectively; Student Newman-Keuls test, $\alpha$=0.05, df=23, see FIG. 21), indicating the concentration-dependent effect of phenylephrine in prolonging intraoperative mydriasis. Differences between all other groups at all other time points were not significant by the Student Newman-Keuls criteria, but trends observed in the mean pupil diameter within groups would suggest a concentration dependence to both rate of onset and amplitude of mydriatic effect across phenylephrine groups. At later time points mean dilation in the high phenylephrine treatment group approaches the anatomic limit of pupil mydriasis of 8.3 mm in the adult eye in this species (corresponding to the inner diameter of the corneal limbus).

In the second set of experiments, in which the anterior chamber was irrigated with BSS containing 3-30 µM ketorolac or BSS alone for 2 minutes prior to the introduction of 30 µM phenylephrine, there was a rapid 1-2 mm increase in pupil diameter within 30 seconds of the start of perfusion followed by a less rapid concentration-independent rise between 30 seconds and two minutes. No statistical differences were seen between the ketorolac-treated groups and the BSS-treated animals during the initial two minutes. Given that the same behavior was demonstrated by the BSS control group it is likely that this initial dilation is related to viscoelastic clearance and the hydrodynamic effects of irrigation/aspiration, as evidenced by the behavior of the phenylephrine and tropicamide control groups in the first set of experiments. After introduction of 30 µM phenylephrine in all ketorolac- and BSS-treated animals at two minutes there was a further rapid increase in pupil diameter in all groups reaching maximum dilation at four minutes. Maximal dilation was sustained through the remaining perfusion period after a slight decrease in pupil diameter in the interval between the four minute initial perfusion and the start of phacoemulsification when the capsulorhexis was performed. There were no statistically significant group differences, except between the low and mid concentration ketorolac groups versus the BSS and high concentration ketorolac groups at the 14:00 and 18:00 minute time points (Low and Mid>BSS and High; F=6.62, p<0.0002; F=9.26, p<0.0001; respectively; Student Newman-Keuls test, $\alpha$=0.05, df=23, see FIG. 2). The treatment grouping of this difference, however, would suggest that the difference did not result from a ketorolac effect, and was likely related to the limited sample size, and reflective of inter-animal and inter-procedure differences. In all treatment groups in both sets of experiments studies the pupil constricted following lens placement at the end of the procedure.

Baseline preoperative anterior chamber flare measures ranged from 3.0 to 12.7 photon units/ms (mean=6.0+/−2.4 SD) in all treatment groups in the treated (right) eye. Flare measures in the control (left) eye remained within this range throughout the duration of the study. These measures matched anterior chamber flare assessments performed by slit lamp biomicroscopy, validating the utility of the laser flare photometer in quantifying the protein density in the anterior chamber in the eye's quiescent natural state. In all treatment groups there was a significant effect of time on flare measurements in the treated eye (F=2.16, p<0.0034), further confirming the utility of flare photometry in quantifying intervention related inflammation (see FIGS. 23, 24 and 25). Flare measures in treated eyes at baseline versus 4.5 and 24 hours versus 48 and 168 hours were significantly different across all treatment groups (F=2.16, p<0.0034; Student Newman-Keuls test, $\alpha$=0.05, df=75). Differences between the control and treated eye were different at all postoperative exam time points across all subjects (F=236.64, P<0.0001; Student Newman-Keuls test, $\alpha$=0.05, df=195).

In the first set of experiments, phacoemulsification duration differed within treatment groups as ideal parameters were being refined. It was established in the first 4 surgical procedures that the phacoemulsification time was causing a severe inflammatory response and reduction in phacoemulsification was agreed to. Analysis of longer duration phacoemulsification (45-55 secs) versus shorter duration (15-25 secs) groups at the 4.5 hour and 24 hour time points revealed a statistically significant increase in flare measures with phacoemulsification duration (F=4.42, p<0.0018; Student Newman-Keuls test, $\alpha$=0.05, df=14; see FIG. 24), confirming the utility of laser flare photometry in quantifying the extent of anterior chamber injury and inflammation. This difference resolved by the 48 and 1 week time points.

Analysis with the exclusion of the high phacoemulsification energy subjects, which included 2 monkeys in each of the high phenylephrine and tropicamide groups, revealed no treatment effect on flare measures of phenylephrine relative to the tropicamide control at all time points (Student Newman-Keuls test, $\alpha$=0.05, df=7).

In the second set of experiments, despite the small group sizes, there was a consistent trend for a reduction in the flare measurements in the mid and high ketorolac groups. There was a statistically significant difference between flare measures in the BSS control group versus the mid and high concentration ketorolac groups which achieved significance at the 4.5 hour time point when these two treatment groups were combined to add power to the analysis (F=5.17, P<0.0223; Student Newman-Keuls test, $\alpha$=0.05, df=13; see FIG. 25). Flare measurements in the high and mid dose ketorolac group remained lower relative to the control group at the 24 and 48 hour time points, but these differences did not achieve statistical significance, whether the high and mid dose ketorolac groups were analyzed in combination or separately, given the power of the analysis. At one week there were not statistically significant difference between any of the treatment groups but the high concentration ketorolac group maintained a similar trend.

Conclusions

The African green monkey phacoemulsification model allowed the quantification of mydriatic and inflammatory measures relevant to human clinical endpoints. Of these measures, video pupil diameter assessments and anterior chamber flare photometry were the most responsive to treatment effects at the time points assessed. Video pupil data demonstrated that intraoperative delivery of phenylephrine in the anterior chamber perfusate resulted in a rapid onset mydriasis which was maintained throughout the surgical procedure. The maximal mydriasis attained was concentration-dependent, with adequate mydriasis for a phacoemulsification surgical procedure to be performed at all concentrations evaluated. Concentrations equal to or greater than 10 µM resulted in a mydriasis exceeding that obtained by preoperative topical 1% tropicamide, a standard of care for cataract procedures. Flare photometry and pachymetry measures did not indicate a reduction in anterior chamber inflammation or corneal edema associated with the addition of phenylephrine to the anterior chamber perfusate.

Video pupil data demonstrated that intraoperative delivery of ketorolac in the anterior chamber perfusate did not result in a change in mydriasis substantially different from that observed with BSS alone. Once phenylephrine at a concentration of 30 µM was added to the perfusate, however, rapid dilation occurred, confirming the previously demonstrated utility of the intraoperative delivery of phenylephrine. Flare photometry measures indicated a positive effect of ketorolac on anterior chamber inflammation immediately postoperatively at 4.5 hours.

Example 7

Study of Phenylephrine and Ketorolac Combination in Phacoemulsification Surgical Model A non-GLP study was conducted with an irrigation solution containing 90 µM PE and 30 µM KE to evaluate the effect of the combination when administered via intraocular irrigation during cataract surgery on mydriasis and inflammatory endpoints. In this series of experiments, 14 monkeys were divided into groups of seven and studied to establish the efficacy of BSS alone versus a BSS perfusate containing the PE and KE combination. Efficacy endpoints included mydriasis and laser flare photometry as a measure of anterior chamber inflammation. The control group additionally received the muscarinic mydriatic tropicamide preoperatively to allow sufficient dilatation to employ the African green monkey model of phacoemulsification surgery.

Results

Animals irrigated with the PE-KE combination achieved 6.0-6.5 mm pupil dilation within approximately 60 sec of irrigation (see FIG. 26). These values were equivalent to those obtained after preoperative treatment with tropicamide. After an initial pupil dilation of 3.0-4.0 mm within the first minute of the start of anterior chamber perfusion, the pupil diameter plateaued within approximately 2.5 and 3.5 minutes for both the tropicamide control and the PE-KE treatment groups, respectively (see FIG. 1), with a significant effect of time on pupil diameter (F=86.69, P<0.0001; Student Newman-Keuls test, α=0.05, df=12). The initial dilation (0-2 min) exhibited in the control group, which received topical tropicamide 20 minutes prior to irrigation with BSS alone, was likely not a pharmacologic effect and reflects hydrodynamic effects of irrigation/aspiration and/or dilation associated with clearance of the viscoelastic introduced to allow creation of the corneal incision. Of note, however, the early additional dilation in the tropicamide control group started from a baseline dilation greater than the treatment group (F=86.69, P<0.0001; see FIG. 26) at the beginning of the procedure and resulted in a lower maximal dilation than exhibited by the PE-KE treatment group. PE-KE-mediated pupil dilation exceeded the dilation achieved by the preoperative administration of tropicamide within 90 seconds of the initiation of anterior chamber irrigation. Differences between the control group and the treatment group receiving PE-KE were significant at the 0:00, 3:30, 4:00, 4:30, 5:00, 5:30, 6:00, 8:00, 10:00, 12:00, 12:30 and 13:00 minute time points (F=25.08, p<0.003; F=5.61, p<0.0355; F=9.95, p<0.0083; F=14.71, p<0.0024; F=18.01, p<0.0011; F=9.93, p<0.0084; F=10.39, p<0.0073; F=14.77, p<0.0023; F=14.77, p<0.0023; F=28.65, p<0.0002; F=20.51, p<0.0007; F=8.66, p<0.0134; F=5.48, p<0.0391, respectively; Student Newman-Keuls test, α=0.05, df=12; see FIG. 26).

The observed group differences confirmed a treatment effect of the PE-KE perfusate containing phenylephrine and ketorolac on the amplitude of intraoperative mydriasis and on the prolongation of intraoperative mydriasis. Differences between the two groups at early time points were not significant by the Student Newman-Keuls criteria, reflecting intra-group variability, but trends observed in the mean pupil diameter suggest a treatment effect to both rate of onset and amplitude of mydriatic effect. At later time points mean dilation in some subjects in the PE-KE treatment group approached the anatomic limit of pupil mydriasis of –10.5 mm in the adult eye in this species (corresponding to the inner diameter of the corneal limbus).

Baseline preoperative anterior chamber flare measures ranged from 1.6 to 9.9 photon units/ms (mean=5.3+/−2.3) in both treatment groups in the operative (right) eye. In both treatment groups there was a significant effect of time on flare measurements in the treated eye, further confirming the utility of flare photometry in quantifying intervention related inflammation (see FIG. 27). Flare measures in treated eyes at baseline versus 2, 4.5, 24, 48 hours and 1 week were significantly different across both treatment groups (F=4.94, p<0.0008; Student Newman-Keuls test, α=0.05, df=59).

The PE-KE treatment group had lower values of flare measures over time relative to the tropicamide control group, but they did not achieve statistical significance at any time point (F=3.32, P<0.0935; Student Newman-Keuls test, α=0.05, df=12; see FIG. 27), in part reflecting a large variability in subject response to the experimental intervention. One PE-KE treated subject exhibited a more limited pupil dilation during anterior chamber irrigation, complicating lens removal. Analysis of flare measures with the exclusion of this animal reveal a statistically significant difference between the PE-KE treatment group and the tropicamide control group at the 2-, 4.5-, 24- and 48-hour time points (F=9.74, P<0.0097; Student Newman-Keuls test, α=0.05, df=11; see FIG. 28). At one week there was not a statistically significant difference between the treatment groups.

Conclusions

The African green monkey phacoemulsification model allowed the quantification of mydriatic and inflammatory measures relevant to human clinical endpoints. Of these measures, video pupil diameter assessments and anterior chamber flare photometry were the most responsive to treatment effects at the time points assessed. Video pupil data demonstrated that intraoperative delivery of PE-KE in the anterior chamber perfusate resulted in a rapid onset of mydriasis, which was maintained throughout the surgical procedure. The mydriasis attained was adequate for a phacoemulsification surgical procedure to be performed within the initial 60 seconds of irrigation. The degree of mydriasis exceeded that obtained by preoperative topical 1% tropicamide, a standard of care for cataract procedures. Flare photometry measures suggest a positive effect of PE-KE on anterior chamber inflammation immediately postoperatively.

Example 8

Dose Response Study of Phenylephrine and Ketorolac Combination in Phacoemulsification Surgical Model This non-GLP study was conducted to establish the dose response and time course of mydriasis following intracameral delivery of low-, mid-, and high-concentration irrigation solutions containing PE and KE to African green monkeys. The PE-KE formulation contained a fixed ratio of 3:1 of 45 mM phenylephrine and 15 mM ketorolac in a 20 mM sodium citrate buffer (pH 6.5). An additional concentrated 450 mM phenylephrine HCl (PE) formulation was provided to elevate the phenylephrine concentration in the high dose group. The time course of mydriasis was evaluated by video in four monkeys following intracameral administration of the low concentration of PE and KE (90:30 µM) irrigation solution, in four monkeys following the mid concentration (268:89 µM) and four monkeys following the high concentration (1165:89 µM). The volumes of all intracameral administrations were 150 µL with ejection of the syringe volume into the anterior chamber occurring over approximately a five-second period.

To mix the low concentration (PE:KE at 90:30 µM) 1.0 mL from one vial of PE-KE drug composition was withdrawn and injected into a 500-mL BSS irrigation bottle. For the mid concentration (PE:KE at 268:89 three vials of PE-KE drug composition were used with 1.0 mL from each vial withdrawn and injected into a 500-mL BSS irrigation bottle. For the high concentration group (PE:KE at 1165:89 additional phenylephrine HCl was added to the PE:KE in BSS solution.

Results

Monkeys injected with intracameral PE/KE irrigation solution achieved approximately 6-7 mm pupil dilation within 60 seconds of irrigation. As shown in FIG. 29, after an initial rapid pupil dilation, the pupil diameter plateaued at approximately the 1-minute time point, with a significant effect of time on pupil diameter among all treatment groups (F=64.33, p<0.0001). Differences between the low-dose group (90:30 µM) and the high-dose group (1165:89 µM)

were statistically significant at the 1:30-, 3:00- and 3:30-minute time points (Student Newman-Keuls test, α=0.05, df=9).

Conclusions

The African green monkey mydriasis model allowed the quantification of pupil responses that are relevant to human clinical endpoints. Video pupil data demonstrated that intracameral delivery of PE-KE into the anterior chamber resulted in a rapid onset mydriasis, which was maintained throughout the ten minute period during which video documentation occurred. The mydriasis attained was adequate for a phacoemulsification surgical procedure to be performed within the initial 60 seconds following administration. The degree of mydriasis was greater than that obtained in the control arm of previous efficacy studies by the preoperative delivery of topical 1% tropicamide (mean pupil diameter of 5.9 mm), a standard of care for cataract procedures.

Example 9

Safety Study of Phenylephrine and Ketorolac Combination in Phacoemulsification Surgical Model A nonclinical GLP toxicology study was carried out in African green monkeys. Twelve male and twelve female monkeys underwent phacoemulsification surgery with lens replacement and two-week recovery in this study. Continuous irrigation of PE-KE irrigation solution throughout the anterior chamber and associated ocular structures was conducted during the surgery and represents the intended route of administration of this product. Three concentrations were evaluated: 720 μM PE and 90 μM KE (720:90 μM) in the low concentration group, 2160 μM PE and 270 μM KE (2160:270 μM) in the mid concentration group, and 7200 μM PE and 900 μM KE (7200:900 μM) in the high concentration group.

A separate control group was evaluated as well. An equal number of male and female animals were allocated to each group with assignment based on weight rank to achieve a balanced mean weight. All animals underwent a surgical procedure on Day 0 to replace the intraocular lens.

Results

All animals tolerated the surgical procedures well, had uneventful recoveries, and survived to the scheduled sacrifice and necropsy. No treatment-related effects were observed on respiratory and cardiovascular observations and all clinical laboratory parameters.

The initial intracameral delivery of 150 μL of each PE/KE irrigation solution resulted in rapid pupil dilation within 30 seconds, with dilation increasing to 6.76±0.15 to 7.29±0.15 mm (mean±SD) in a dose-dependent manner. Thirty seconds following intracameral delivery of 150 μl of BSS alone, the pupil diameter of the tropicamide control group was 5.18±0.18 mm.

The low-concentration treatment group had lower values of flare measures relative to the tropicamide control group at 4.5 hours and 14 days, but they did not achieve statistical significance at any time point, while flare response in the high-concentration treatment group was nearly identical to that of the control group at all time points. The mid-concentration treatment group had higher flare measures relative to the tropicamide control, low-concentration and high-concentration at all post-surgical time points, achieving significance at 2, 4.5, and 24 hours. These findings are believed secondary to greater surgical trauma in the mid-concentration treatment group. No concentration-dependent effects on flare were seen. At two weeks, there was not a statistically significant difference between the treatment groups.

In the control, low-concentration, and high-concentration treatment groups, there was a decrease in intraocular pressure following phacoemulsification surgery, but differences from baseline did not achieve significance. At the 4.5-hour time point, the intraocular pressure in the mid-concentration treatment group was significantly greater than in the other treatment groups, but not different than baseline. There was an overall trend of decreasing postoperative intraocular pressure.

Baseline clinical evaluations of the pupil, cornea, lens, and iris were within normal limits in the operative (right) and nonoperative (left) eye of all animals. The pupil diameter returned to baseline by the 24-hour time points, indicating minimal residual treatment-associated mydriatic or miotic effect.

Example 10

Clinical Study

A Phase 2b human clinical study evaluated a ketorolac and phenylephrine combination drug composition, formulated in accordance with Formula 1 of the present invention-, for its effect on the maintenance of intra-operative mydriasis (pupil dilation) and reduction of postoperative pain and irritation resulting from cataract and other lens replacement surgery. The combination drug composition was diluted into a balanced salt solution irrigation carrier prior to intraocular administration during intraocular surgical procedures.

The subject Phase 2b study was a randomized, parallel group, vehicle-controlled, factorial design study, and was run to compare phenylephrine (PE), ketorolac (KE) and the combination drug composition containing both PE and KE in subjects undergoing unilateral cataract extraction with lens replacement (CELR) using a coaxial phacoemulsification process with insertion of an acrylic lens. Administration of test irrigation solutions occurred in a double-masked fashion. The study evaluated, in a four-arm full-factorial design, the contribution of the two active pharmaceutical ingredients (PE and KE, alone and in combination) to the maintenance of mydriasis and post-operative reduction in pain when administered diluted in balanced salt solution (BSS). The study also explored the effect of the combination drug composition, PE, and KE on postoperative inflammation. Subjects were randomized to one of the following four treatment arms in a 1:1:1:1 fashion:

a. BSS vehicle
b. 483 μM PE in BSS
c. 89 μM KE in BSS
d. the combination drug composition containing 483 μM PE and 89 μM KE in BSS.

All subjects in this study received preoperative mydriatics and anesthetics. In each of the four groups, the respective irrigation treatment was administered as a single irrigation of the anterior chamber of the eye during the CELR surgical procedure, with a mean of 8 minutes of exposure in this study. In addition, at the end of the procedure, the anterior chamber was filled with the irrigation treatment. The change in pupil diameter over time from surgical baseline (immediately prior to surgical incision) to the end of the surgical procedure (wound closure) was measured, as was postoperative pain on the day of operation as measured by the Visual Analog Scale (VAS) at 2, 4 6, 8 and 10-12 hours and at other times recorded by the patient prior to taking rescue pain medication.

In this 223-patient Phase 2b clinical study, subjects treated with the combination drug composition demonstrated statistically significant (p<0.0001) and clinically meaningful maintenance of mydriasis throughout the cataract procedure as compared to either the BSS or KE groups. Maintenance of mydriasis is critical to performing lens exchange safely and proficiently given that the ophthalmologist operates through the pupil. If mydriasis is not maintained throughout the procedure, the risk of injuring structures within the eye increases and the required operating time is often prolonged. Any reduction in pupil size during surgery may interfere with surgical technique. In this study the mean pupil diameter was 8.3 mm at the time of the incision. A reduction of 2.5 mm or more ("extreme constriction") represents a loss of 30% of the diameter and 52% of the area of the average pupil, with a potential for extreme impact on the procedure. Unexpectedly, this study demonstrated that 21% of subjects in the BSS group and 21% of subjects in the KE group experienced this extreme constriction, as compared to only 4% of subjects in the combination drug composition group.

Intraoperative complications increase when the pupil diameter is less than 6 mm during lens exchange surgery. A categorical analysis on an intent-to-treat basis of intraoperative pupil diameters to identify the proportions of study subjects who experienced this level of pupil constriction. In this Study, the combination drug composition was statistically significantly superior (Table 5) in preventing this degree of pupil constriction, i.e., miosis to a diameter of less than 6 mm, when compared to each of the other three treatment arms.

TABLE 5

Subjects Having Pupil Diameter <6 mm during CELR

| BSS (n = 54) | KE/PE Combination (n = 49) | KE (n = 52) | PE (n = 49) |
|---|---|---|---|
| 25 (46%) p < 0.0001* | 3 (6%) | 18 (35%) p = 0.0005* | 11 (22%) p = 0.0404* |

*FET comparison to PE-KE combination

Clinically significant reductions in pupil diameter are associated with an increase in procedure-related complications, including posterior capsule tears, retained lens fragments and vitreous leaks. These findings demonstrate that the phenylephrine and ketorolac each contribute and act synergistically in preventing clinically meaningful miosis.

This finding is surprising because phenylephrine is a strong mydriatic agent and would be expected to inhibit miosis alone. Surprisingly, ketorolac also provided an antimiotic effect on top of the effect of phenylephrine.

Additionally, the combination drug composition also significantly decreased pain in the early postoperative period (10-12 hours post-surgery) relative to either the PE (p=0.0089) or BSS (p=0.0418) groups. Surprisingly, the combination drug composition also reduced the frequency of complaints of moderate and severe pain (2.5 times more complaints in the BSS-treated subjects). The drug composition was safe and well tolerated in this study.

This study demonstrates that the composition and use of the invention claimed in the above-identified application prevents a surprising degree of extreme pupil constriction, as well as resulting in an unexpected reduction of moderate and severe post-operative pain up to 10-12 hours after surgery following mere minutes of exposure to the test drug during surgery.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

The embodiments of the inventions in which an exclusive property or privilege is claimed are defined as follows:

1. A liquid pharmaceutical dosage form comprising phenylephrine, ketorolac, a buffer system, an intraocular irrigation carrier and an inert gas overlay in a single-use container, wherein the phenylephrine is included at a concentration of from 30 to 720 μM and the ketorolac is included at a concentration of from 10 to 270 μM.

2. The dosage form of claim 1, wherein the phenylephrine is included at a concentration of from 90 to 720 μM and the ketorolac is included at a concentration of from 44 to 134 μM.

3. The dosage form of claim 1, wherein dosage form is stable for a period of at least 24 months when stored at a temperature of from 5+/−3° C. to 25+/−2°C.

4. The dosage form of claim 1, wherein the dosage form is preservative-free and antioxidant-free.

5. The dosage form of claim 4, wherein dosage form is stable for a period of at least 24 months when stored at a temperature of from 5+/−3° C. to 25+/−2°C.

6. The dosage form of claim 1, wherein the buffer system is selected from a sodium phosphate buffer system and a sodium citrate buffer system.

7. The dosage form of claim 6, wherein the buffer system comprises a sodium citrate buffer system.

8. The dosage form of claim 7, wherein the buffer system comprises an about 20 mM sodium citrate buffer system.

9. The dosage form of claim 1, wherein the dosage form has a pH of from 5.8 to 6.8.

10. The dosage form of claim 1, wherein the inert gas overlay is a nitrogen gas overlay.

* * * * *